(12) United States Patent
Sibary et al.

(10) Patent No.: US 12,156,676 B2
(45) Date of Patent: Dec. 3, 2024

(54) ARRAY INSERTION TOOL

(71) Applicant: COCHLEAR LIMITED, New South Wales (AU)

(72) Inventors: Peter Raymond Sibary, Macquarie University (AU); Nicholas Charles Pawsey, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1123 days.

(21) Appl. No.: 16/975,815

(22) PCT Filed: Feb. 26, 2019

(86) PCT No.: PCT/IB2019/051546
§ 371 (c)(1),
(2) Date: Aug. 26, 2020

(87) PCT Pub. No.: WO2019/162930
PCT Pub. Date: Aug. 29, 2019

(65) Prior Publication Data
US 2020/0405351 A1    Dec. 31, 2020

Related U.S. Application Data

(60) Provisional application No. 62/676,036, filed on May 24, 2018, provisional application No. 62/635,153, filed on Feb. 26, 2018.

(51) Int. Cl.
*A61B 17/00*    (2006.01)
*A61B 17/34*    (2006.01)
*A61N 1/05*    (2006.01)

(52) U.S. Cl.
CPC .... *A61B 17/3468* (2013.01); *A61B 17/00234* (2013.01); *A61N 1/0541* (2013.01); *A61B 2017/00309* (2013.01)

(58) Field of Classification Search
CPC .... A61B 2017/00309; A61B 17/00234; A61B 17/3468; A61M 25/0138; A61M 25/0141;
(Continued)

(56) References Cited

U.S. PATENT DOCUMENTS

| 6,321,125 | B1 | 11/2001 | Kuzma |
| 7,966,077 | B2 | 6/2011 | Risi |

(Continued)

OTHER PUBLICATIONS

International Search Report & Written Opinion for PCT/IB2019/051546, mailed Jun. 11, 2019.

*Primary Examiner* — Majid Jamialahmadi
(74) *Attorney, Agent, or Firm* — Pilloff Passino & Cosenza LLP; Martin J. Cosenza

(57) ABSTRACT

A device, including an insertion tool including an insertion guide that is flexible in a direction lying in at least a plane lying on a longitudinal axis thereof, the insertion guide having a slit and/or a gap extending in the longitudinal direction, the plane extending through the slit and/or gap, wherein the guide configured to maintain a pre-curved electrode assembly in a substantially straight configuration while preventing the electrode assembly from twisting in response to stresses induced by bias forces which urge the assembly to return to its pre-curved configuration, when the insertion guide is flexed in the plane.

25 Claims, 63 Drawing Sheets

(58) Field of Classification Search
CPC .......... A61M 25/0144; A61M 25/0147; A61M 25/0133; A61N 1/0541
See application file for complete search history.

(56) References Cited

U.S. PATENT DOCUMENTS

| | | |
|---|---|---|
| 9,713,713 B2 | 7/2017 | Vancaillie et al. |
| 2004/0243177 A1 | 12/2004 | Svehla et al. |
| 2008/0234827 A1 | 9/2008 | Schaller et al. |
| 2014/0052148 A1 | 2/2014 | Vancaillie et al. |
| 2014/0379000 A1* | 12/2014 | Romo ............ A61B 17/29 |
| | | 606/130 |
| 2017/0105904 A1 | 4/2017 | Tatarek et al. |
| 2017/0312498 A1* | 11/2017 | Vancaillie .......... A61N 1/36036 |

* cited by examiner

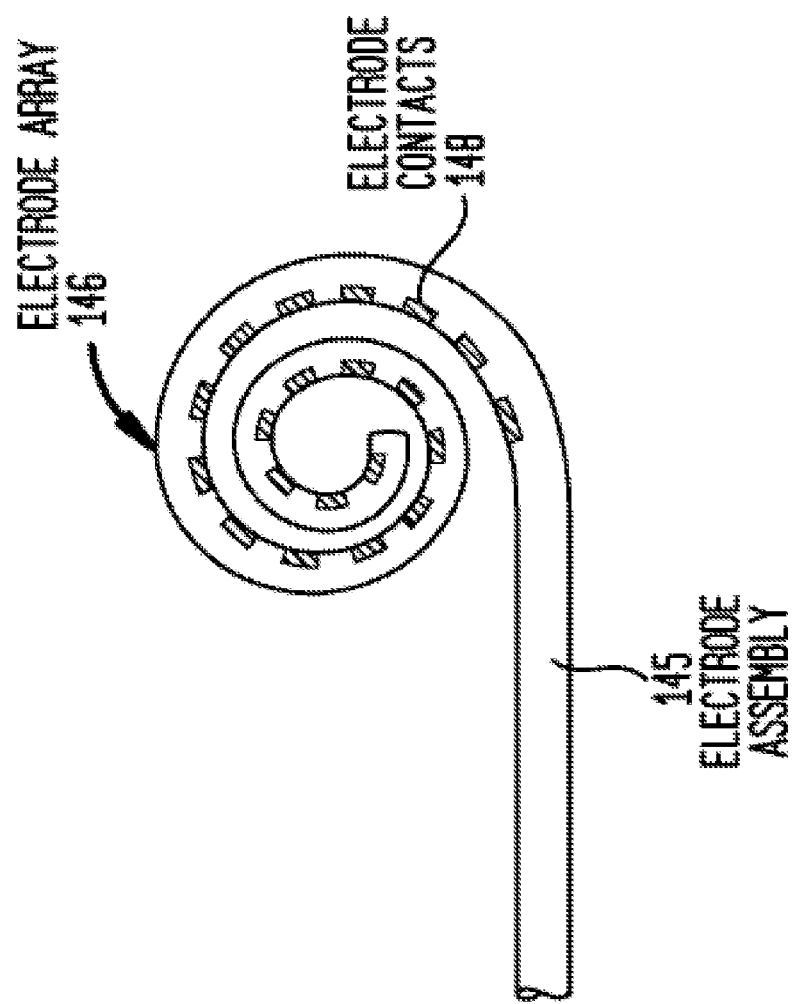

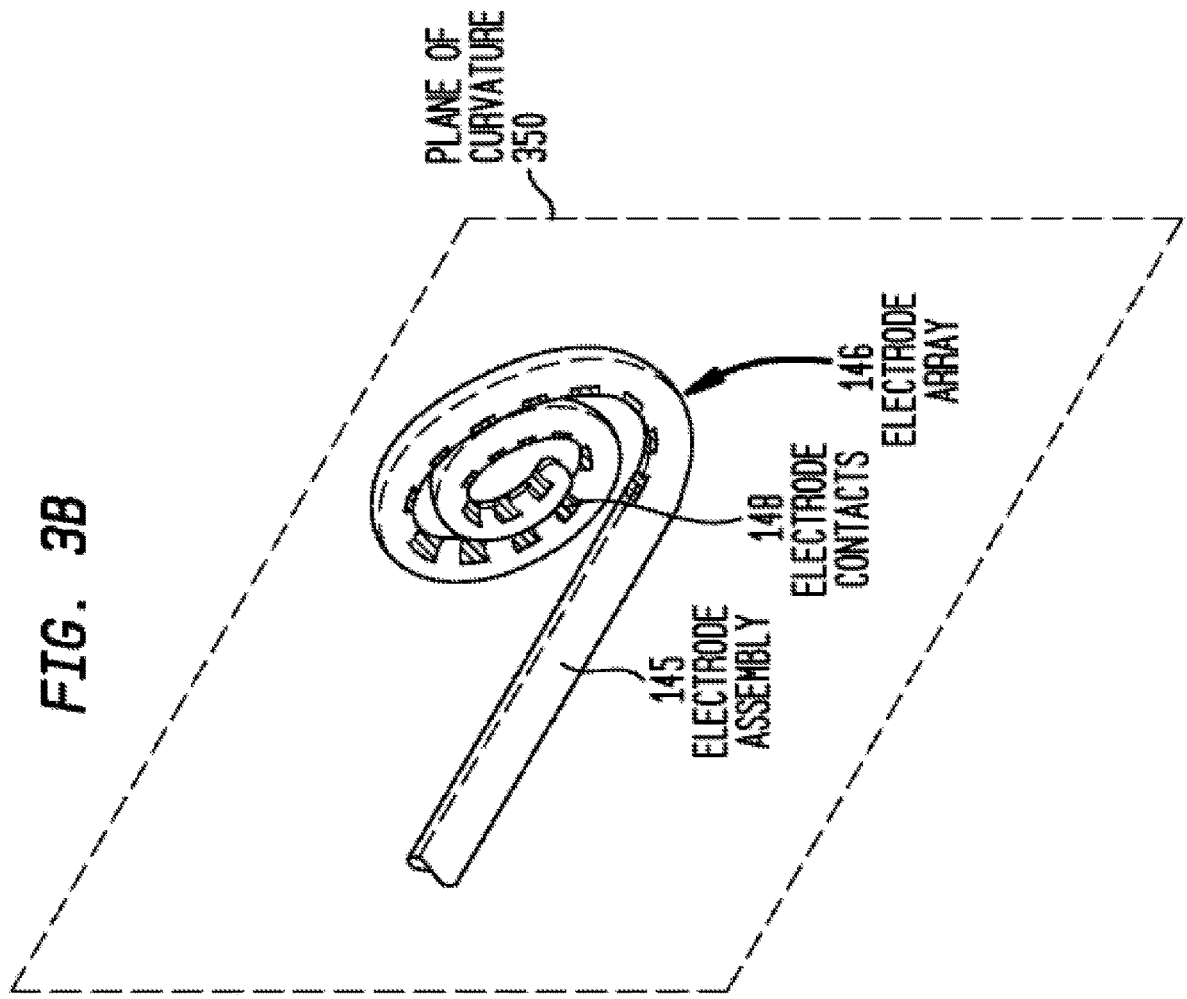

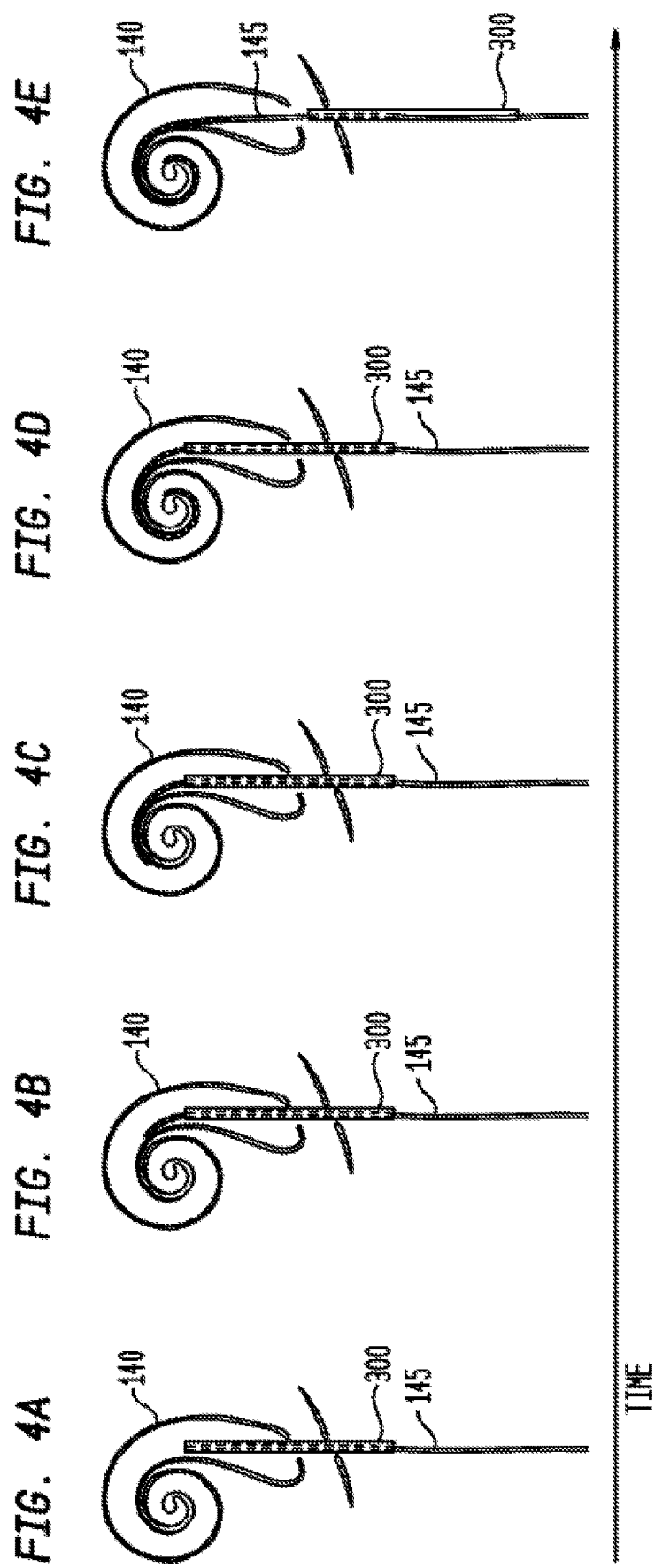

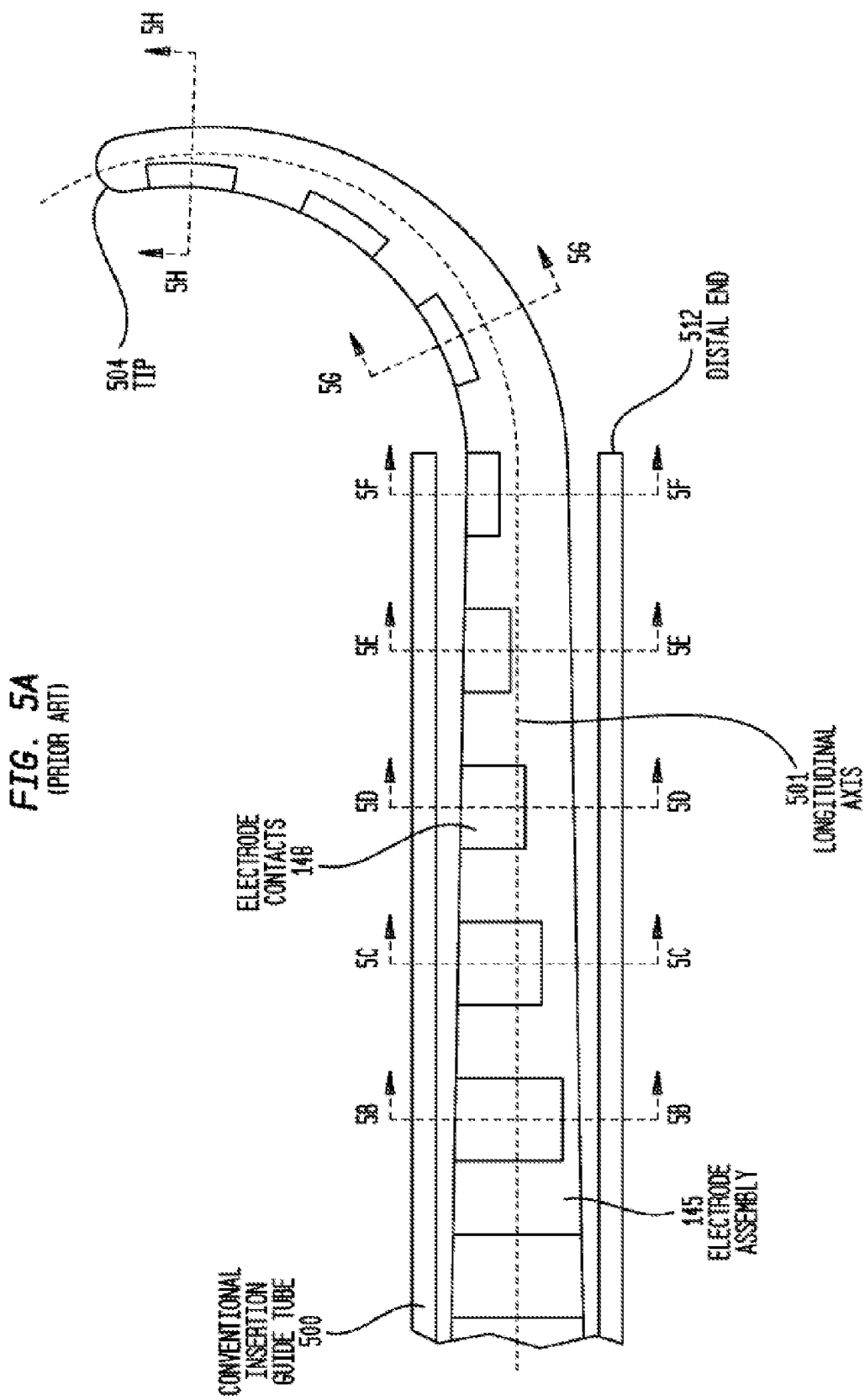

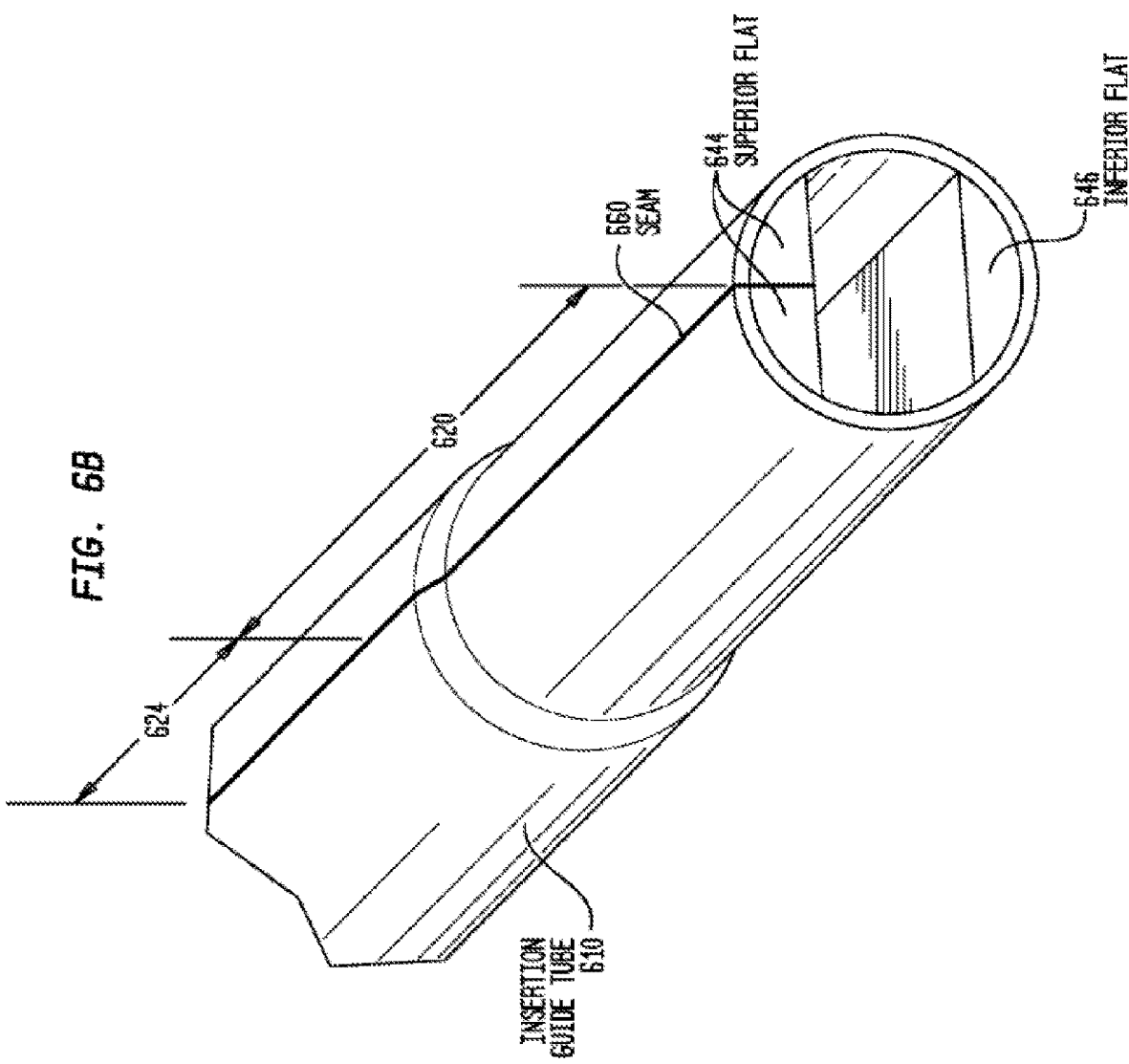

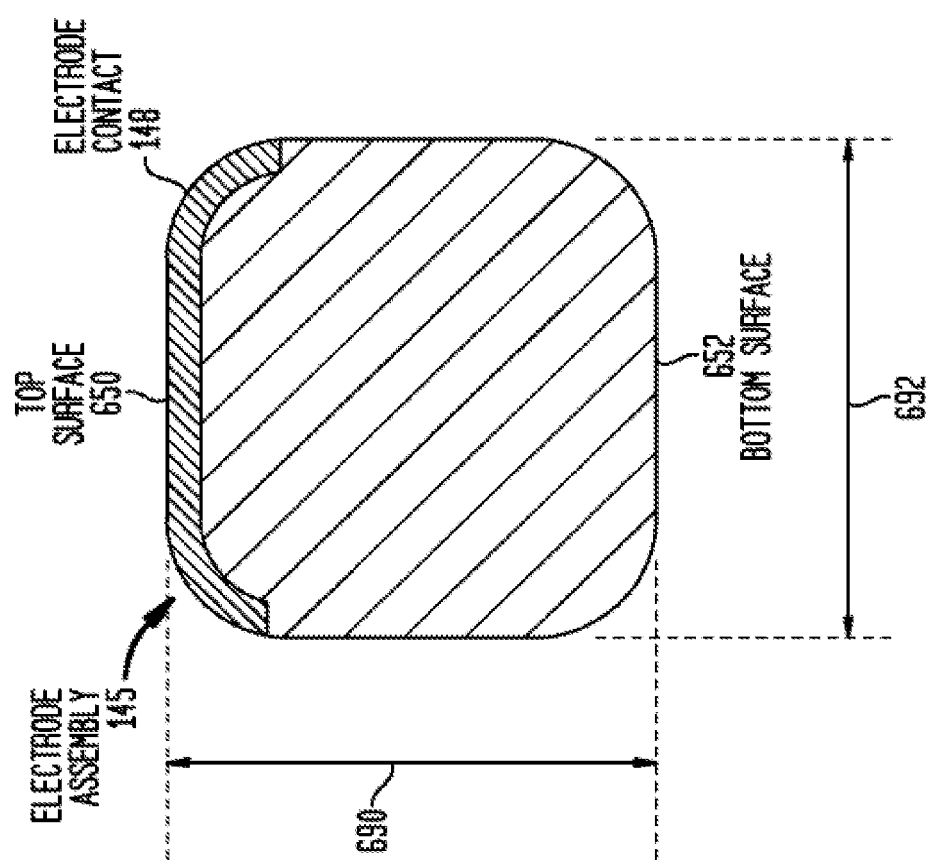

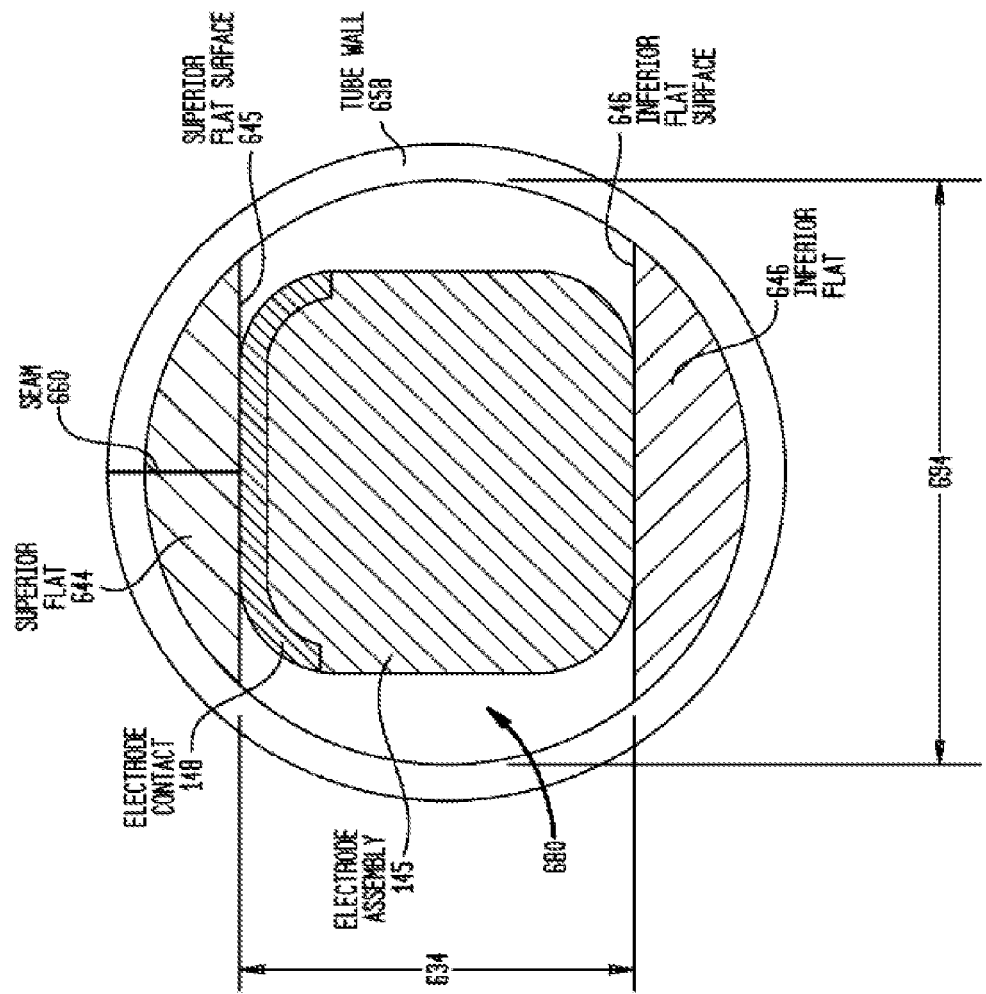

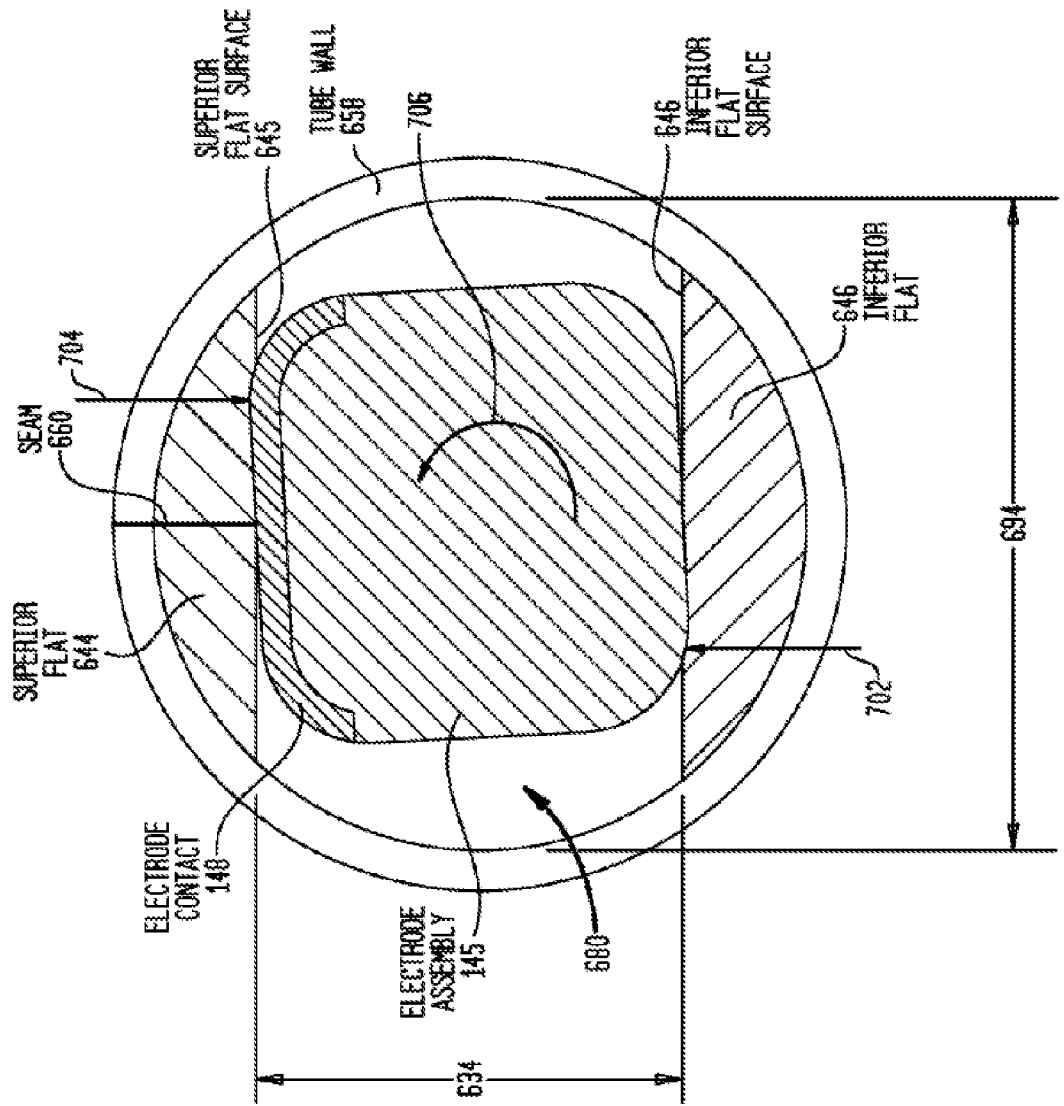

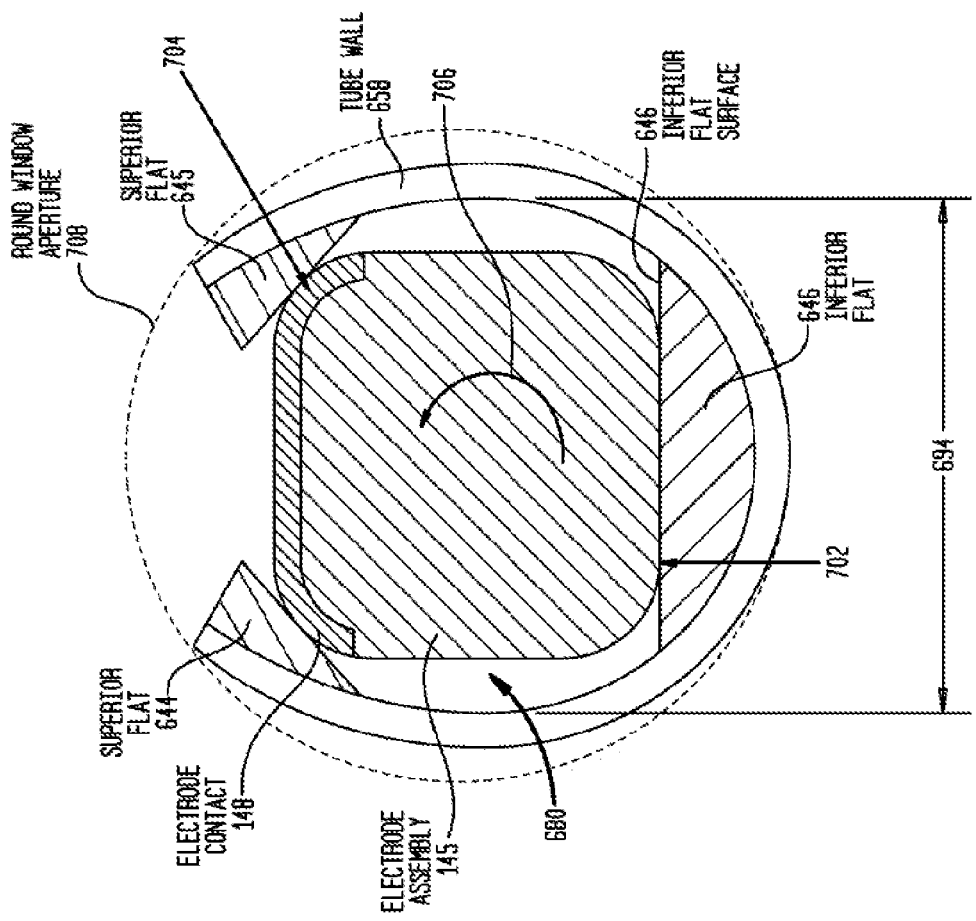

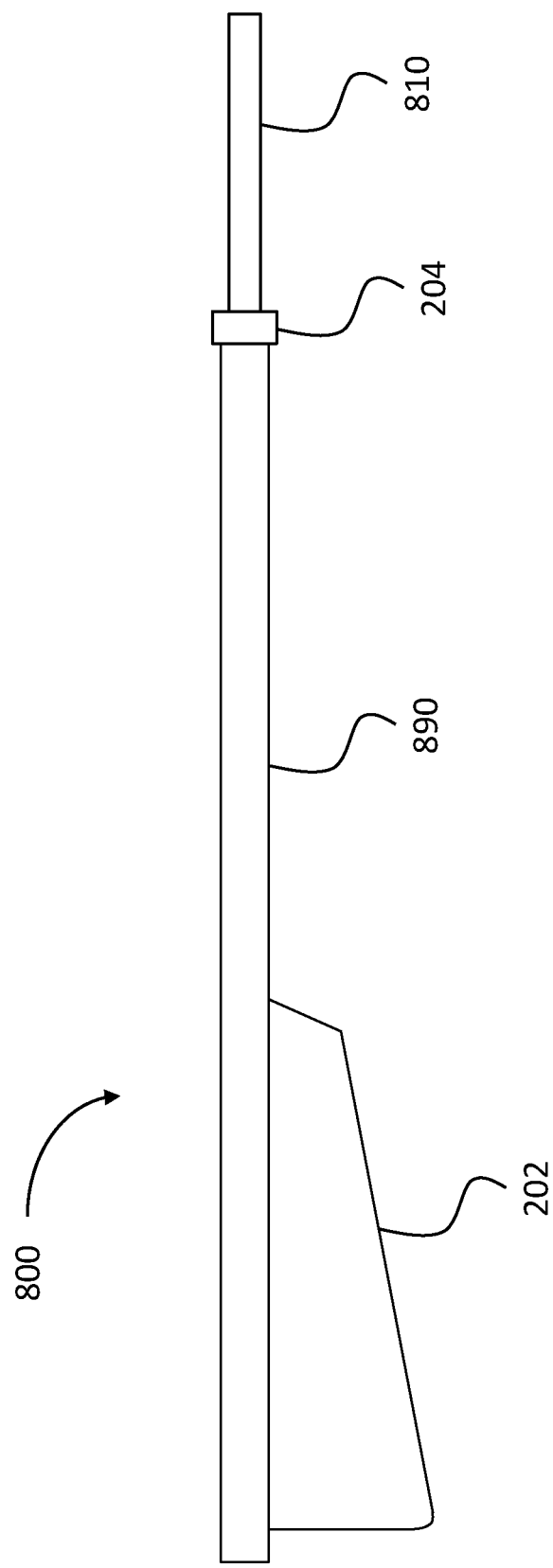

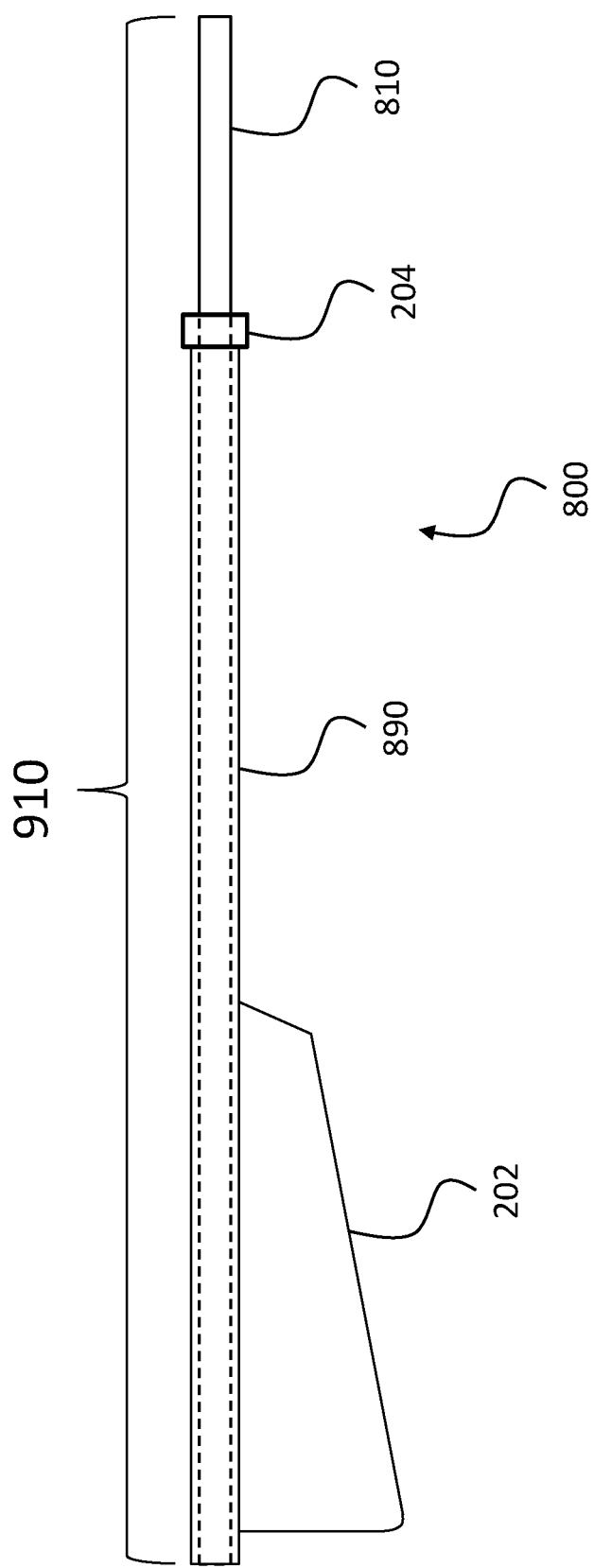

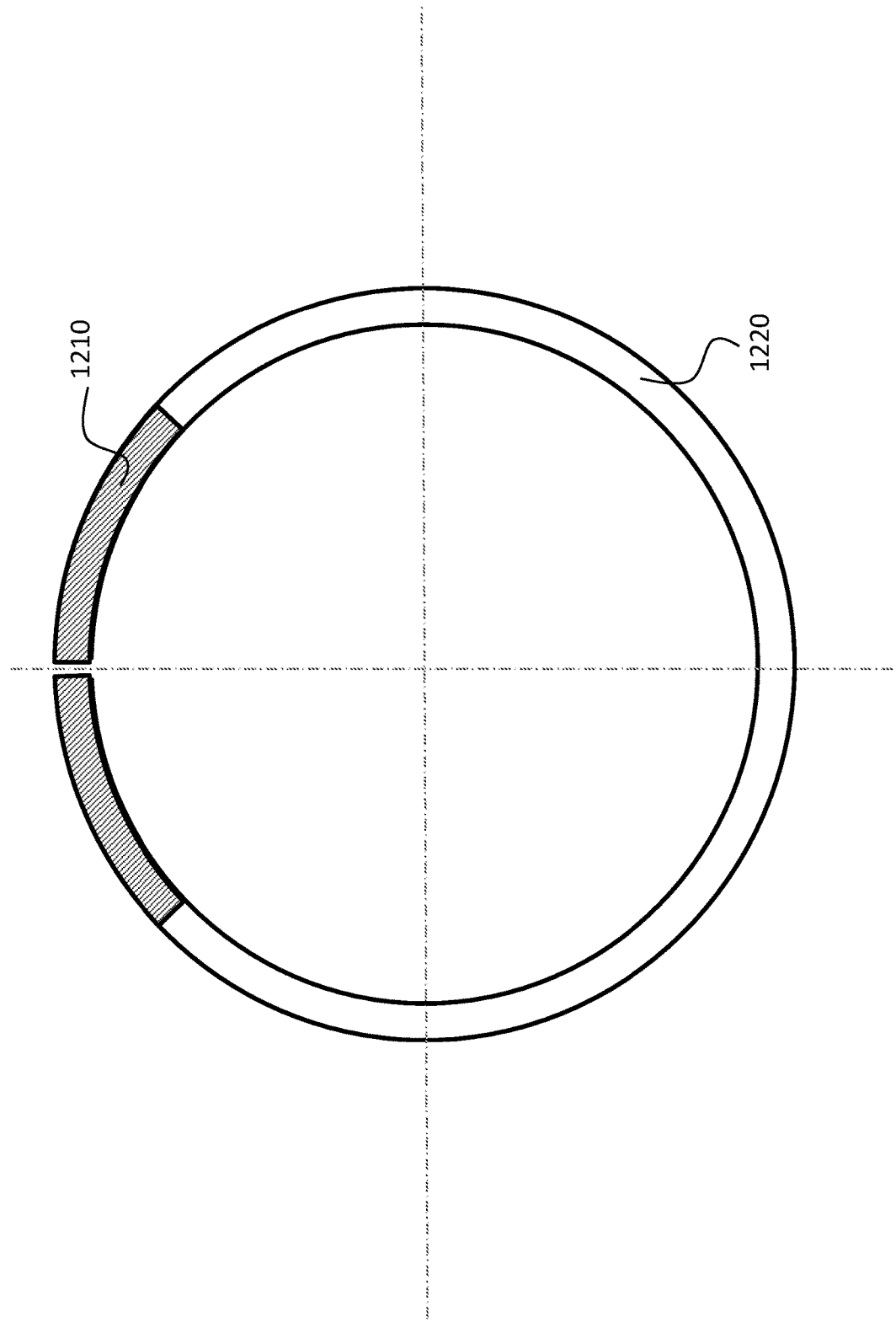

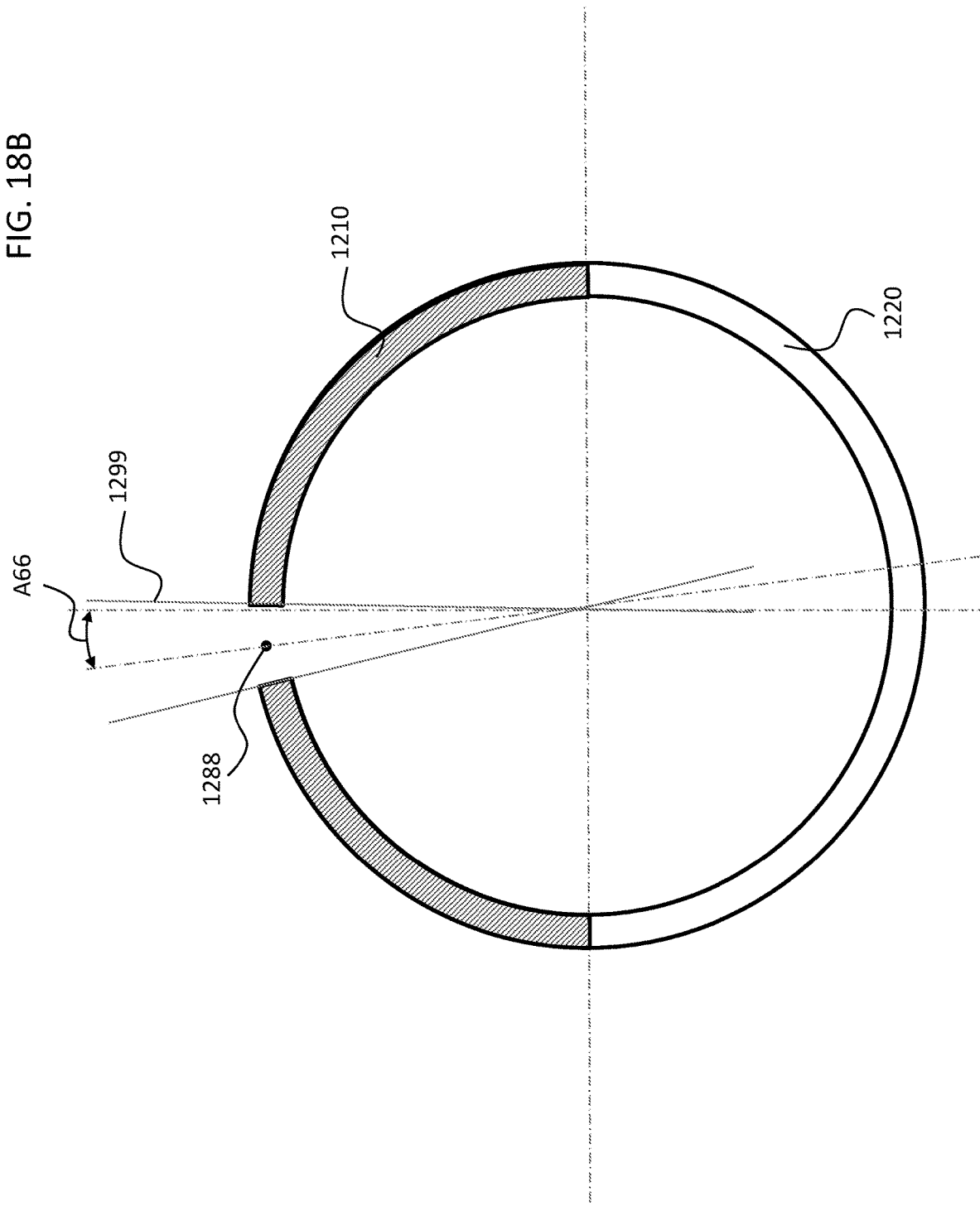

ARRAY INSERTION TOOL

CROSS-REFERENCE TO RELATED APPLICATIONS

This application claims priority to U.S. Provisional Application No. 62/635,153, filed Feb. 26, 2018, and U.S. Provisional Application No. 62/676,036, filed May 24, 2018, naming Peter Raymond SIBARY of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

It is noted that in at least some instances, there is utilitarian value to fitting a hearing prosthesis to a particular recipient. In some examples of some fitting regimes, there are methods which entail a clinician or some other professional presenting sounds to a recipient of the hearing prosthesis such that the hearing prosthesis evokes a hearing percept. Information can be obtained from the recipient regarding the character of the resulting hearing percept. Based on this information, the clinician can adjust or otherwise establish settings of the hearing prosthesis such that the hearing prosthesis operates according to these settings during normal use.

It is also noted that the electrode array of the cochlear implant generally shows utilitarian results if it is inserted in a cochlea.

SUMMARY

In accordance with an exemplary embodiment, there is a device, comprising an insertion tool including an insertion guide that is flexible in a direction lying in at least a plane lying on a longitudinal axis thereof, the insertion guide having a slit and/or a gap extending in the longitudinal direction, the plane extending through the slit and/or gap, wherein the guide configured to maintain a pre-curved electrode assembly in a substantially straight configuration while preventing the electrode assembly from twisting in response to stresses induced by bias forces which urge the assembly to return to its pre-curved configuration, when the insertion guide is flexed in the plane.

In an exemplary embodiment, there is a device, comprising an insertion tool including an elongate insertion guide that is flexible in a direction lying in at least a plane lying on a longitudinal axis thereof, wherein the device is an insertion tool for a cochlear electrode array, and the insertion guide is configured to flex in the plane such that a neutral axis is located substantially away from the longitudinal axis.

In an exemplary embodiment, there is a device, comprising an insertion tool including an elongate insertion guide having a channel through which a cochlear electrode assembly is driven to insert such into a cochlea with electrodes of the assembly aligned within the channel, wherein the insertion guide includes flats inside the channel of the insertion guide that prevent rotation of the electrode array, wherein the flats are located facing one another on opposite sides of the channel, and wherein the insertion tool is configured such that the electrodes of the electrode assembly are located equidistant from the flats when the electrode array is driven through the channel.

BRIEF DESCRIPTION OF THE DRAWINGS

Embodiments are described below with reference to the attached drawings, in which:

FIGS. 3A and 3B are side and perspective views of an electrode assembly extended out of an embodiment of an insertion sheath of the insertion guide illustrated in FIG. 2;

FIGS. 4A-4E are simplified side views depicting the position and orientation of a cochlear implant electrode assembly insertion guide tube relative to the cochlea at each of a series of successive moments during an exemplary implantation of the electrode assembly into the cochlea;

FIG. 5A is a side view of a perimodiolar electrode assembly partially extended out of a conventional insertion guide tube showing how the assembly may twist while in the guide tube;

FIG. 6B is a perspective view of the portion of the guide tube illustrated in FIG. 6A;

FIG. 6C is a cross-sectional view of a conventional electrode assembly;

FIG. 6D is a cross-sectional view of the conventional electrode assembly of FIG. 6C positioned in the insertion guide tube illustrated in FIGS. 6A and 6B;

FIG. 7A is the same image shown in FIG. 6D with arrows representing the twisting force of the electrode assembly and the reactive force applied to the electrode assembly by the insertion guide tube;

FIG. 7B is the same cross-sectional view illustrated in FIG. 7A with the insertion guide tube splayed open to accommodate a larger-dimensioned proximal region of the electrode assembly, with arrows representing the twisting force of the electrode assembly and the reactive forces applied to the electrode assembly by the insertion guide tube.

FIGS. 8 and 9 present an exemplary schematics of an exemplary insertion tool according to another embodiment;

DETAILED DESCRIPTION

Figure 1:
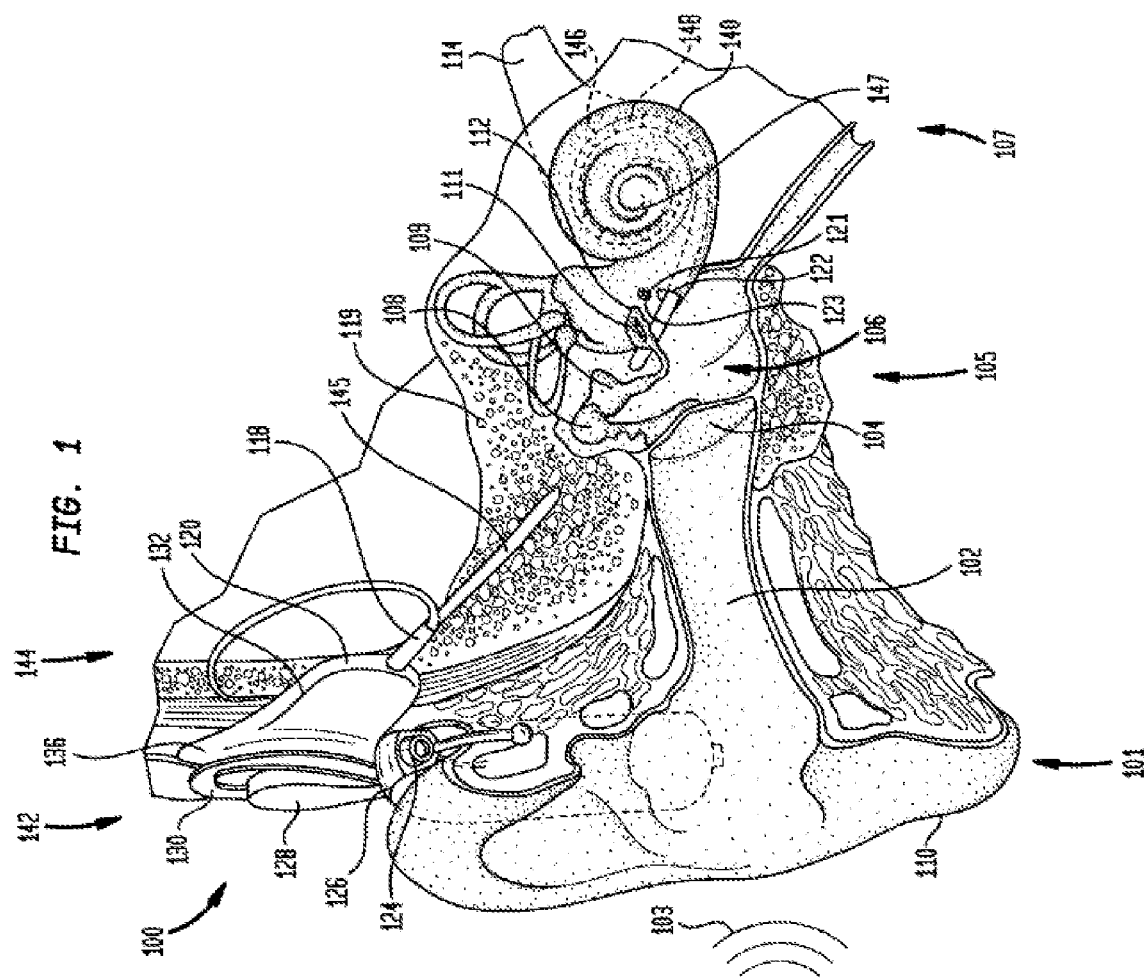
FIG. 1 is a perspective view of an exemplary hearing prosthesis in which at least some of the teachings detailed herein are applicable.

FIG. 1 is a perspective view of an exemplary cochlear implant 100 implanted in a recipient having an outer ear 101, a middle ear 105, and an inner ear 107. In a fully functional ear, outer ear 101 comprises an auricle 110 and an ear canal 102. Acoustic pressure or sound waves 103 are collected by auricle 110 and channeled into and through ear canal 102. Disposed across the distal end of ear canal 102 is a tympanic membrane 104 that vibrates in response to sound waves 103. This vibration is coupled to oval window or fenestra ovalis 112 through the three bones of the middle ear 105, collectively referred to as the ossicles 106, and comprising the malleus 108, the incus 109, and the stapes 111. Ossicles 106 filter and amplify the vibrations delivered by tympanic membrane 104, causing oval window 112 to articulate, or vibrate. This vibration sets up waves of fluid motion of the perilymph within cochlea 140. Such fluid motion, in turn, activates hair cells (not shown) inside the cochlea which in turn causes nerve impulses to be generated which are transferred through spiral ganglion cells (not shown) and auditory nerve 114 to the brain (also not shown) where they are perceived as sound.

The exemplary cochlear implant illustrated in FIG. 1 is a partially implanted stimulating medical device. Specifically, cochlear implant 100 comprises external components 142 attached to the body of the recipient, and internal or implantable components 144 implanted in the recipient. External components 142 typically comprise one or more sound input elements for detecting sound, such as microphone 124, a sound processor (not shown), and a power source (not shown). Collectively, these components are housed in a behind-the-ear (BTE) device 126 in the example depicted in FIG. 1. External components 142 also include a transmitter unit 128 comprising an external coil 130 of a transcutaneous energy transfer (TET) system. Sound processor 126 processes the output of microphone 124 and generates encoded stimulation data signals which are provided to external coil 130.

Internal components 144 comprise an internal receiver unit 132 including a coil 136 of the TET system, a stimulator unit 120, and an elongate stimulating lead assembly 118. Internal receiver unit 132 and stimulator unit 120 are hermetically sealed within a biocompatible housing commonly referred to as a stimulator/receiver unit. Internal coil 136 of receiver unit 132 receives power and stimulation data from external coil 130. Stimulating lead assembly 118 has a proximal end connected to stimulator unit 120, and extends through mastoid bone 119. Lead assembly 118 has a distal region, referred to as electrode assembly 145, a portion of which is implanted in cochlea 140.

Electrode assembly 145 can be inserted into cochlea 140 via a cochleostomy 122, or through round window 121, oval window 112, promontory 123, or an opening in an apical turn 147 of cochlea 140. Integrated in electrode assembly 145 is an array 146 of longitudinally-aligned and distally extending electrode contacts 148 for stimulating the cochlea by delivering electrical, optical, or some other form of energy. Stimulator unit 120 generates stimulation signals each of which is delivered by a specific electrode contact 148 to cochlea 140, thereby stimulating auditory nerve 114.

Figure 2:
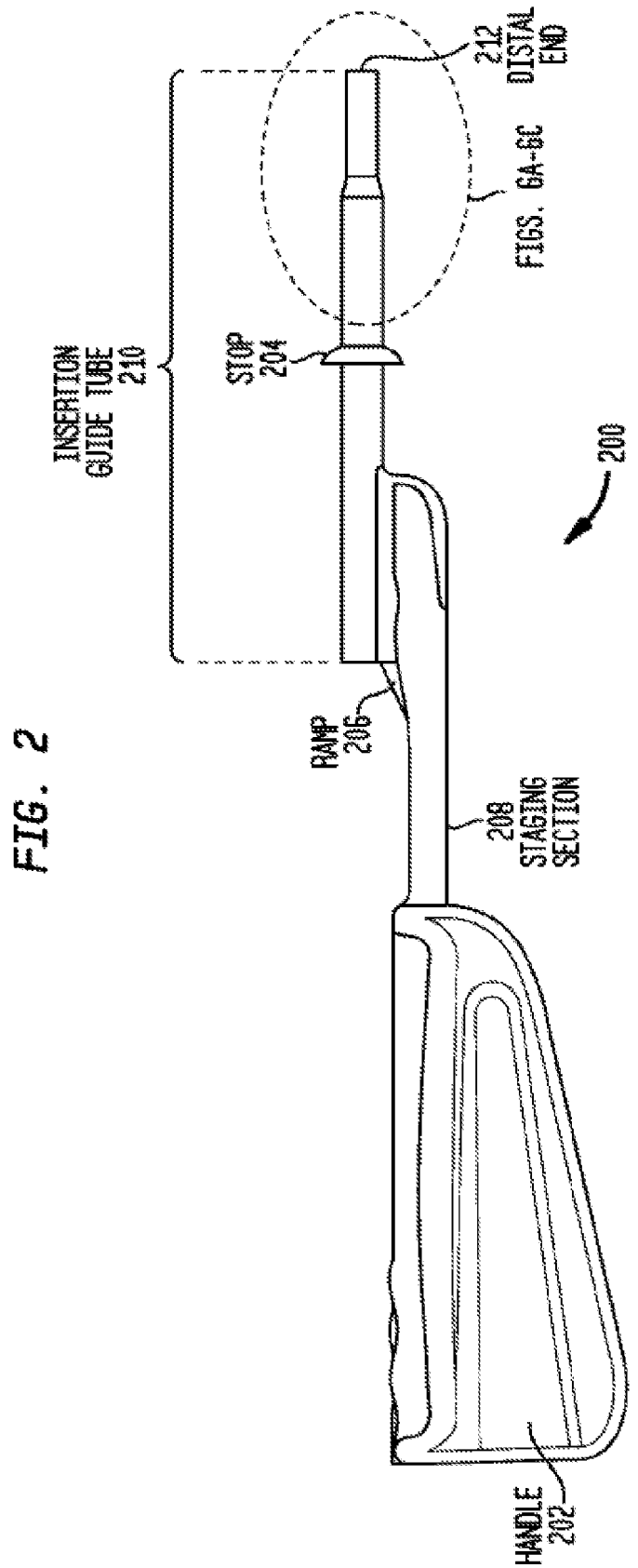
FIG. 2 is a side view of an embodiment of an insertion guide for implanting a cochlear implant electrode assembly such as the electrode assembly illustrated in FIG. 1.

Electrode assembly 145 may be inserted into cochlea 140 with the use of an insertion tool. FIG. 2 is a side view of an embodiment of an insertion tool for implanting an elongate electrode assembly generally represented by electrode assembly 145 into a mammalian cochlea, represented by cochlea 140. The illustrative insertion tool, referred to herein as insertion tool 200, includes an elongate insertion guide tube 210 configured to be inserted into cochlea 140 and having a distal end 212 from which an electrode assembly is deployed. Insertion guide tube 210 has a radially-extending stop 204 that may be utilized to determine or otherwise control the depth to which insertion guide tube 210 is inserted into cochlea 140.

Insertion guide tube 210 is mounted on a distal region of an elongate staging section 208 on which the electrode assembly is positioned prior to implantation. A handle 202 is attached to the staging section 208, to be gripped by fingers and/or tweezers, etc. in some embodiments, instead of a handle, a robotic arm adapter is mounted to a proximal end of staging section 208 to facilitate attachment of the guide to a robot, which adapter includes through holes through which bolts can be passed so as to bolt the guide 200 to a robotic arm.

During use, electrode assembly 145 is advanced from staging section 208 to insertion guide tube 210 via ramp 206. After insertion guide tube 210 is inserted to the appropriate depth in cochlea 140, electrode assembly 145 is advanced through the guide tube to exit distal end 212 as described further below.

FIGS. 3A and 3B are side and perspective views, respectively, of representative electrode assembly 145. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve, so that it is able to conform to the curved interior of cochlea 140. As shown in FIG. 3B, when not in cochlea 140, electrode assembly 145 generally resides in a plane 350 as it returns to its curved configuration. That said, it is noted that embodiments of the insertion guides detailed herein and/or variations thereof can be applicable to a so-called straight electrode array, which electrode array does not curl after being free of a stylet or insertion guide tube etc., but instead remains straight FIGS. 4A-4E are a series of side-views showing consecutive exemplary events that occur in an exemplary implantation of electrode assembly 145 into cochlea 140. Initially, electrode assembly 145 and insertion guide tube 310 are assembled. For example, electrode assembly 145 is inserted (slidingly or otherwise) into a lumen of insertion guide tube 300. The combined arrangement is then inserted to a predetermined depth into cochlea 140, as illustrated in FIG. 4A. Typically, such an introduction to cochlea 140 is achieved via cochleostomy 122 (FIG. 1) or through round window 121 or oval window 112. In the exemplary implantation shown in FIG. 4A, the combined arrangement of electrode assembly 145 and insertion guide tube 300 is inserted to approximately the first turn of cochlea 140.

As shown in FIG. 4A, the combined arrangement of insertion guide tube 300 and electrode assembly 145 is substantially straight. This is due in part to the rigidity of insertion guide tube 300 relative to the bias force applied to the interior wall of the guide tube by pre-curved electrode assembly 145. This prevents insertion guide tube 300 from bending or curving in response to forces applied by electrode assembly 145, thus enabling the electrode assembly to be held straight, as will be detailed below.

As noted, electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly from returning to its pre-curved configuration. This induces stress in electrode assembly 145. Pre-curved electrode assembly 145 will tend to twist in insertion guide tube 300 to reduce the induced stress. In the embodiment configured to be implanted in scala tympani of the cochlea, electrode assembly 145 is pre-curved to have a radius of curvature that approximates the curvature of medial side of the scala tympani of the cochlea. Such embodiments of the electrode assembly are referred to as a perimodiolar electrode assembly, and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

Conventional insertion guide tubes typically have a lumen dimensioned to allow the entire tapered electrode assembly to travel through the guide tube. Because the guide tube is able to receive the relatively larger proximal region of the electrode assembly, there will be a gap between the relatively smaller distal region of the electrode assembly and the guide tube lumen wall. Such a gap allows the distal region of the electrode assembly to curve slightly until the assembly can no longer curve due to the lumen wall.

Returning to FIGS. 3A-3B, perimodiolar electrode assembly 145 is pre-curved in a direction that results in electrode contacts 148 being located on the interior of the curved assembly, as this causes the electrode contacts to face the modiolus when the electrode assembly is implanted in or adjacent to cochlea 140. As seen in FIG. 5A, insertion guide tube 500 retains electrode assembly 145 in a substantially straight configuration, thereby preventing the assembly from taking on the configuration shown in FIG. 3B. The inability of electrode assembly 145 to curve to accommodate the bias force induces stress in the assembly. Pre-curved electrode assembly 145 will tend to twist while exiting insertion guide tube 510 to reduce this stress. With the distal end of the electrode assembly curved to abut the lumen wall, the assembly twists proximally.

Figure 5E:
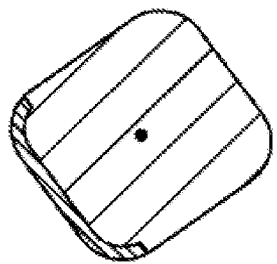
FIGS. 5B-5I are cross-sectional views of the electrode assembly illustrated in FIG. 5A.
Figure 5D:
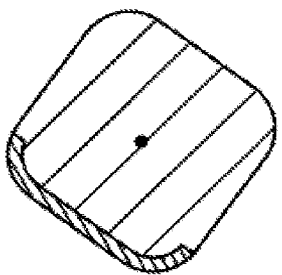
Figure 5C:
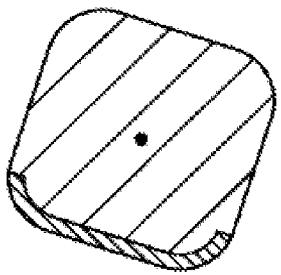
Figure 5B:
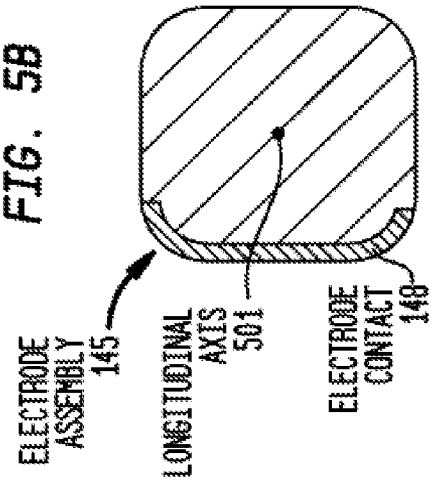
Figure 5I:
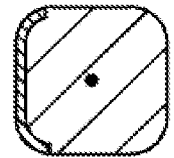
Figure 5H:
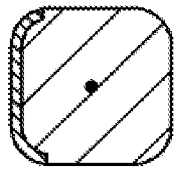
Figure 5G:
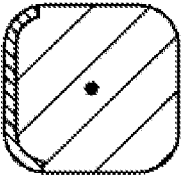
Figure 5F:
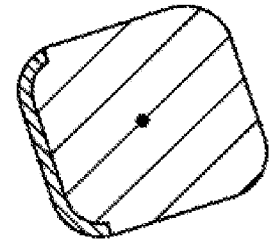

This is illustrated in FIGS. 5A-5I. FIG. 5A is a side view of perimodiolar electrode assembly 145 partially extended out of a conventional insertion guide tube 500, showing how the assembly may twist while in the guide tube. FIGS. 5B-5F are cross-sectional views taken through respective sections 5B-5B, 5C-5C, 5D-5D, 5E-5E, and 5F-5F of electrode assembly 145 in FIG. 5A.

As shown in FIGS. 5A-5F, the portion of electrode assembly 145 in insertion guide tube 510 is twisted about its longitudinal axis, resulting in electrode contacts 148 in the twisted region to have a different radial position relative to insertion guide tube 510. As shown in FIGS. 5A and 5G-I, as electrode assembly 145 exists insertion guide tube 500, the assembly is free to curve in accordance with its bias force. However, the orientation of electrode contacts in the deployed region of the assembly is adversely affected by the twisted region of the assembly remaining in guide tube 510.

Figure 6A:
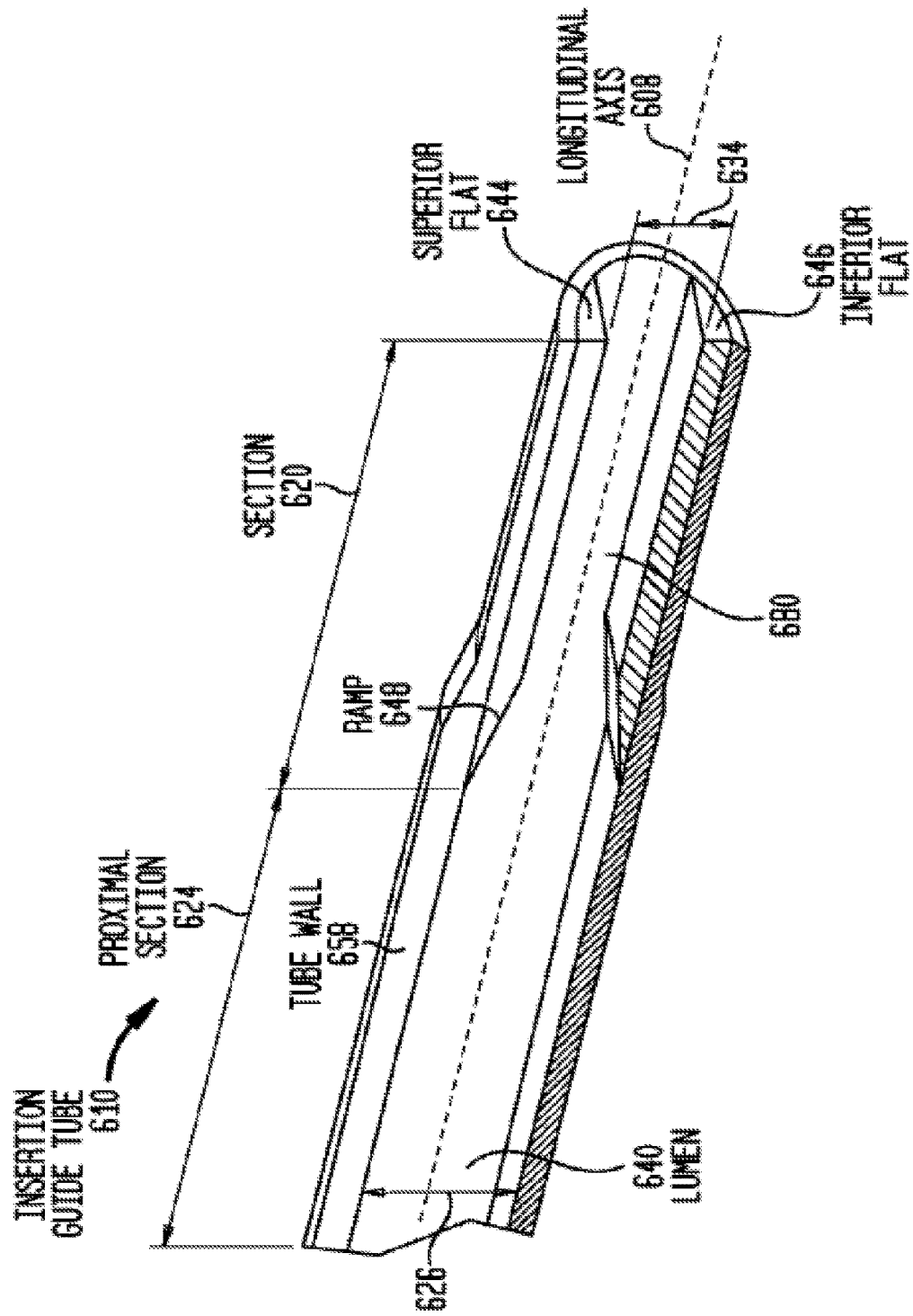
FIG. 6A is a cross-sectional view of an embodiment of the insertion guide tube.

FIGS. 6A-6D are different views of an insertion guide tube 210, referred to herein at insertion guide tube 610. For ease of description, features of the guide tube will be described with reference to the orientation of the guide tube illustrated in the figures. FIG. 6A is a partial cross-sectional view of an embodiment of insertion guide tube 210, referred to herein at insertion guide tube 610. As can be seen, insertion guide tube 610 includes a section 620 formed at the distal end of the guide tube. Section 620 is contiguous with the remaining part of guide tube 610. Guide tube 610 has a lumen 640 which, in proximal section 624 has a vertical dimension 626, and a distal section 620 has a smaller vertical dimension 634 described below. The vertical dimension of lumen 640 decreases from dimension 626 to dimension 634 due to a ramp 648 at the proximal end of section 642.

As shown in FIG. 6C, electrode assembly 145 has a rectangular cross-sectional shape, with the surface formed in part by the surface of the electrode contact, referred to herein as top surface 650, and the opposing surface, referred to herein as bottom surface 652, are substantially planar. These substantially planar surfaces are utilized in embodiments of the insertion guide tube described herein.

Tube wall 658 in section 620 has surfaces 644 and 646 which extend radially inward to form a guide channel 680. Specifically, a superior flat 644 provides a substantially planar lumen surface along the length of section 620. As shown in FIGS. 6A, 6B, and 6D, superior flat 644 has a surface that is substantially planar and which therefore conforms with the substantially planar top surface 650 of electrode assembly 145. Similarly, inferior flat 646 has a surface that is substantially planar which conforms with the substantially planar bottom surface 652 of electrode assembly 145. As shown in FIG. 6D, when a distal region of electrode assembly 145 is located in section 620, the surfaces of superior flat 644 and inferior flat 646 are in physical contact with top surface 650 and bottom surface 652, respectively, of the electrode assembly.

As noted, electrode assemblies are longitudinally tapered to accommodate the increasingly larger cross-sectional dimensions of an electrode assembly 145 as it passes through guide channel 680, insertion guide tube 610 has a longitudinal seam 660 as shown in FIGS. 6A, 6B, 6D, 7A, and 7B. This seam enables insertion tube 610 to splay open as shown in FIG. 7B. Specifically, insertion tube 610 opens as the vertical distance 690 from bottom surface 652 to top surface 650 of the portion of the assembly in guide channel 680 becomes greater than the vertical distance 634 between the surfaces of inferior flat 646 and superior flat 644.

Once electrode assembly 145 is inserted into cochlea 140, insertion guide tube 610 is retracted over electrode assembly 145. The expanded insertion guide tube 610 is to be withdrawn from cochlea 140 and therefore is to pass through the cochleostomy, oval or round window. In a round window insertion, for example, splayed insertion guide tube 610 is to pass through round window aperture 708.

As electrode assembly 145 is advanced through insertion guide tube 610, the tendency of the assembly to twist decreases. This is due to the increasingly greater portion of the electrode assembly which has been deployed, the relatively larger dimensions of the proximal regions of the assembly, and the relatively smaller bias force in the proximal region as compared to the distal region of the assembly. Thus, as the cross-sectional size of the assembly passing through guide channel 680 increases, the tendency of the electrode assembly to twist decreases. Referring again to FIG. 7B, as insertion guide tube 610 splays, the halves of bifurcated superior flat 348 each translate laterally to the corners of the electrode assembly, and ultimately to opposing sides of the assembly. And as noted, the outside diameter of insertion guide tube 610 does not exceed threshold value(s) which facilitate the withdrawal of the guide tube. In the example noted above with reference to FIGS. 7A and 7B, for example, insertion guide tube 610 has a diameter that is less than the round window aperture 708 when the guide tube is and is not splayed.

As shown in FIG. 6D, lumen 640 has a lateral dimension or width 694 which is greater than the analogous lateral dimension or width 692 of the distal region of electrode assembly 145. This space is dimensioned to receive the wider electrode assembly as the larger proximal region passes through guide channel 680. This is described in greater detail below.

In section 620 there is a minimal gap, if any, between flats 644, 646 and electrode assembly 145.

In an exemplary embodiment, insertion guide tube 610 is made of polyimide, and the flats comprise silicone molded in the tube. Other materials can be utilized in other embodiments. In some embodiments, the flats and guide tube are unitary.

Accordingly, some embodiments detailed herein and/or variations thereof are directed towards an insertion guide having an insertion guide tube that maintains a perimodiolar or other pre-curved electrode assembly in a substantially straight configuration while preventing the electrode assembly from twisting in response to stresses induced by the bias force which urges the assembly to return to its pre-curved configuration. This can be utilitarian in that such can improve the likelihood that when the electrode assembly is deployed from the distal end of the insertion guide tube, the electrode assembly and insertion guide tube have a known relative orientation.

Figure 10:
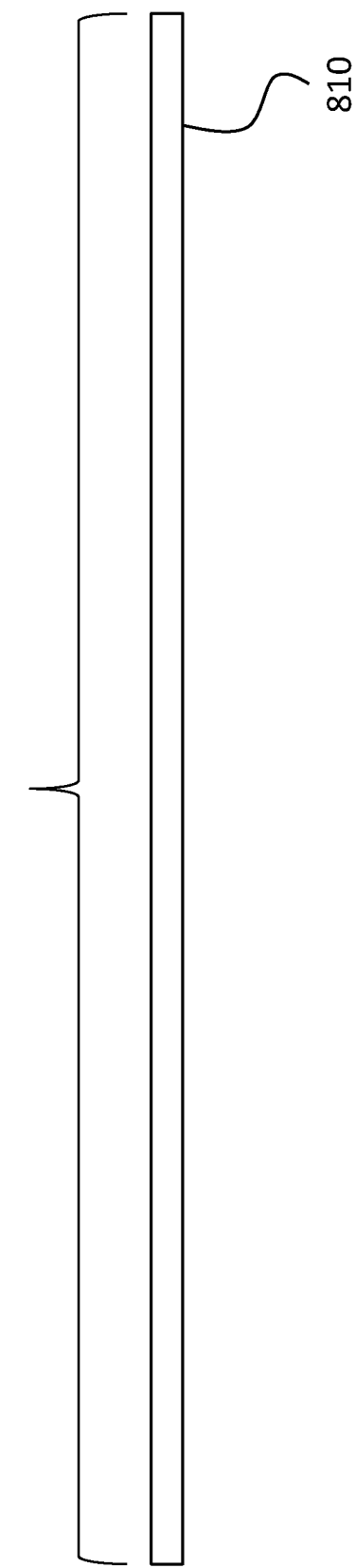
FIGS. 10-17G present exemplary schematics of features of exemplary insertion tools according to some embodiments.
Figure 11A:
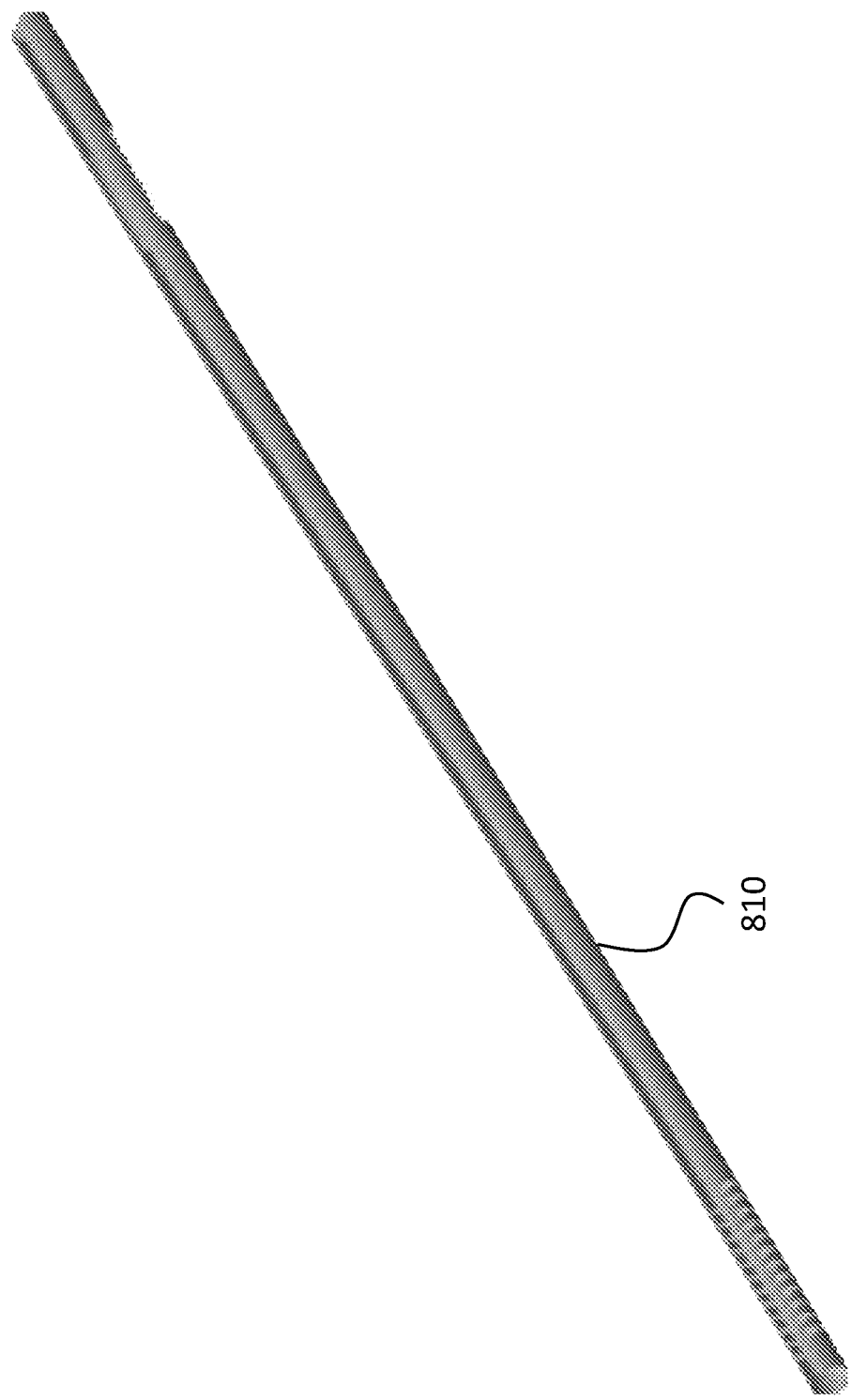
Figure 11B:
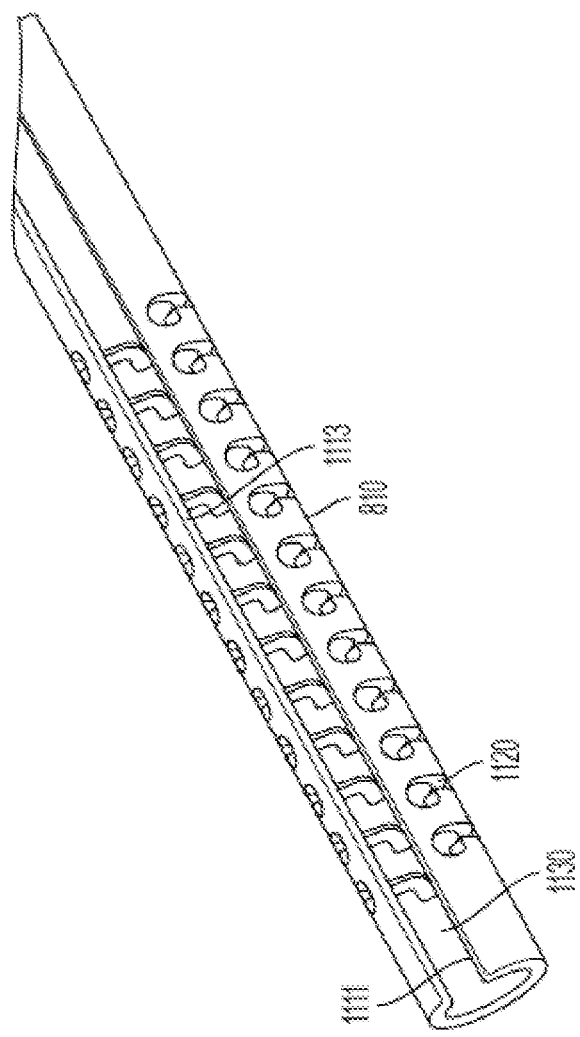
Figure 11C:
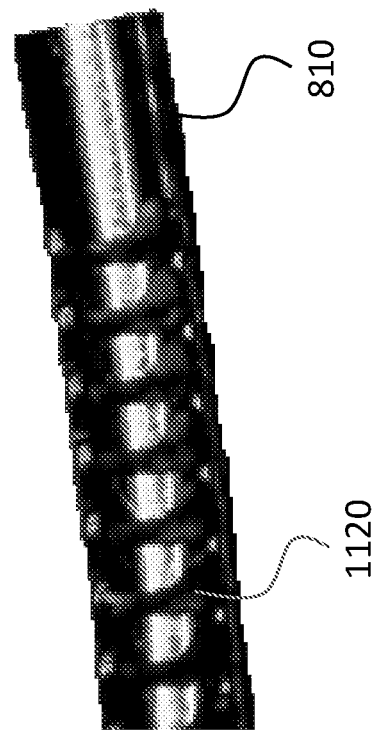
Figure 11D:
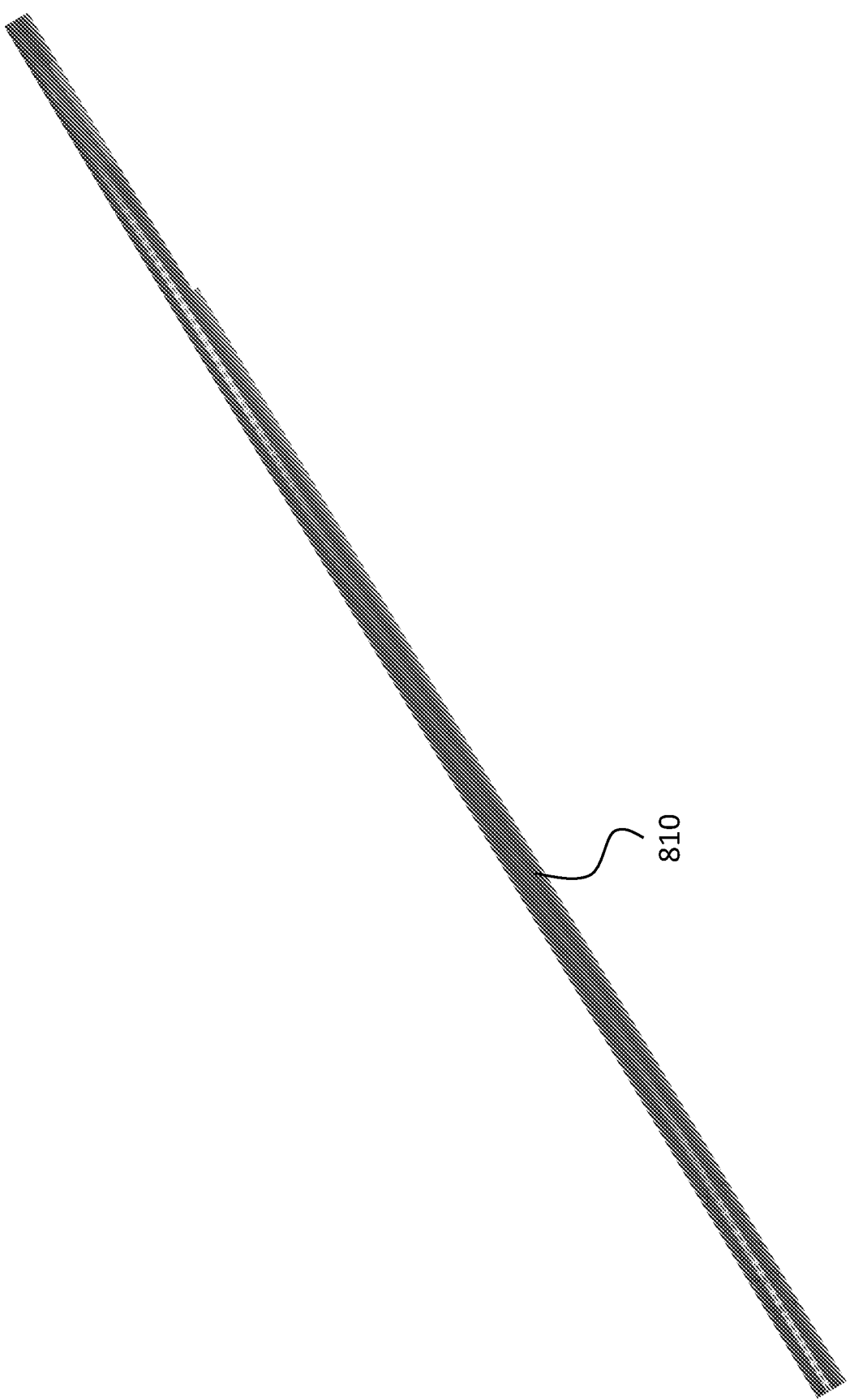
Figure 11E:
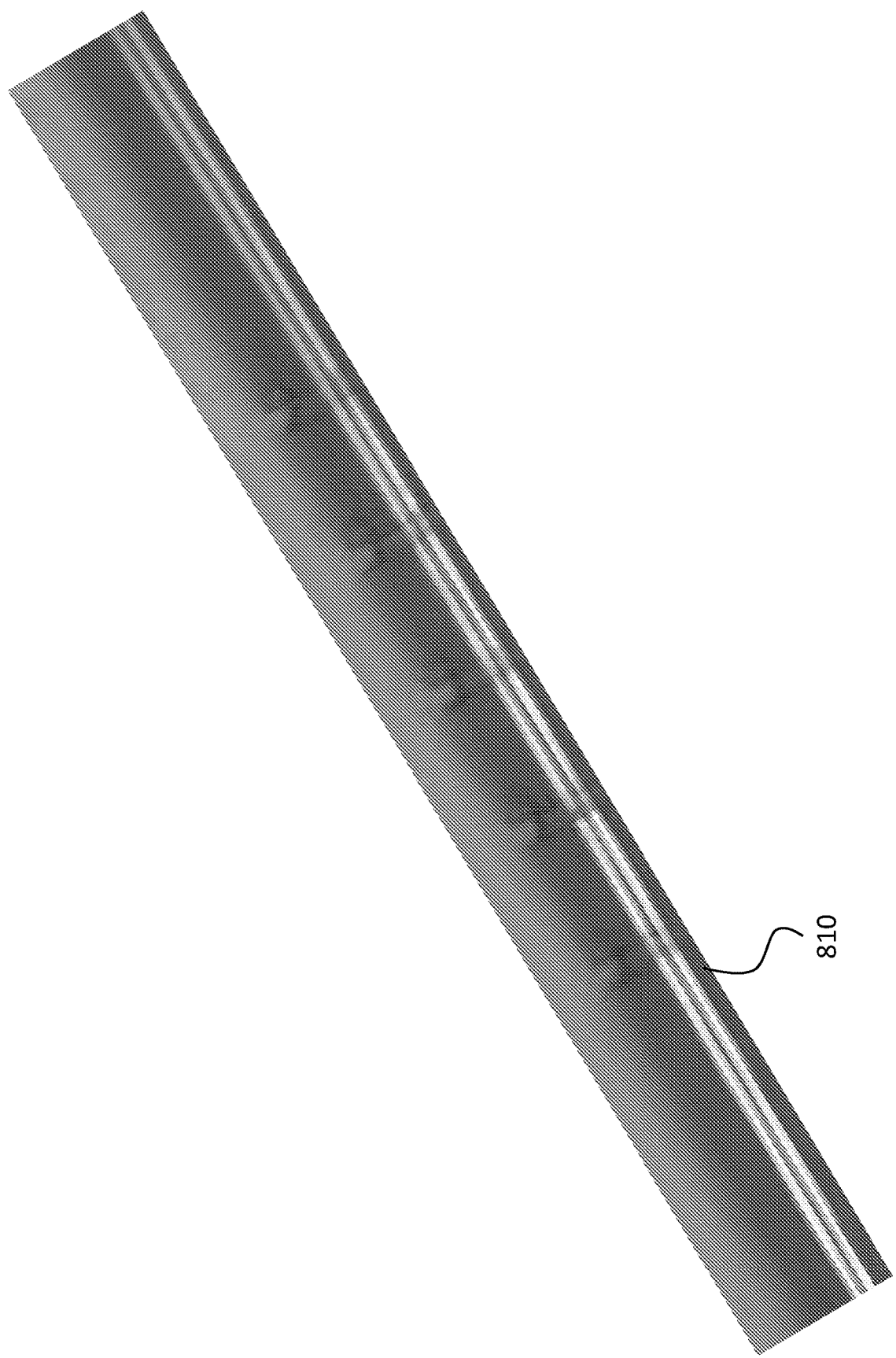

FIG. 8 presents another exemplary embodiment of an insertion tool, insertion tool 800. Like reference numbers from the embodiment above will be utilized in some instances, and the use of like reference numbers thus corresponds to a disclosure of structure and/or functionality corresponding to that detailed above unless otherwise specified. An insertion guide 810, which can be a tube or another structure, such as a rib and spine configuration, etc., as will be described below, extends past the stop 204, and a proximal portion thereof is located in support body 890, which can be a polymer tube or the like through which the guide 810 extends. FIG. 9 shows, in dashed line format, guide 810 extending into the support body 890, with reference 910 showing the extent of the guide 810. FIG. 10 depicts the guide 810 in free space without any of the other structure of the insertion tool 800 depicted. FIGS. 11A and 11D are isometric views of the guide 810, where the bottom left tip of the guide 810 corresponds to the distal end of the guide 810 seen in FIG. 8 (the part that sticks out past the support body). FIG. 11B depicts a close-up view of the distal and of the guide 810, showing a plurality of openings 1120 that extend from outside the guide all the way to the inside of the guide. In an exemplary embodiment, these are slits, while in other embodiments, these are gaps. FIG. 11E depicts a close up view of the distal end of the embodiment of FIG. 11D.

FIG. 11B also depicts the gap 1130 that extends along the longitudinal axis of the guide tube 810. In an alternative embodiment, the gap 1130 is instead a slit. In some embodiments, the slit widens to form a gap and/or vice versa. FIG. 11C depicts an exemplary section of the guide tube looking from the side opposite of the gap 1130. As can be seen, the openings 1120 extend from one side of the guide to the other side of the guide with respect to the bottom of the guide (the side opposite the slit/gap—hereinafter, when the phrase top of the guide is utilized, such corresponds to the side of the guide that has the slits and/or gap and/or the side of the guide that is closest to the top of the electrodes when the electrode array is inserted therein, and when the phrase bottom of the guide is utilized, such corresponds to the side of the guide that is opposite the slits and/or gap and/or the side of the guide that is furthest from the top of the electrodes when the electrode array is inserted therein).

Thus, in an exemplary embodiment, the guide is partially segmented at a plurality of locations that extend about the longitudinal axis and extend through the plane only on one side of the longitudinal axis (e.g., the locations of the segments do not reach the longitudinal gap/slit). In an exemplary embodiment, the guide includes a slit and/or a gap extending parallel to the longitudinal axis and guide is partially segmented at a plurality of locations that extend about the longitudinal axis and no segments that extend about the longitudinal axis extend to the gap and/or slit.

In an exemplary embodiment, the surfaces that form the slit and/or gap that extends parallel to the longitudinal axis all lie on respective planes. FIG. 11B depicts surfaces 1113 and 1111, which surfaces extend on respective planes. The slit and/or gap has a contiguous surface that is flat from the beginning of the guide to the end of the guide or at least from the distal end of the guide to a location of the guide at the stop. In an exemplary embodiment, the two planes are parallel to one another, while in other embodiments, planes are obliquely angled relative to one another. More on this below. In an exemplary embodiment, the surface(s) are such that the one or both surfaces extend such that respective paths exists for least 20, 25, 30, 35, 40, 45, 50, 55, 60, 65, 70, 75, 80, 85, 90, 95 or 100% of the entire length of the tube that lie on the same plane(s).

In an exemplary embodiment, the respective surfaces that establish the longitudinal extending sides of the slit and/or gap are continuous surfaces (concomitant with embodiments where the openings do not cross the slit/gap). This is as opposed to an embodiment where the openings cross the slit and/or gap, in which case the respective surfaces that establish the longitudinal extending sides of the slit and/or gap are not continuous surfaces, but instead are surfaces that are divided. Indeed, where the openings extend to the slit and/or gap, the respective surfaces that establish the longitudinal sides are divided and are not contiguous with each other. This is as opposed to the embodiments where the openings do not extend to the slits and/or gap, where the longitudinal sides of the slits are one surface, and can be characterized by plurality of sub-units that are all contiguous with each other (i.e., a given longitudinal side has a total surface area, and if that service area was arbitrarily divided up into subunits, the various subunits would be contiguous with each other).

In an exemplary embodiment, insertion guide tube 810 is made of polyimide. The slit and/or gap is laser cut, in some embodiments.

Figure 12A:
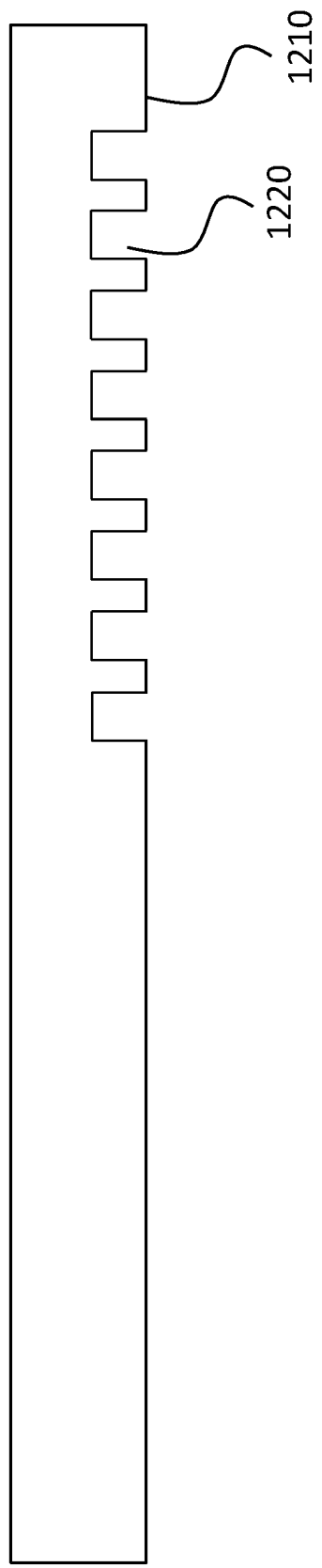
Figure 12B:
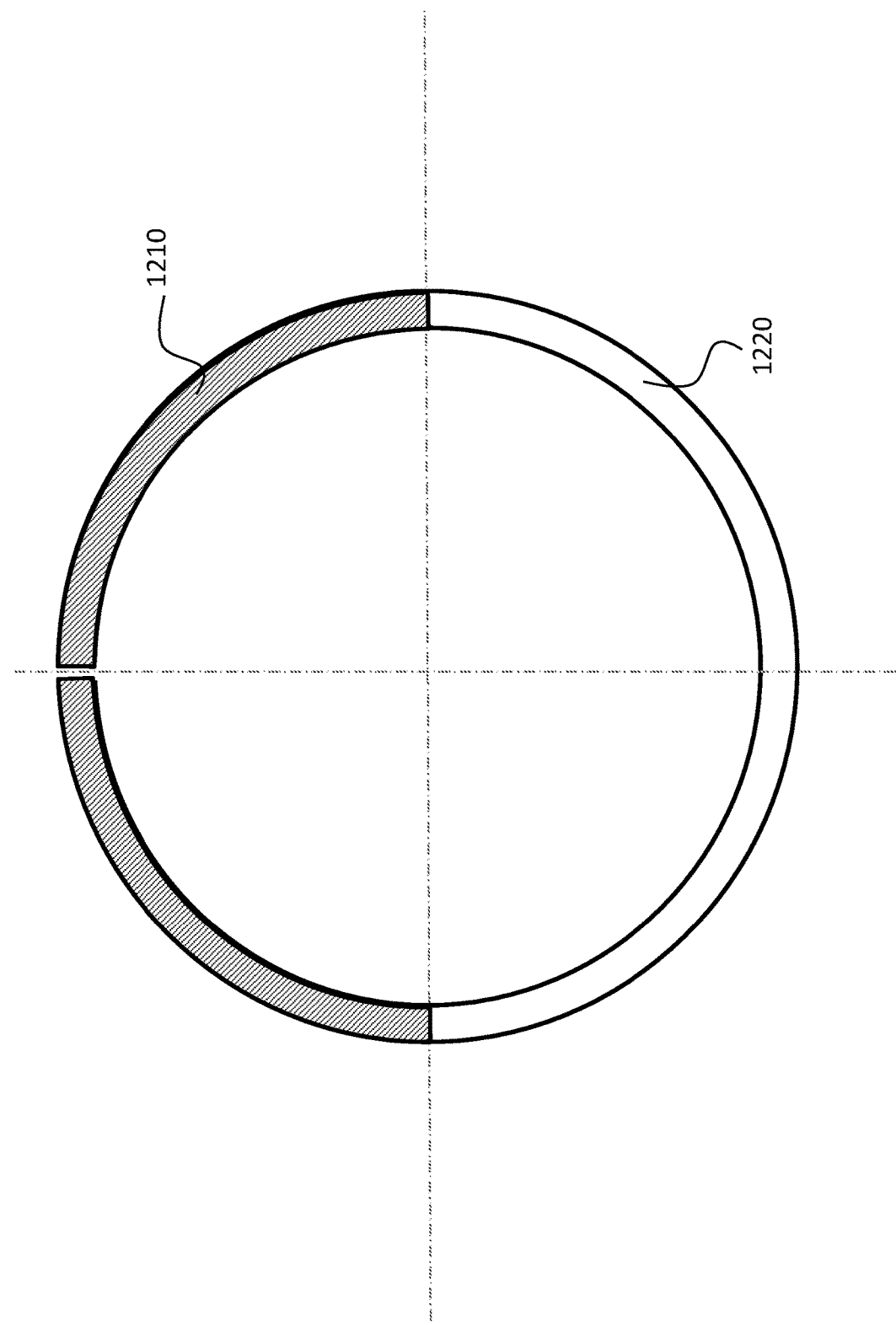

FIG. 12A depicts a side view (where the gap/slit would be on top (not seen in this view as the material of the guide eclipses that slit/gap)) of a distal end of an exemplary guide 1210, showing openings 1220. This is an exemplary embodiment where the openings form ribs and the portions of the guide without the openings form a quasi-spine (actually, two spines, one on either side of the slit/gap). FIG. 12 B depicts a cross-sectional view, which section extends normal to the longitudinal axis of the guide and extends through an opening. As can be seen, the opening 1220 extends completely from the left side of the guide to the right side of the guide, and does not extend to the gap/slit at the top.

Figure 13:
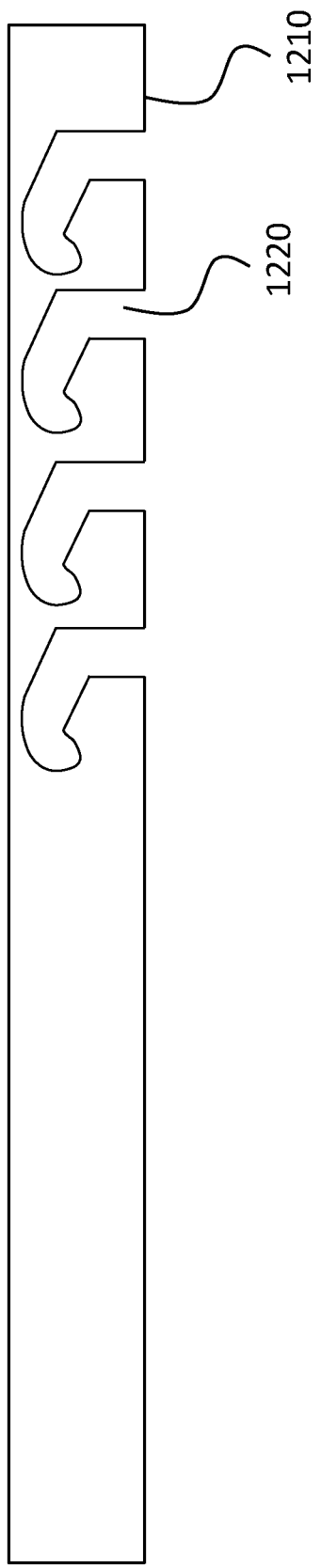
Figure 14A:
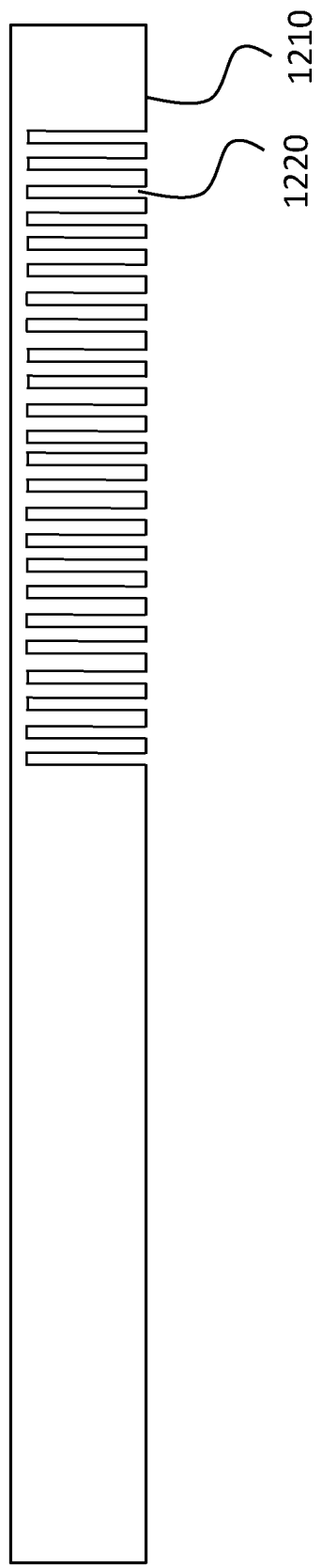

FIG. 13 depicts an exemplary embodiment where the openings 1220 are compound openings. FIG. 14A depicts an exemplary embodiment where the openings 1220 extend further up the lateral sides of the guide. FIG. 14B depicts a cross-section on a plane lying normal to the longitudinal axis of the guide through an opening, and depicts how the openings extend further up the lateral sides of the guide.

Figure 15:
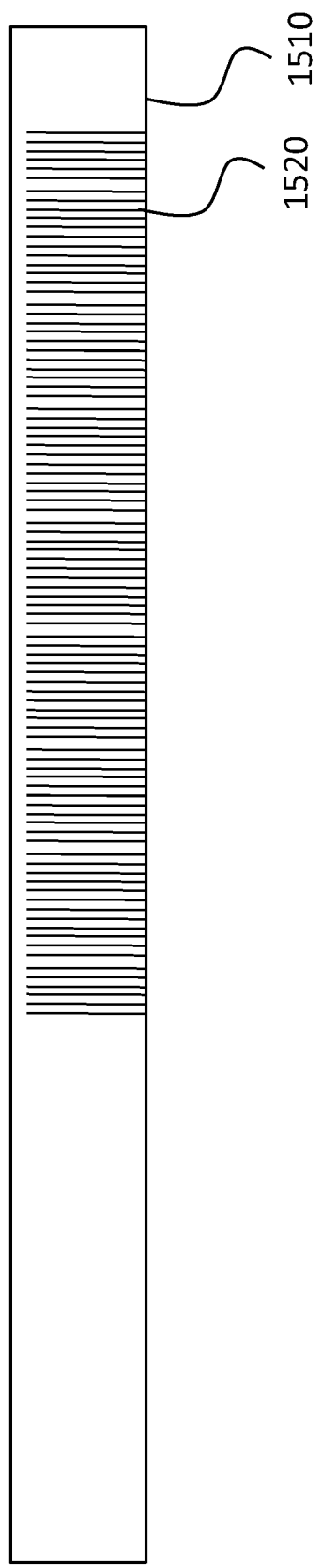

While the embodiments detailed above have represented the openings as gaps in the wall of the guide, FIG. 15 depicts an alternate embodiment where slits 1520 are instead utilized with a guide 1510. It is noted that a combination of slits and gaps can be utilized with respect to establishing the structure on the lateral sides of the guide.

Figure 16:
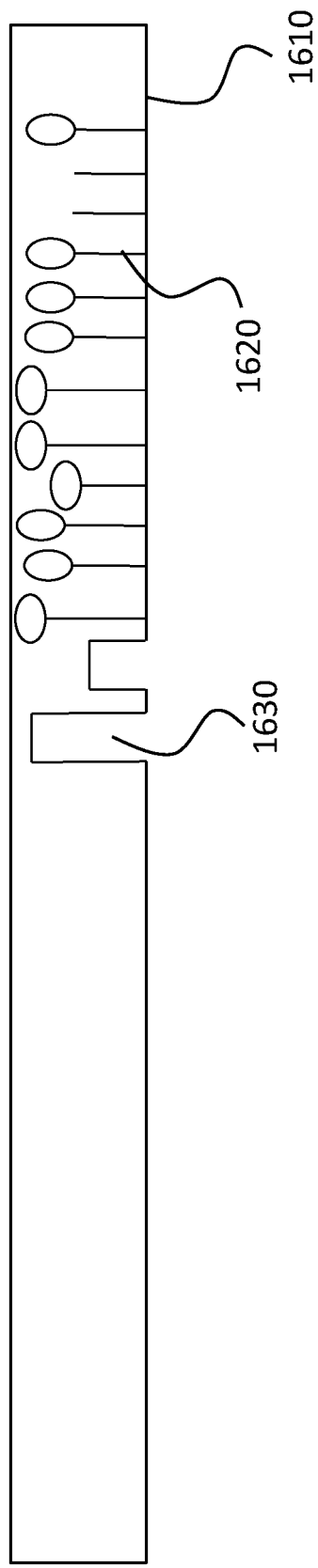

FIG. 16 depicts an alternate embodiment of a guide 1610 that has a combination of slits and gaps and where slits and gaps are combined at the same section along the longitudinal axis of the guide. The portion identified as 1620 is a location where material is separated but abutting, as opposed to 1630, where the material is both separated and non-abutting.

Figure 17A:
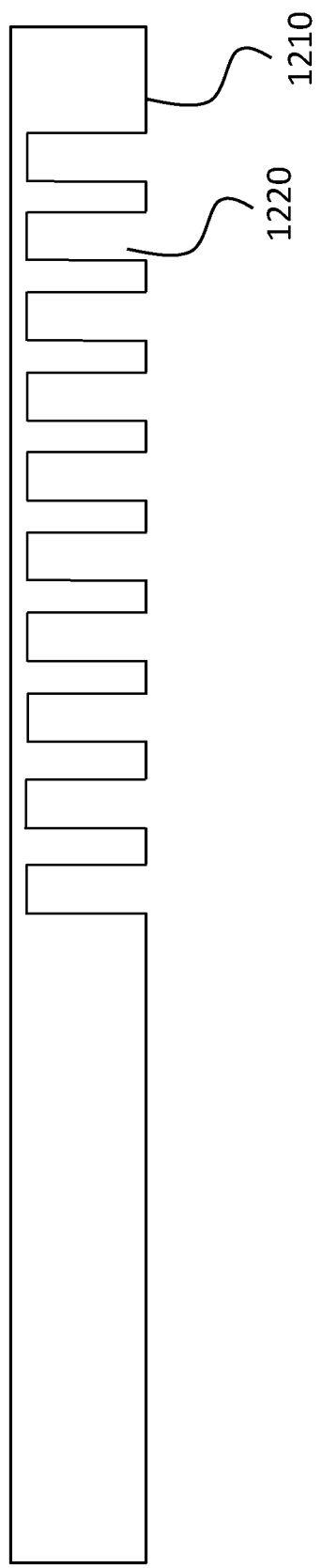

Embodiments can include various spacings of the gaps and/or slits, both with respect to the distance between each other and with respect to establishing the width of the opening. FIG. 17A depicts another exemplary embodiment where the openings are relatively larger than that which corresponds to the embodiment of FIG. 14A detailed above.

Figure 17B:
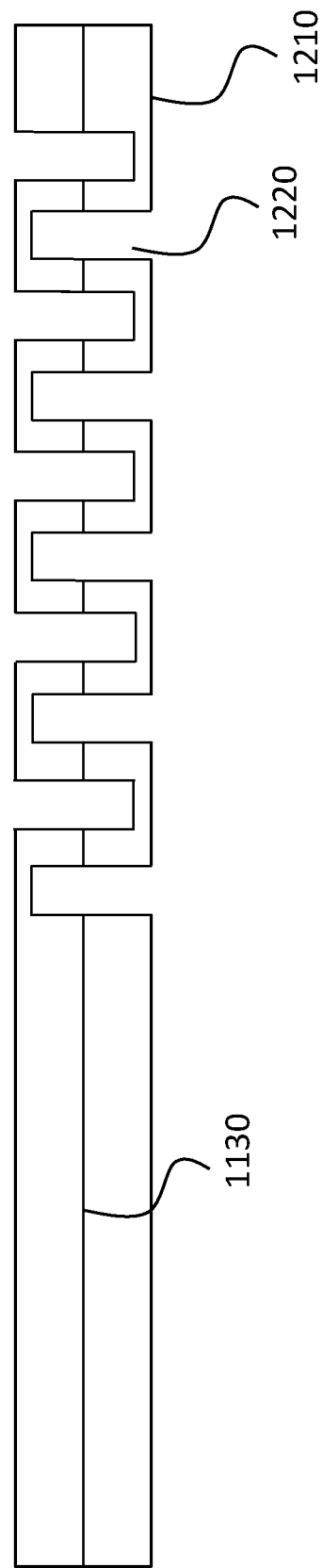

As noted above, in at least some exemplary embodiments, the openings in the tube are always spaced away from the slit and/or gap. This is as differentiated from, for example, the design represented by FIG. 17B, where the openings 1130 extend across the slit 1130. To be clear, in at least some exemplary embodiments, the configuration of FIG. 17B is explicitly not utilized. That said, in at least some exemplary embodiments, no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 percent of the openings and/or area making up the total amount of openings crosses the slit/gap (where the area of the slit/gap does not constitute an area with respect to the just mentioned qualifications).

Figure 17C:
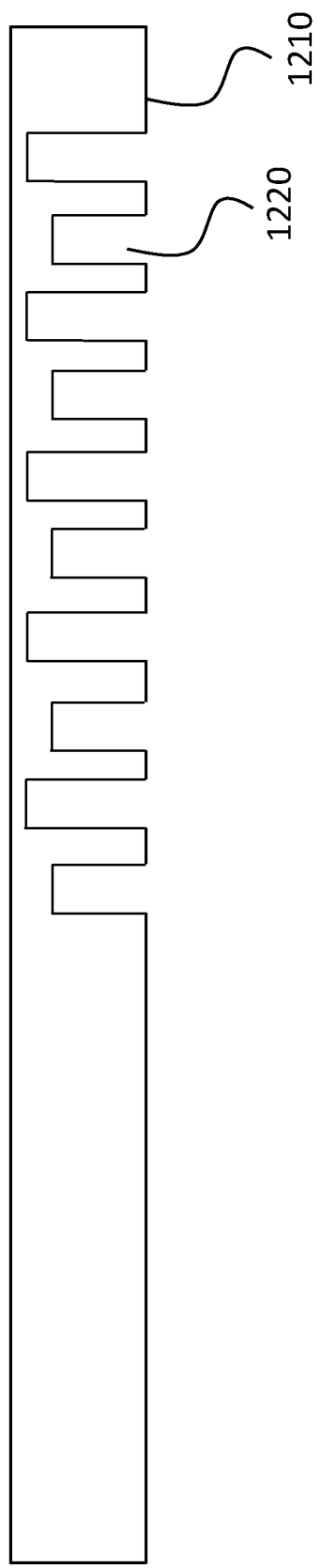

It is noted that while the embodiments of FIGS. 13-14B, etc., show the openings arrayed in a symmetric manner and a consistently same manner (e.g., each is identical and each is located, with respect to distance along the longitudinal axis, in the same manner and are located in the same way with respect to angular location about the longitudinal axis), in some other embodiments, the openings are not arrayed in a symmetrical manner and/or are not arrayed in a consistently same manner. In this regard, FIG. 17C presents an exemplary embodiment where the various openings angularly extend about the longitudinal axis by different amounts. While the embodiment of FIG. 17C presents a repeating pattern, it is noted that in alternate embodiments, the angular extension can be different for each opening and/or otherwise need not include a repeating pattern. Indeed, in an exemplary embodiment, there is no pattern.

Figure 17D:
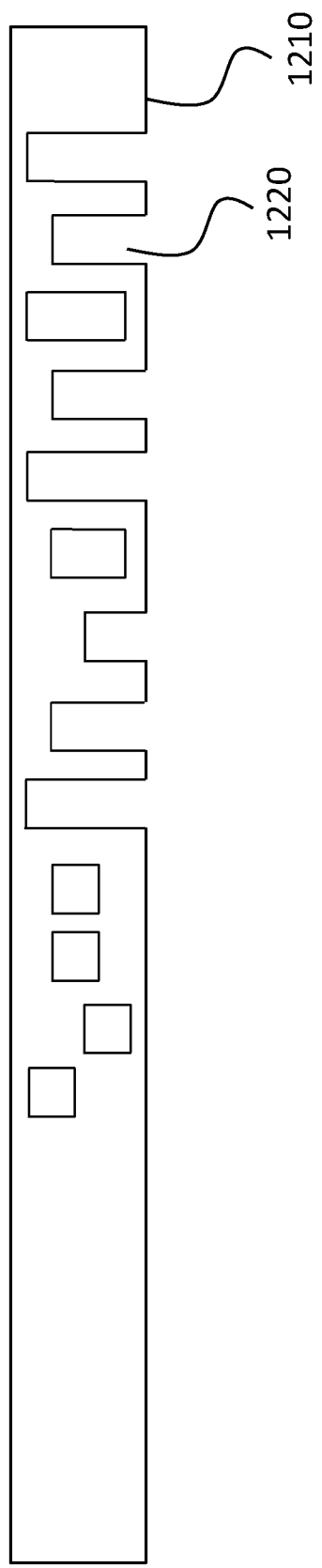

FIG. 17D presents an alternate embodiment of the embodiment of FIG. 17C, where at least some of the openings do not extend all the way to the bottom of the tube. Still, in some embodiments, all of the openings extend to the bottom of the tube. In an exemplary embodiment, no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 percent of the openings and/or area making up the total amount of openings do not extend to the bottom of the tube. Any arrangement of openings that can enable the teachings detailed herein can be utilized in at least some embodiments.

Figure 17E:
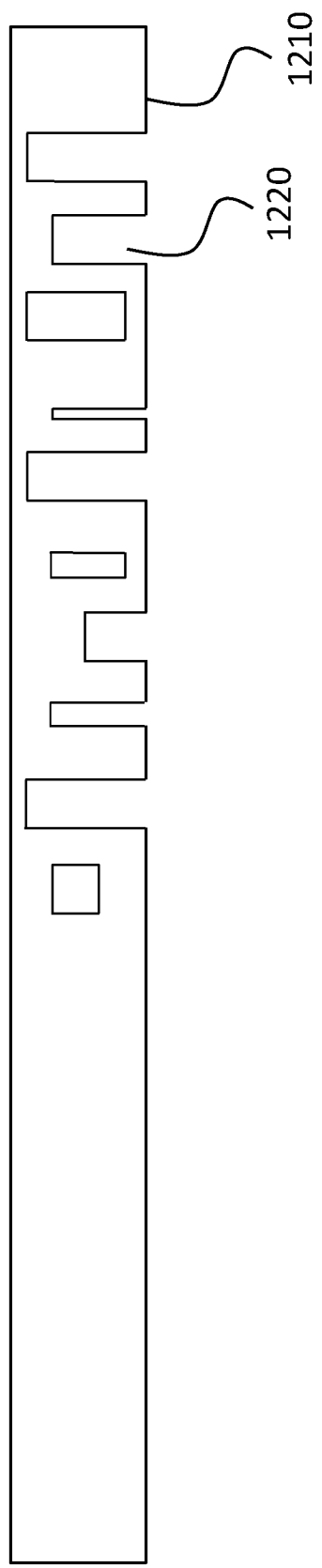
Figure 17F:
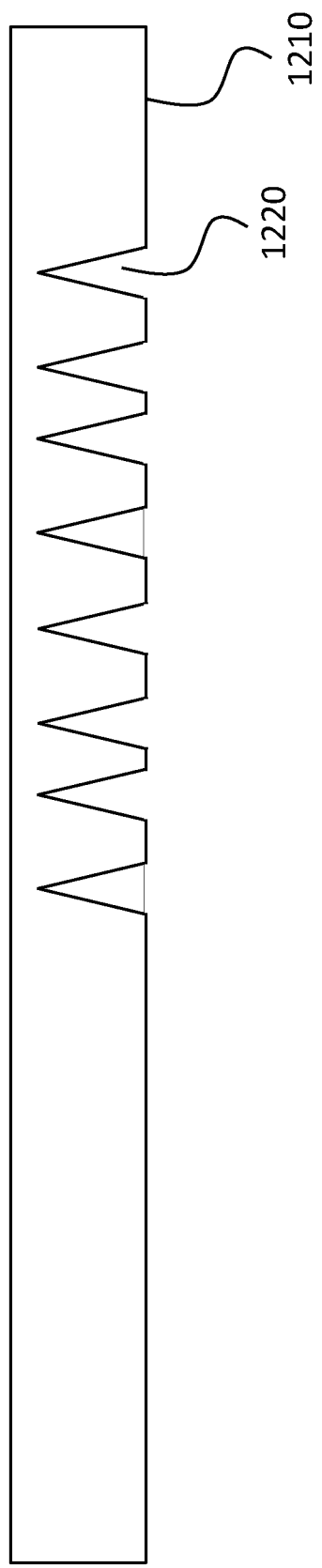
Figure 17G:
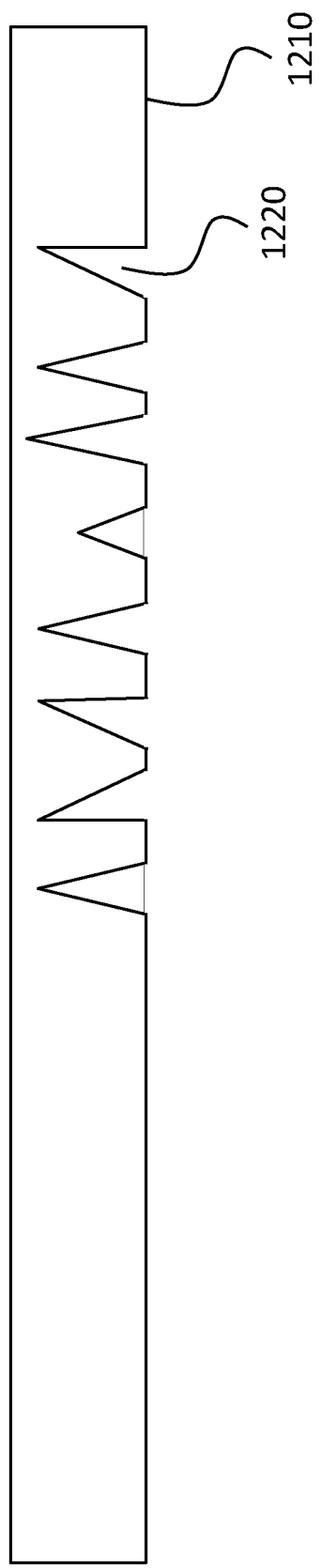

It is also noted that in at least some exemplary embodiments, the widths of the openings are not uniform, but instead can vary. FIG. 17E depicts another exemplary embodiment, where the widths of the openings vary from one opening to the other. Moreover, it is noted that in at least some exemplary embodiments, the widths of the openings vary with respect to angular location about the longitudinal axis of the tube. FIG. 17F depicts an exemplary embodiment of such an exemplary embodiment. FIG. 17G depicts another embodiment where various openings are not symmetrical with respect to one another and/or with respect to the widths of the openings with respect to angular location about the longitudinal axis.

Figure 18A:
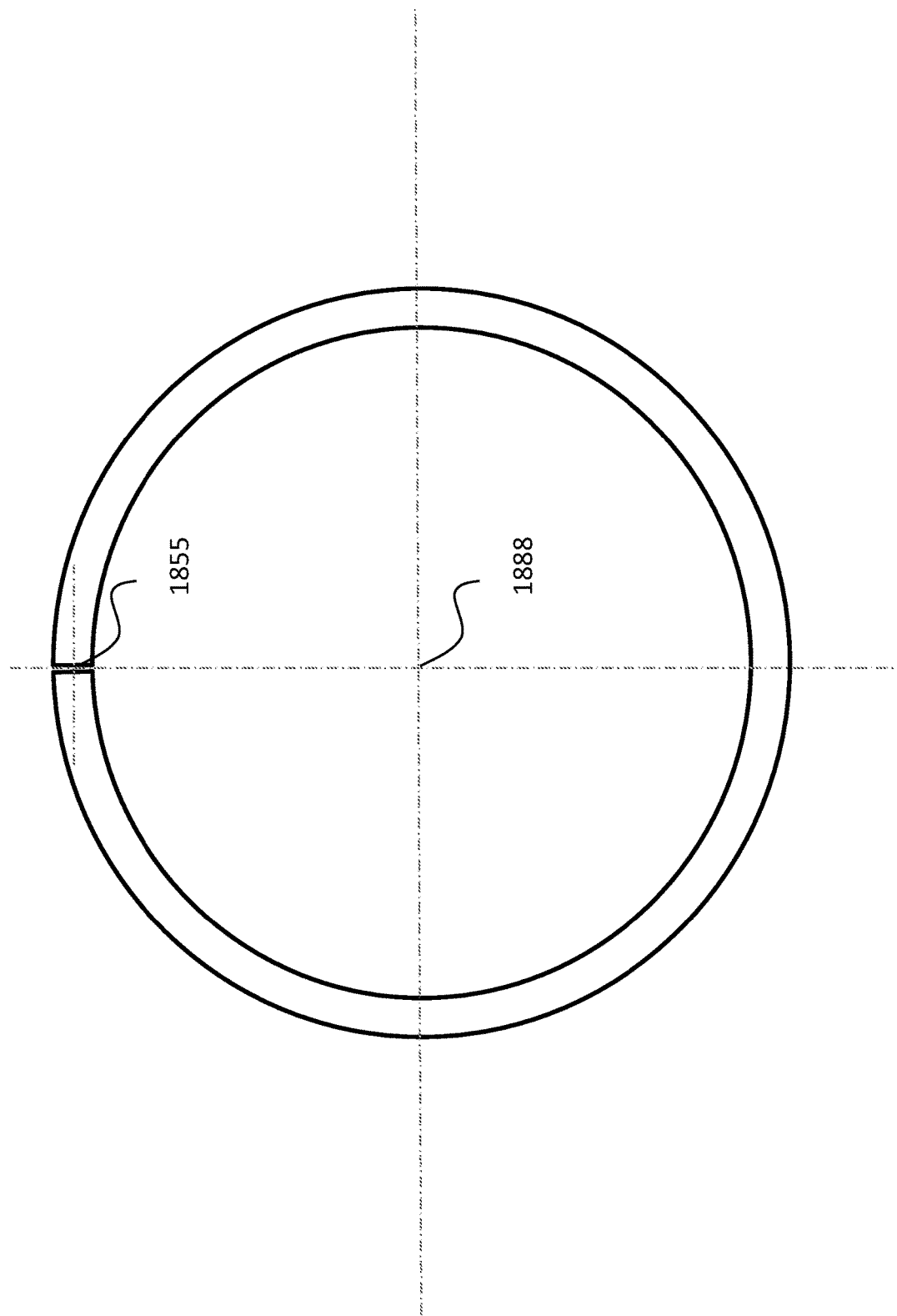
FIGS. 18-21C present schematics presenting features of some embodiments of tubes according to embodiments.

In an exemplary embodiment, providing the slits and/or gaps such that they extend from one side of the guide to the other side of the guide along the bottom of the guide can have utilitarian aspect of moving the neutral bending axis away from the longitudinal axis of the guide. In this regard, with respect to FIG. 18A, FIG. 18A depicts the longitudinal axis 1888 of the guide and the neutral bending axis 1855 of the guide. In the embodiment of FIG. 18A, the neutral bending axis would be about where the longitudinal axis is located without the openings. However, because of the openings, the neutral axis 1855 is moved further upwards, away from the longitudinal axis. This can have utilitarian value with respect to maintaining, at least in part, the overall interior geometry of the channel of the guide.

It is noted that any bending detailed herein refers to flexible bending/bending in an elastic manner, as opposed to a plastic manner, or at least bending that, for the most part, is elastic. Material will sometimes have a memory of being bent, and will not return to the totally unbent position without some form of additional force. That is still flexible bending. In an exemplary embodiment, when the tube is bent according to at least some scenarios herein, at least 80, 81, 82, 83, 84, 85, 86, 87, 88, 89, 90, 91, 92, 93, 94, 59, 96, 97, 98, 99 or 100% of the bending will dissipate upon relieving the force that cause the bending.

FIG. 18B depicts an exemplary embodiment where the gap is off-center relative to the vertical plane (i.e., the claim that is normal to the lateral plane, the vertical plane is a plane that extends from the bottom to the top and passes through the center of the tube). Any arrangement of gap locations and geometries and/or slit locations and geometries can be utilized in at least some exemplary embodiments providing that there is utilitarian value there with. In an exemplary embodiment, the center of the gap and/or slit (the center being a location equidistant between the two surfaces that create the slits and/or gap—in FIG. 18B, represented at point 1288) and the angle of the plane passing through the point 1288 and the longitudinal axis of the tube and the plane extending vertical and also extending through the longitudinal axis is angle A66. Angle A66 can be about any vale of (and including) 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 or any value or range of values therebetween (and inclusive) of these values in 0.1 degree increments (e.g., 2 to 30, 3.3 to 4.4, 5.5, 7.2, etc.).

Also, FIG. 18B presents an exemplary embodiment where the surfaces that create the gap are located on planes but are obliquely angled relative to one another. Again, it is noted that in some alternative embodiments, the planes can be parallel to one another owing to the local geometry of the surface that forms the gap and/or slit. In an exemplary embodiment, these parallel planes can be equidistant from the longitudinal axis, while in other embodiments, the center point of the planes can be a distance from the longitudinal axis. Any arrangement that can enable the teachings detailed herein can be utilized in at least some exemplary embodiments.

Figure 18C:
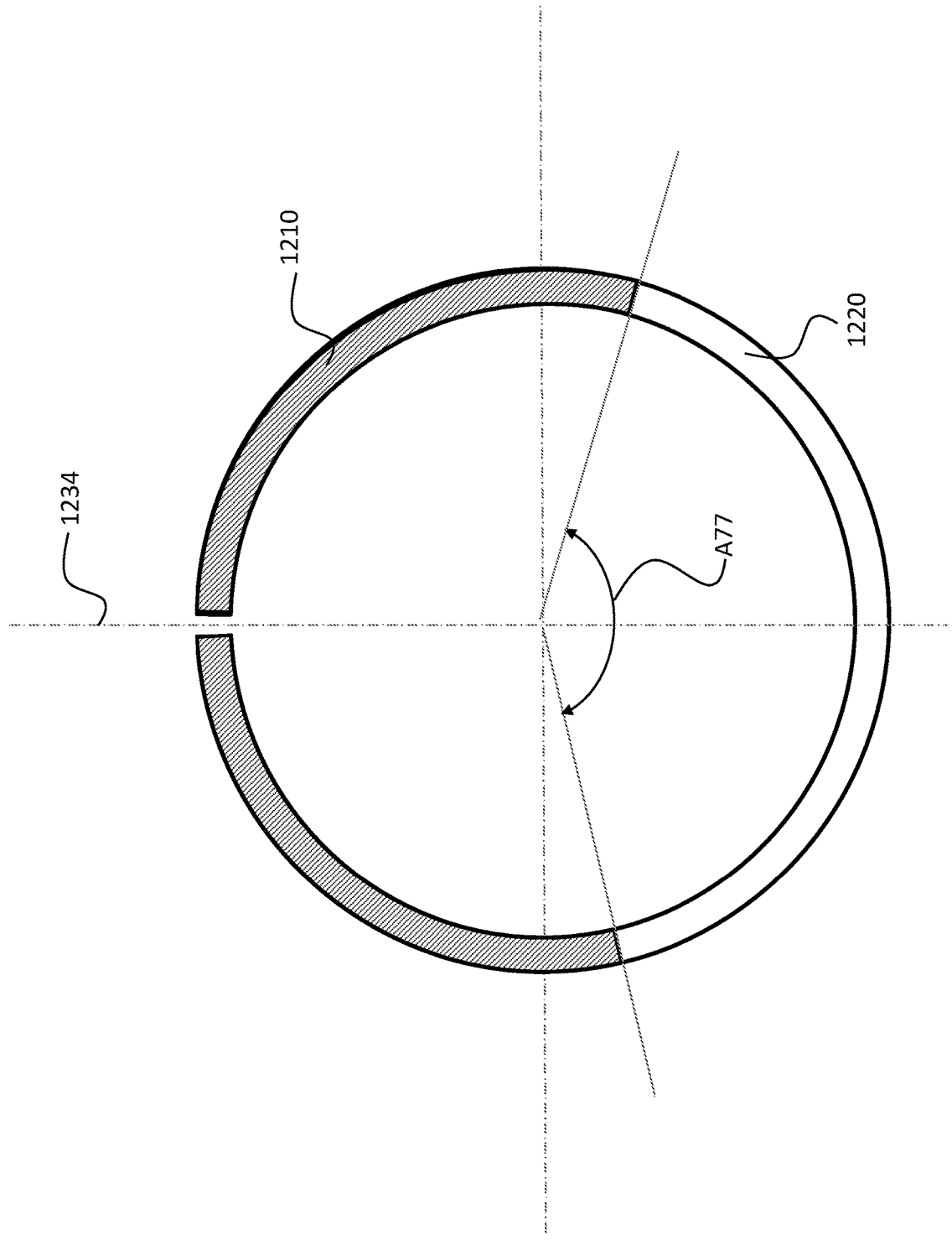

FIG. 18C presents a schematic that has utilitarian value with respect to detailing some of the features of some embodiments. In this regard, it can be seen that in angle measurement A77 has been superimposed onto the cross-section of the tube 1210. This angle indicates the angular sweep of the openings 1220. In an exemplary embodiment, A77 can be greater than, less than, and/or about equal to two times 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 16.5 or 170 degrees or more or A77 can be any value or range of values therebetween in 0.1 degree increments. In an exemplary embodiment, the openings are symmetrical about axis 1234, which, in this embodiment, extends through the center point of the tube and also through the center of the gap. In an exemplary embodiment, axis 1234 is the lateral axis extending from the bottom to the top, as opposed to the lateral axis extending from left to right. That is, the sweep of the opening to the left of axis 1234 is equal to the sweep of the opening to the right of axis 1234. That said, in some alternate embodiments, the openings are not symmetrical and thus the sweep on one side of the axis of the greater than or less than the sweep on the other side of the axis. Consistent with the embodiments detailed above, the openings can be different along the longitudinal direction. Also, each particular opening can have a different sweep depending on the location along the longitudinal direction.

In an exemplary embodiment, with respect to imaginary planes that are normal to the longitudinal axis, which planes are located every 0.5, 1, 1.5, 2, 2.5, 3, 3.5, 4, 4.5, 5, 5.5, 6, 6.5, 7, 7.5, 8, 8.5, 9, 9.5 or 10, 11, 12, 13, 14, 15, 16, 17, 18, 19, or 20 mm or any value or range of values therebetween in 0.1 mm increments, the tube is symmetrical about an axis that extends from the top to the bottom. Also, in some embodiments, for those planes, the tube is not symmetrical about an axis that extends left to right through the center of the tube.

Thus, in view of the above, it can be seen that in an exemplary embodiment, there is an insertion tool including an insertion guide that is flexible in a direction lying in at least a plane lying on a longitudinal axis thereof, the insertion guide having a slit and/or a gap extending in the longitudinal direction, the plane extending through the slit and/or gap, wherein the guide is configured to maintain at least a portion of a pre-curved electrode assembly in a substantially straight configuration (some non-straightness can exist—this is detailed below) while preventing the electrode assembly from twisting in response to stresses induced by bias forces which urge the assembly to return to its pre-curved configuration, when the insertion guide flexibly bent in the plane. In an exemplary embodiment, the portion of the pre-curved electrode assembly that is maintained in a substantially straight configuration is the portion located in the tube, or at least a portion located in a portion of the tube.

In an exemplary embodiment, the insertion guide can correspond to the tubes as detailed herein and/or variations thereof. Accordingly, in an exemplary embodiment, at least a portion of the guide that is flexible can be made of a polymer and/or can be made of a metal-based material. Providing that the tube is flexible and can bend according to at least some of the bending regimes detailed herein, such can be utilized to enable the teachings detailed herein.

Figure 19:
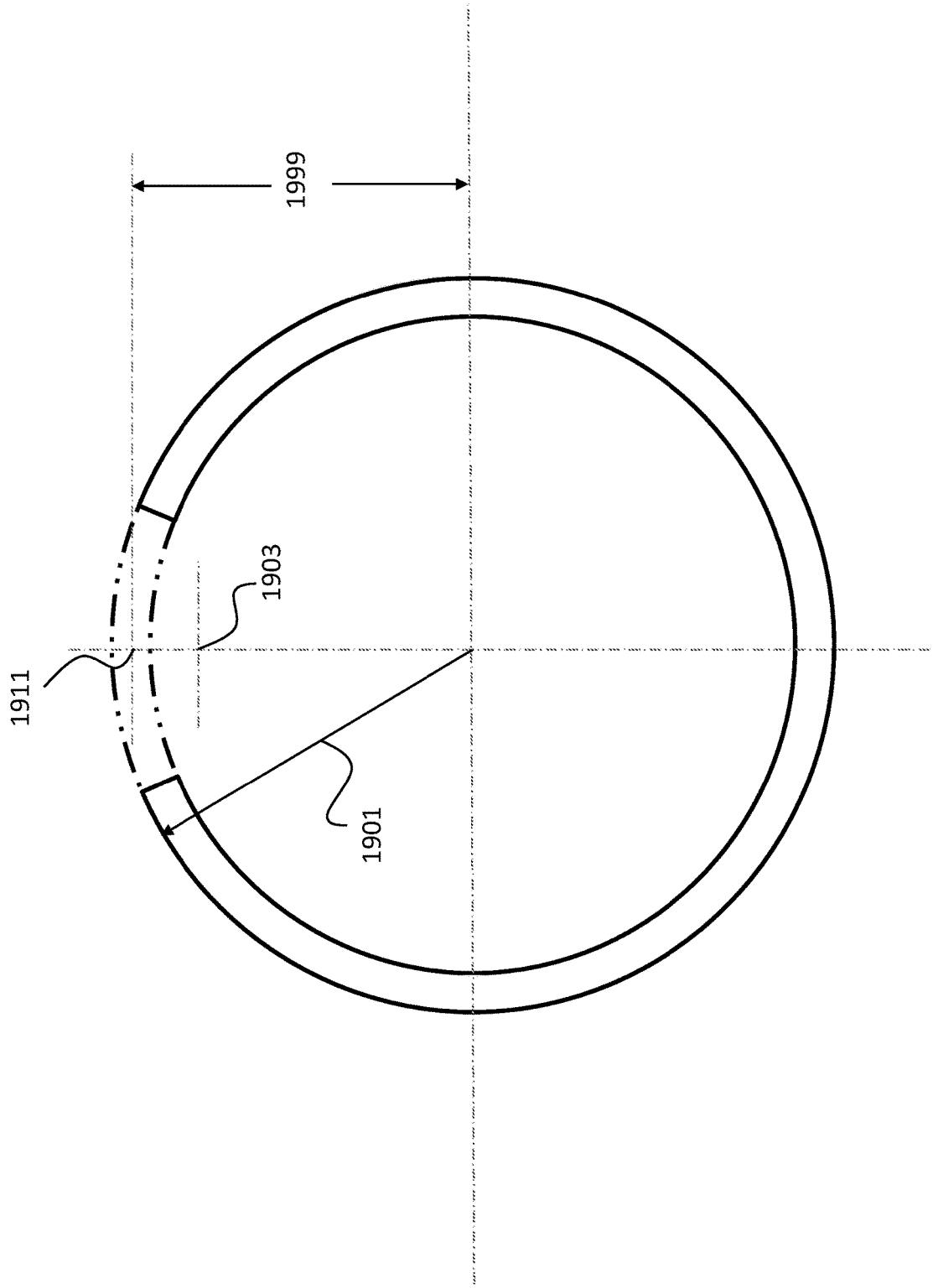

FIG. 18A presents a cross-sectional view of an exemplary slit configuration guide, while FIG. 19 presents an exemplary gap configuration guide. As can be seen, the distance from the longitudinal axis to the normal bending axis is represented by reference 1999. In an exemplary embodiment, this distance is a percentage of the maximum outer radius of the guide 1901 at that section (cross-section). The maximum outer radius of the guide 1901 is seen as being measured from the actual outer surface of the guide. It is noted that in an exemplary embodiment, that has maximum outer radius can be measured from an extrapolated surface of the guide, which extrapolated surface is presented in the phantom line seen in FIG. 19.

Figure 20:
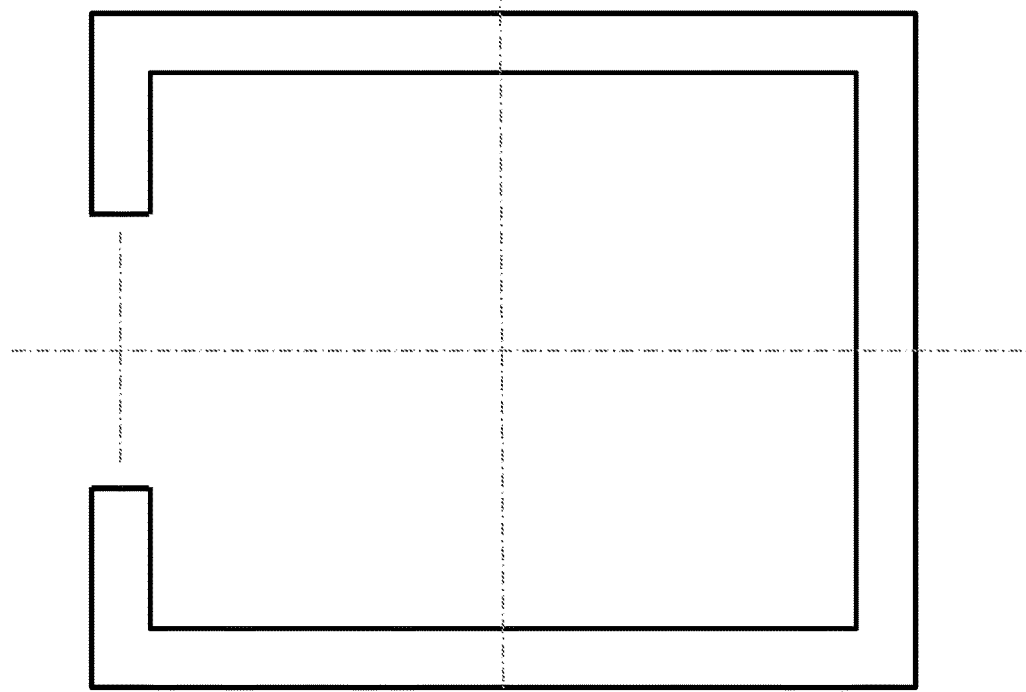

FIG. 20 shows an alternative embodiment of a guide where the guide is rectangular in cross-section as opposed to circular or oval shaped. FIG. 21 depicts an exemplary embodiment of the guide bending, where the bending occurs along the neutral axis. FIG. 21 presents an extrapolated longitudinal axis/the axis as is located without the guide bending, along with an axis based on the distal end of the guide, showing the angle between the two.

Thus, as can be see, there is a device, comprising an insertion tool including an elongate insertion guide that is flexible in a direction lying in at least a plane lying on a longitudinal axis thereof, wherein the device is an insertion tool for a cochlear electrode array, and the insertion guide is configured to flex in the plane such that a neutral axis is located substantially away from the longitudinal axis. In an exemplary embodiment, the guide has a maximum outer radius lying on a plane normal to the longitudinal axis measured from the longitudinal axis, and the neutral axis is at least 30%, 40%, 50%, 60%, 70%, 80%, 90%, 95% or more of the distance of the maximum outer radius from the longitudinal axis when measured on the plane. In an exemplary embodiment, the guide has a maximum outer radius lying on a plane normal to the longitudinal axis measured from the longitudinal axis, and the neutral axis is at least X % of the distance of the maximum outer radius from the longitudinal axis when measured on the plane, where X is 30, 35, 40, 45, 50, 55, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more or any value or range of values therebetween in 0.1% increments (e.g., 55.3% to 88.8%, 75.3%, etc.). In an exemplary embodiment, the neutral axis is within the top and bottom of the slit/gap (or an extrapolated profile thereof). In an exemplary embodiment, the neutral axis is within less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40% of the maximum outer radius from the longitudinal axis from the outside of the tube and/or within a distance from the outside of the tube that corresponds to less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 80, 90, 100, 110, 120, 130, 140, 150, 160, 170, 180, 190, 200, 225, 250, 275, 300, 325, 350, 375, 400, 450, 500, 550 or 600 percent of the minimum thickness of the tube.

In any event, as can be seen from FIGS. 18 and 19, in an exemplary embodiment, the neutral axis is located, relative to a direction normal to the longitudinal axis, within the slit and/or gap. This is seen, for example, with respect to axis 1911, as opposed to axis 1903. In an exemplary embodiment, the neutral axis is located, relative to a direction normal to the longitudinal axis, outboard of the bottom portion of the surface(s) of the guide establishing the gap.

In an exemplary embodiment, the insertion tool is configured such that the tube can bend according to any one or more of the bending scenarios detailed herein, as will be described in greater detail below in some instances, such that the change in the length along the surface(s) of the slit and/or gap relative to that in the relaxed state/unbent state/straight state is less than 1, 2, 3, 4, 5, 6, 7, 8, 9, 10, 11, 12, 13, 14, 15, 16, 17, 18, 19 or 20 percent.

Figure 21A:
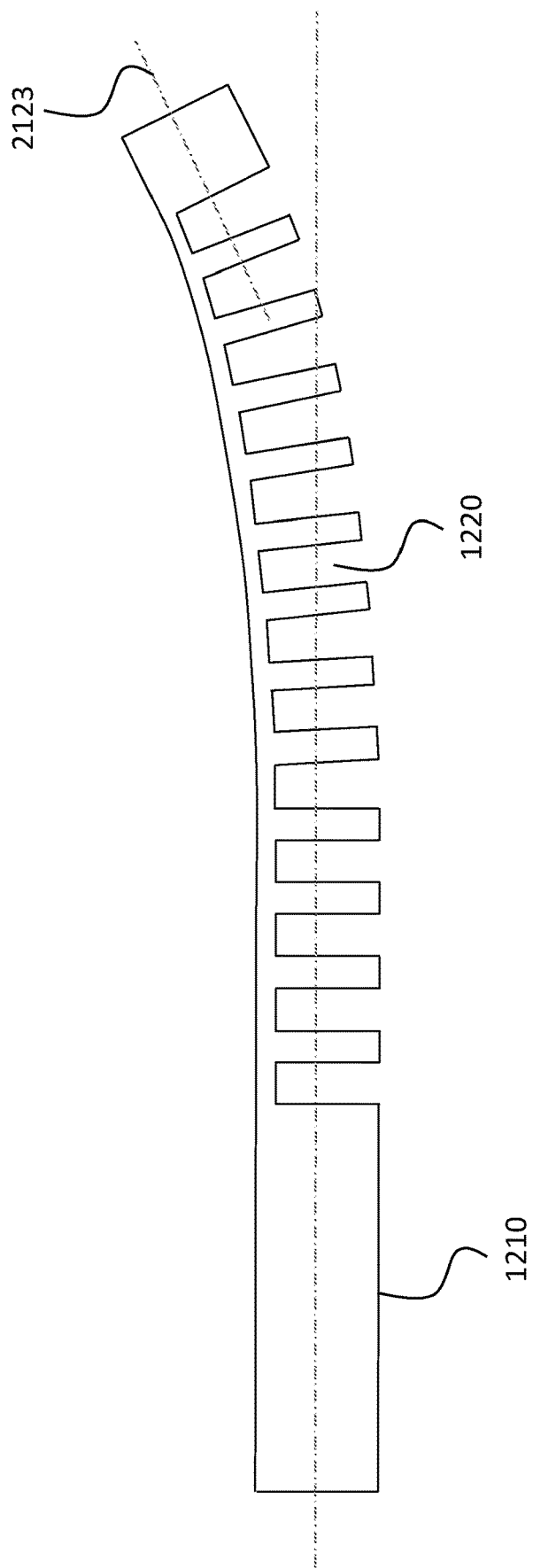
Figure 21B:
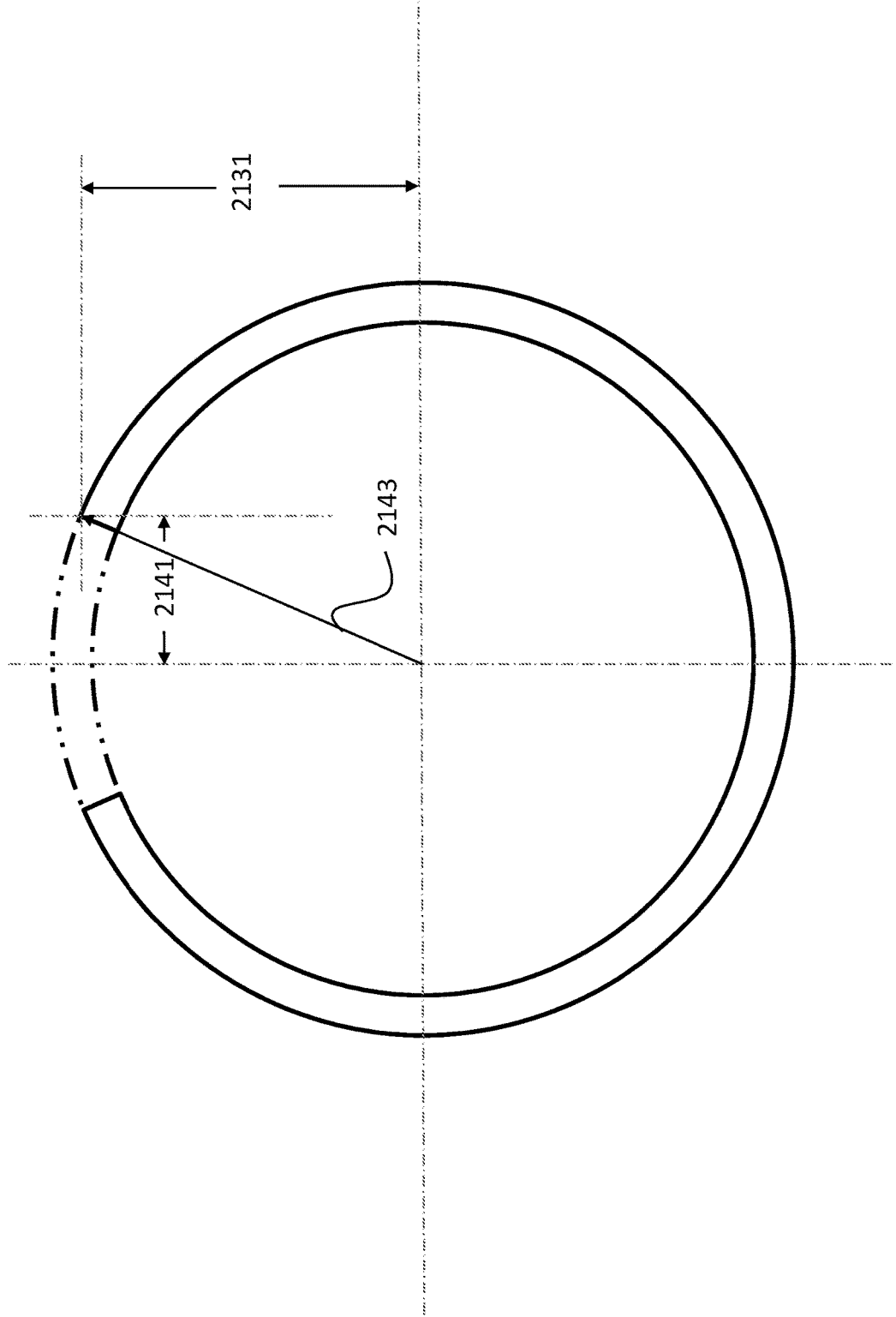

With respect to FIG. 21A, in an exemplary embodiment, the guide has a channel in which the cochlear electrode array moves during insertion and the guide is configured such that a longitudinal axis 2123 of the guide at the tip can move at least Y degrees relative to an unbent state/straight state/relaxed state without effectively deforming the channel (which includes without deforming the channel) and/or without deforming the channel, where Y is 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 61, 62, 63, 64, 65, 66, 67, 68, 69, 70 degrees or more or any value or range of values therebetween in 0.1 degree increments. With respect to FIG. 21A, in an exemplary embodiment, the guide has a channel in which the cochlear electrode array moves during insertion and the guide is configured such that a longitudinal axis of the guide at the tip can move at least Y degrees relative to an unbent/straight/relaxed state such that no interior diameter at one or more or all sections measured lying on a plane normal to the longitudinal axis is reduced and/or increased by more than 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20 percent, or any value or range of values therebetween in 0.025% increments. Accordingly, in an exemplary embodiment, the guide is configured so as to avoid collapsing and/or kinking when bent by one or more of the above noted angles.

In the exemplary embodiment of FIG. 21A, in the relaxed state and/or a state in which the tube is perfectly straight and/or unbent, the distance from the most distal end of the tube to the portion of the opening furthest from the distal end and/or the distance from the most distal end to the most forward surface of the stop (the surface closest to the distal end), as measured from a plane normal to the longitudinal axis and located at these locations, is more than or equal to H, where H can be 3, 4, 5, 6, 7, 8, 9, 10, 11, 12, 13, 14, 15, 16, 17, 18, 19, 20, 21, 22, 23, 24 or 25 mm or any value or range of values therebetween in 0.01 mm increments (e.g., 5.56 mm, 12.21 mm, 6.66 to 22.22 mm, etc.). In an exemplary embodiment, the aforementioned angles are measured such that, with respect to a right triangle, the hypotenuse corresponds to an extrapolated line that is parallel to and on axis 2123 and/or from a geometric center of the tube at the most distal location, and the leg opposite the hypotenuse lying on the original longitudinal axis (the horizontal in FIG. 21A) is such that the distance of the leg is any of the aforementioned values of H or any value or range of values therebetween in 0.01 mm increments, where the leg extends to the geometric center of an unbent portion of the tube. It is noted that in at least some exemplary embodiments, the aforementioned right triangle can be such that the location where the hypotenuse and the leg that is parallel to the longitudinal axis meet can correspond to the location of the furthest opening from the distal end and/or from the location of the stop (most forward surface). It is also noted that any of the aforementioned angles and/or distances can be measured from a location that meets one of these values irrespective if such is associated with stop and/or the opening. By way of example, the angular bending can be measured from a location 14.3 mm from the distal end (measured from the unbent state/relaxed state/straight state), which location may also have a bending component. Note also that in an exemplary embodiment, the measurement location can be where an extrapolated axis 2123 contacts the extrapolated longitudinal axis of the tube in the unbent configuration.

In an exemplary embodiment, the arrangements detailed herein can provide, in some instances, a structure that results in little to no twist when bent. In this regard, in an exemplary embodiment, now with reference to FIG. 21B, the tube is configured such that when the tube is bent according to any one or more of the bending scenarios detailed herein, similarly situated points along the tube do not move or move relatively little relative to the unbent state. More particularly, in some exemplary embodiments, the structure of the guide is such that, for any one or more or all of the distances H, and for any one or more or all of the aforementioned angles, dimensions 2141 and/or 2131 and/or 1243 change no more than 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20 percent, or any value or range of values therebetween in 0.025% increments and/or changed by no more than 0.01, 0.02, 0.04, 0.06, 0.08, 0.1, 0.12, 0.14, 0.16, 0.18, 0.2, 0.22, 0.24, 0.26, 0.28, 0.3, 0.35, 0.4, 0.45, 0.5, 0.55, 0.6, 0.65, 0.7, 0.75, 0.8, 0.85, 0.9, 0.95, or 1 mm relative to the locations in the unbent and/or straight and/or undeformed state. In an exemplary embodiment, similar dimensions for any of the points 2151, 2152, 2153, and/or 2154 of FIG. 21C change no more than 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20 percent, or any value or range of values therebetween in 0.025% increments and/or change by no more than 0.01, 0.02, 0.04, 0.06, 0.08, 0.1, 0.12, 0.14, 0.16, 0.18, 0.2, 0.22, 0.24, 0.26, 0.28, 0.3, 0.35, 0.4, 0.45, 0.5, 0.55, 0.6, 0.65, 0.7, 0.75, 0.8, 0.85, 0.9, 0.95, or 1 mm relative to the locations in the unbent and/or straight and/or undeformed state. It is also noted that in an exemplary embodiment, instead of the just noted features being relative to the unbent/straight/undeformed state, these features can be relative to similar locations along the longitudinal direction of the tube. For example, in an exemplary embodiment, for a location identified in FIG. 21B, the location does not change by more than any of the aforementioned values relative to the values for another similarly situated location in a longitudinal direction within and/or more than 1, 1.5, 2, 2.5, 3, 3.5, 4, 4.5, 5, 5.5, 6, 6.5, 7, 7.5, 8, 8.5, 9, 9.5 or 10, 11, 12, 13, 14, 15, 16, 17, 18, 19 or 20 mm on one or both sides. In an exemplary embodiment, the aforementioned phenomenon can be measured by, for example, creating imaginary planes that are normal to the longitudinal axis, which planes are located every 0.5, 1, 1.5, 2, 2.5, 3, 3.5, 4, 4.5, 5, 5.5, 6, 6.5, 7, 7.5, 8, 8.5, 9, 9.5 or 10, 11, 12, 13, 14, 15, 16, 17, 18, 19, or 20 mm or any value or range of values therebetween in 0.1 mm increments. The locations can be scribed or otherwise identified, and then the tube can be bent according to the angles detailed herein, and then the movement of these locations can be compared to that which was the case prior to bending. It is noted that any of the diameter dimensional relations herein can also be compared to each other over these distances (e.g., two respective diameters for similarly situated structure except at different locations along the longitudinal direction (e.g., within 8.5 mm of each other) increase and/or decrease by no more than 0.5%). Again, two or three or four more different planes can be compared to one another, and the relative change from one to the other can be evaluated. In this regard, the aforementioned consistencies can be present over two or three or four or five or six or seven or eight or nine or 10 or 11 or 12 or 13 or 14 or 15 or 16 or 17 or 18 or 19 or 20 of the planes spaced as just detailed, the limiting factor being the length of the tube.

It is noted that embodiments include tubes that meet the aforementioned movement requirements for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more locations, which locations can be spaced according to the plane locations detailed above, the limiting factor being the length of the tube.

Figure 21C:
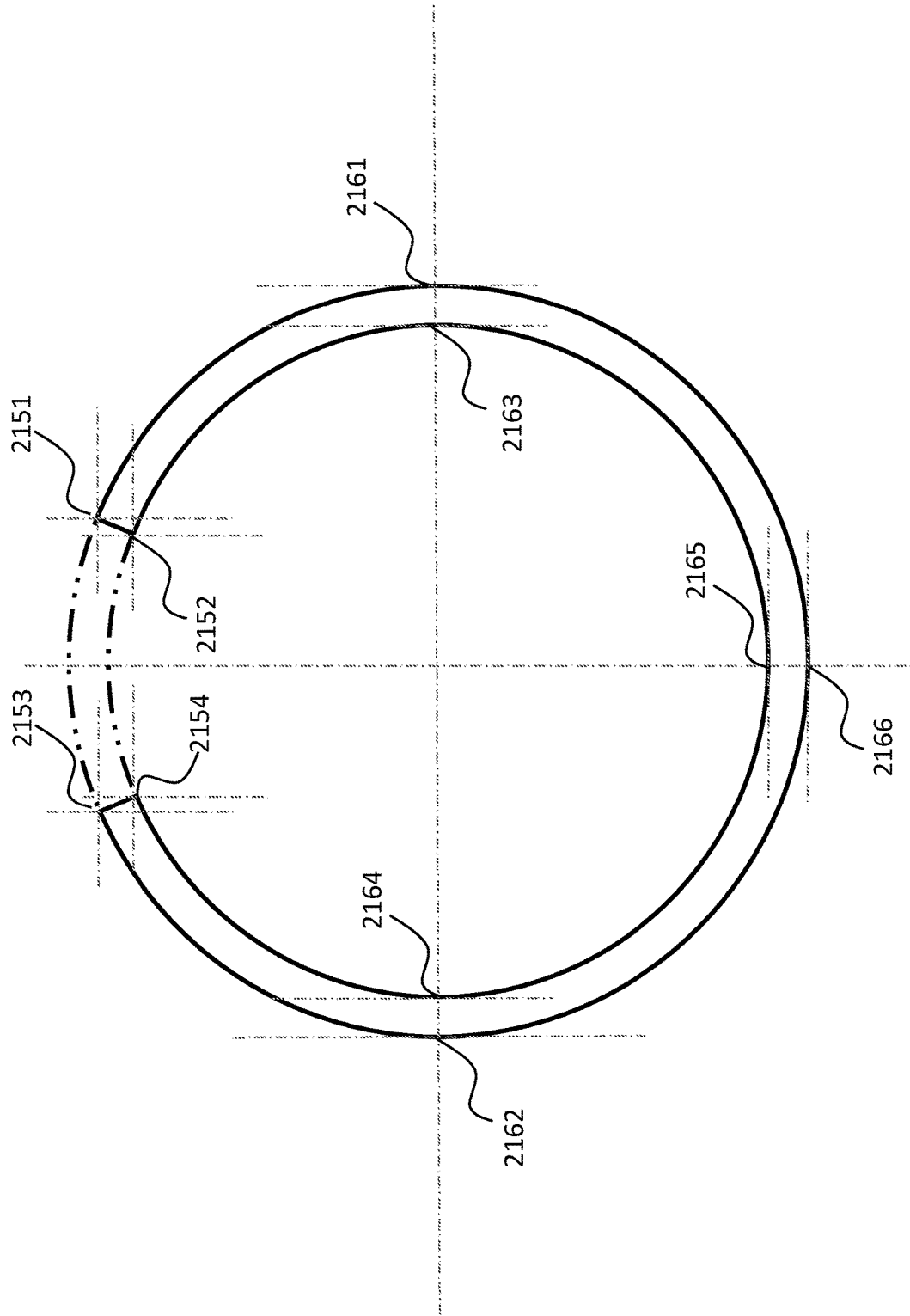

FIG. 21C presents some exemplary locations (locations 2151, 2152, 2153, 2154, 2161, 2162, 2163, 2164, 2165, and 2166) from which the exemplary measurements can be taken.

In view of the above, in an exemplary embodiment, the guide is configured such that the amount of twisting is limited (including no twisting) when bent. By way of example only and not by way of limitation, with respect to any of the aforementioned locations, an amount of rotation/twisting relative to a relaxed/straight/unbent state is less than 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 degrees. It is also noted that in an exemplary embodiment, for any one or more of these locations, the amount of twist/rotation does not change by more than any of the aforementioned values in a longitudinal direction within and/or more than 1, 1.5, 2, 2.5, 3, 3.5, 4, 4.5, 5, 5.5, 6, 6.5, 7, 7.5, 8, 8.5, 9, 9.5 or 10, 11, 12, 13, 14, 15, 16, 17, 18, 19 or 20 mm on one or both sides. By way of example only and not by limitation, in an exemplary embodiment, the aforementioned phenomenon can be measured by, for example, creating imaginary planes that are normal to the longitudinal axis, which planes are located every 0.5, 1, 1.5, 2, 2.5, 3, 3.5, 4, 4.5, 5, 5.5, 6, 6.5, 7, 7.5, 8, 8.5, 9, 9.5 or 10, 11, 12, 13, 14, 15, 16, 17, 18, 19, or 20 mm or any value or range of values therebetween in 0.1 mm increments. The locations can be scribed or otherwise identified, and then the tube can be bent according to the angles detailed herein, and then the movement of these locations can be compared to that which was the case prior to bending. Again, two or three or four more different planes can be compared to one another, and the relative change from one to the other can be evaluated. In this regard, the aforementioned consistencies can be present over two or three or four or five or six or seven or eight or nine or 10 or 11 or 12 or 13 or 14 or 15 or 16 or 17 or 18 or 19 or 20 of the planes spaced as just detailed, the limiting factor being the length of the tube. It is noted that embodiments include tubes that meet the aforementioned movement requirements for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more locations, which locations can be spaced according to the plane locations detailed above, the limiting factor being the length of the tube.

Figure 22:
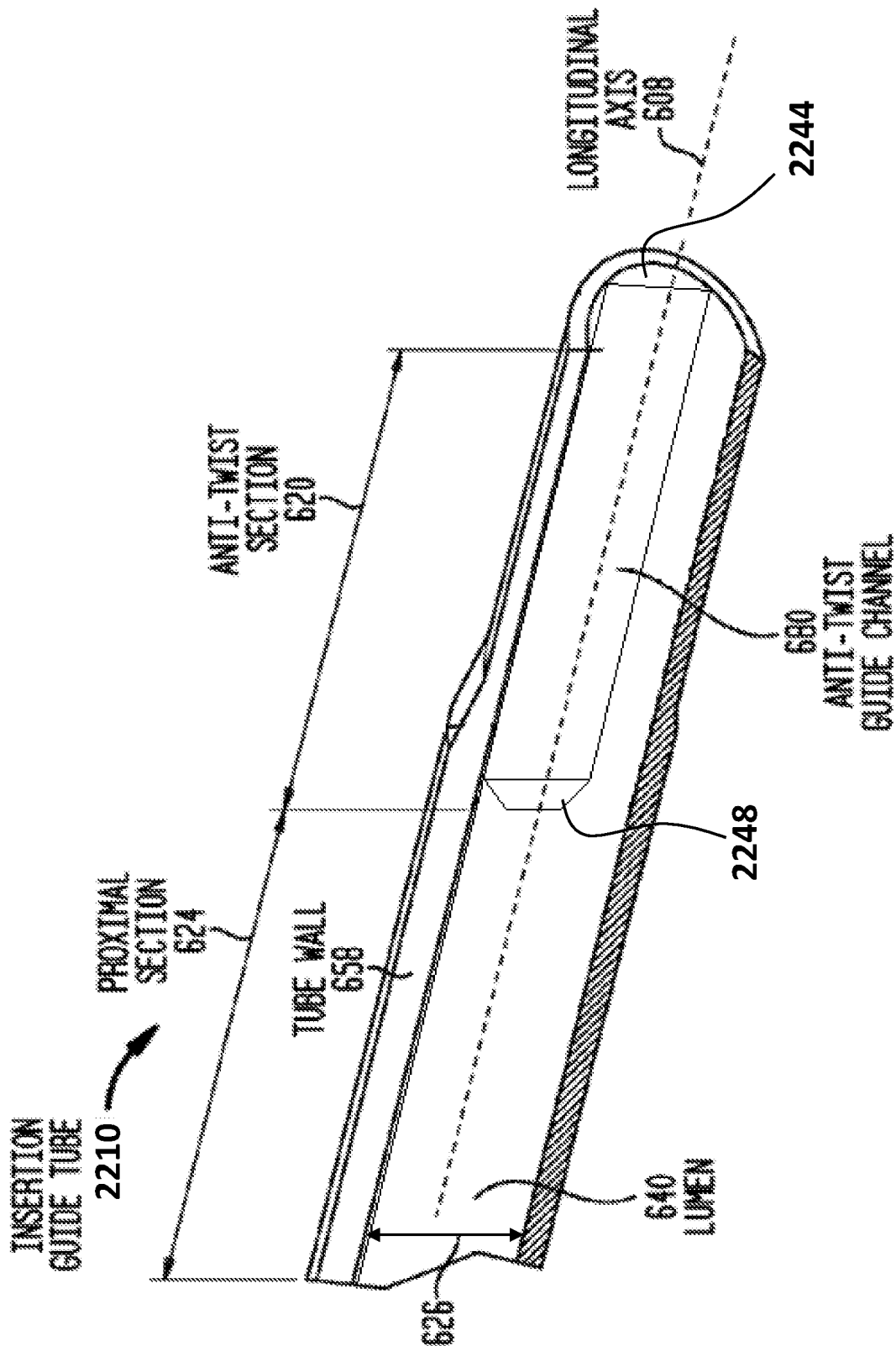
FIGS. 22-31 present exemplary schematics of exemplary anti-rotation features of some embodiments.

FIG. 22 is a partial cross-sectional view of an embodiment of insertion guide tube 2210 (but again, embodiments are not limited to a tube). As can be seen, insertion guide tube 2210 includes an anti-twist section 620 formed at the distal end of the guide tube. Anti-twist section 620 is contiguous with the remaining part of guide tube 610. Guide tube 2210 has a lumen 640 which, in proximal section 624 has a vertical dimension 626, and also a horizontal dimension (not shown), and a distal anti-twist section 620 has a vertical dimension that is the same as 626, but can be smaller in some embodiments. The horizontal dimension can also be smaller than that of the proximal section 624. In this embodiment, the horizontal dimension of lumen 640 decreases from that of the proximal section (which in the embodiment of the symmetrical circular channel, is dimension 626) due to a ramp 2248 at the proximal end of section 642.

In an exemplary embodiment, including or not including the ramp, the length of the flats of the anti-twist section can be more than, less than and/or about equal to 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 2.7, 3.8, 3.9, 4.0, 4.25, 4.5, 4.75, 5, 5.25, 5.5, 5.75, 6, 6.5, 7, 7.5, 8.0, 8.5, 9, 9.5, 10, 11, 12, 13, 14 15 mm or more or any value or range of values therebetween in 0.01 mm increments.

It is noted that the embodiment shown in FIG. 22 has a section that tapers outward, and thus has a section where the tube wall thickness is thicker at one location along the longitudinal direction relative to another location along the longitudinal direction. In some embodiments, there is no such tapering. In an exemplary embodiment, the tube is a uniform tube having a uniform outer maximum diameter. Any arrangement of tubes that can enable the teachings detailed herein can be utilized in at least some exemplary embodiments.

Anti-twist section 620 can, in some embodiments, cause a twisted electrode assembly traveling through guide tube 610 to return to its un-twisted state, and retains the electrode assembly in a straight configuration such that the orientation of the electrode assembly relative to the insertion guide tube 2210 does not change.

Electrode assembly 145 has a rectangular cross-sectional shape, with the surface formed in part by the surface of the electrode contact, referred to herein as top surface 650, and the opposing surface, referred to herein as bottom surface 652, are substantially planar. These substantially planar surfaces are utilized in embodiments of the insertion guide tube described herein.

Figure 24:
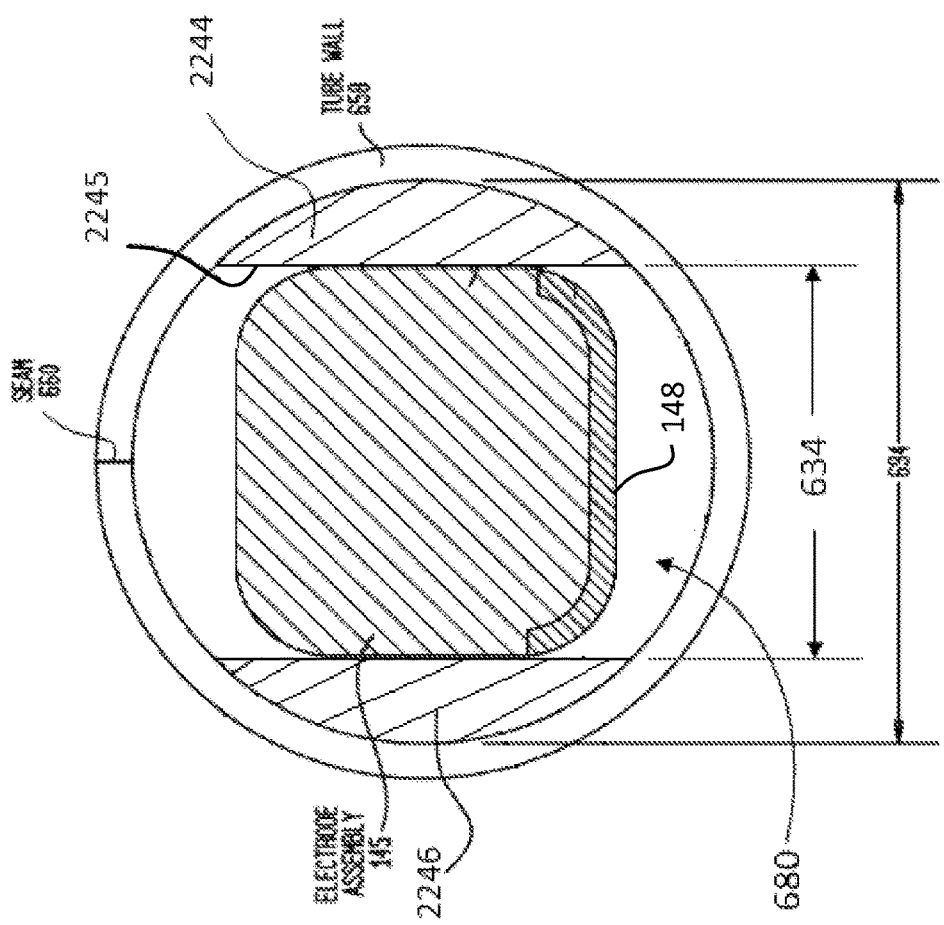

Tube wall 658 in anti-twist section 620 has sections 2244 and 2246 which extend radially inward to form an anti-twist guide channel 680. Specifically, a flat 2244 provides a substantially planar lumen surface along the length of section 620. As shown in the figures, the flat 2244 has a surface 2245 that is substantially planar and which therefore conforms with the substantially planar side of electrode assembly 145. Similarly, flat 2246 has a surface that is substantially planar which conforms with the substantially planar opposite surface of electrode assembly 145 (the referenced surfaces of the assembly are normal to the top surface which has the electrode and the bottom surface, in this embodiment). As shown in FIG. 24, when a distal region of electrode assembly 145 is located in anti-twist section 620, the surfaces of flat 22 and flat 2246 are in physical contact with the respective side surfaces of the electrode assembly. In some embodiments, this prevents the electrode assembly from curving.

Figure 25:
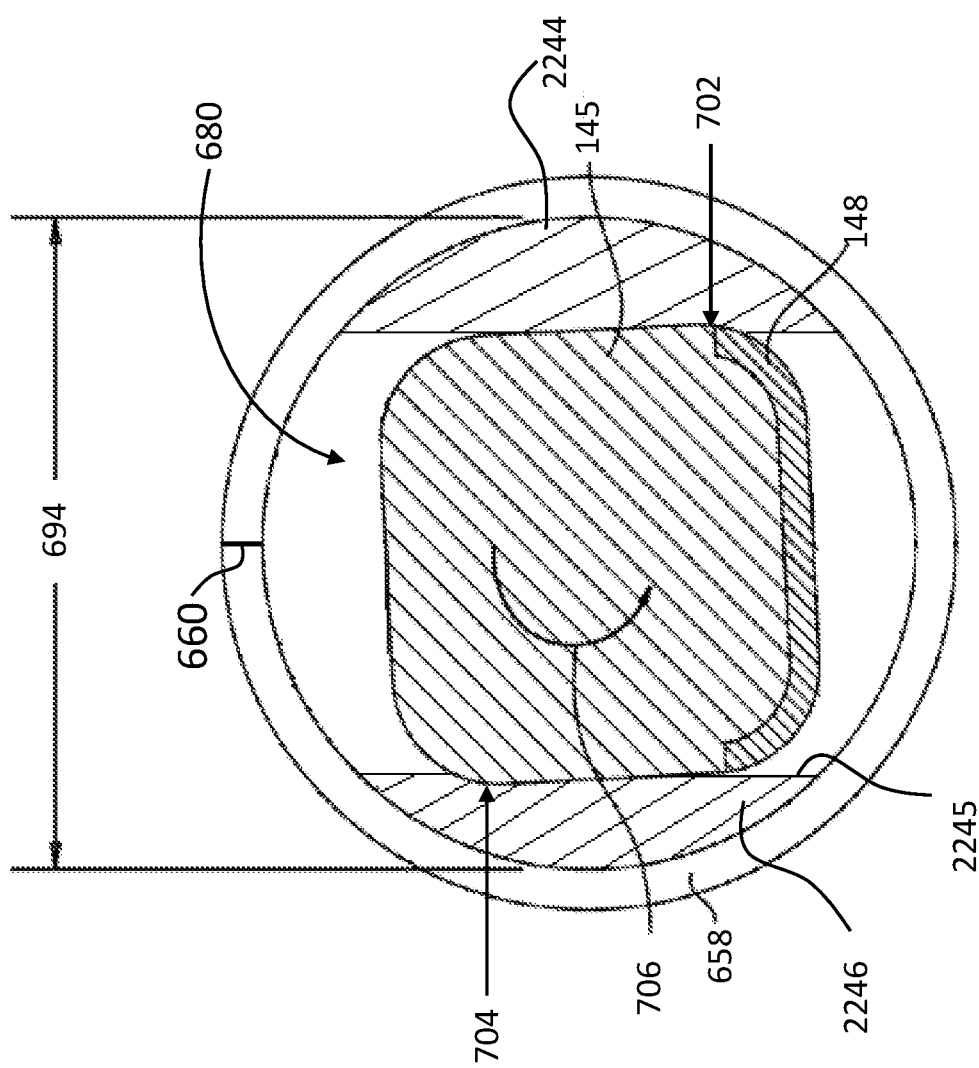

In some embodiments, due to the anti-twist guide channel 680, electrode assembly 145 is unable to twist to relieve the stress caused by the inability of the electrode assembly to assume its pre-curved configuration. This is illustrated in FIG. 25. As shown by arrow 706, electrode assembly 145 is attempting to twist while located in anti-twist section 620. As one surface of the electrode assembly 145 pushes against flat 2244, the flat applies a reactive force 704 to the assembly. Similarly, as the opposite surface of electrode assembly 145 applies a force against flat 2246, that flat applies a reactive force 702 to the assembly. (It is noted that in the embodiment show, the electrodes are located facing away from the seam/slit. In some embodiments, the opposite is the case, and the electrode array is loaded into the tool so that the electrodes instead face the slit/seam, as opposed to being loaded so that they face away therefrom.)

As noted, electrode assemblies are sometimes longitudinally tapered to accommodate the increasingly larger cross-sectional dimensions of an electrode assembly 145 as it passes through anti-twist guide channel 680, insertion guide tube 2210 has a longitudinal seam 660 (also referred to herein as a slit, and, on other embodiments, 660 is a gap). This seam enables insertion tube 2210 to splay open in a manner analogous to that seen in FIG. 7B. Specifically, insertion tube 2210 opens as the vertical distance 690 from bottom surface 652 to top surface 650 of the portion of the assembly in guide channel 680 becomes greater than the distance between the flats.

Once electrode assembly 145 is inserted into cochlea 140, insertion guide tube 610 is retracted over electrode assembly 145. The expanded insertion guide tube 2210 is to be withdrawn from cochlea 140 and therefore is to pass through the cochleostomy, oval or round window. In a round window insertion, for example, splayed insertion guide tube 2210 is to pass through round window aperture 708.

It is noted that while the embodiments detailed herein depict the electrodes of the electrode array facing the slit/gap, in other embodiments, the array is inserted into the guide such that the electrodes face the opposite, and are located furthest away from the slit/gap.

Figure 23:
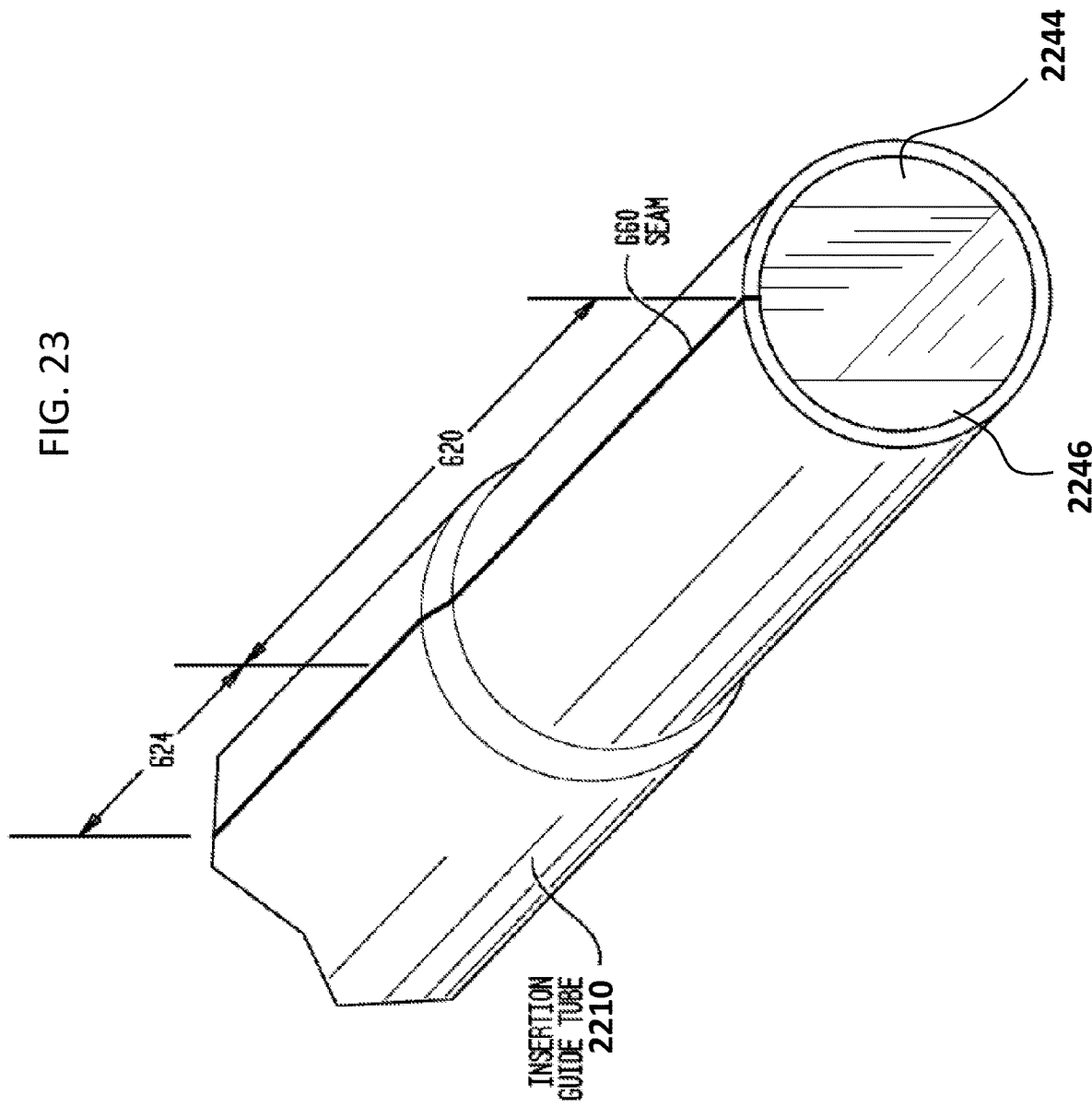

As electrode assembly 145 is advanced through insertion guide tube 2210, the tendency of the assembly to twist decreases. This is due to the increasingly greater portion of the electrode assembly which has been deployed, the relatively larger dimensions of the proximal regions of the assembly, and the relatively smaller bias force in the proximal region as compared to the distal region of the assembly. Thus, as the cross-sectional size of the assembly passing through guide channel 680 increases, the tendency of the electrode assembly to twist decreases. Referring again by analogy to FIG. 7B, as insertion guide tube 610 splays, the respective flats angle away from each other (as opposed to the configuration seen in FIG. 23, where the flats are parallel to one another). Thus, the extent to which the flats prevent the twisting of the electrode assembly decreases with the tendency of the assembly to twist.

Lumen 640 has a height which is greater than the analogous height of the distal region of electrode assembly 145. This space is dimensioned to receive the wider electrode assembly as the larger proximal region passes through guide channel 680.

In anti-twist section 620 there is a minimal gap, if any, between flats 2244, 2246 and electrode assembly 145, thereby enabling anti-twist guide channel 680 to closely control the orientation of the assembly, as noted above. Should a region of electrode assembly 145 located in proximal section 624 be partially twisted relative to a region that is in anti-twist guide channel 680, ramps 2248 (there are two—only one is shown) facilitate the rotation of the assembly as it enters the guide channel. This eliminates the relative twist of this region relative to a more distal region of the assembly. This places the surfaces of the assembly in parallel with the corresponding surfaces of the flats thereby enabling the assembly to continue through anti-twist guide channel 680. In other words, for the assembly to travel through guide channel 680, it is utilitarian for the assembly to be substantially straight. As the assembly travels up the ramps, the ramp facilitates the rotation of the assembly to enable the assembly to enter guide channel 680.

In an exemplary embodiment, insertion guide tube 2210 is made of Nitinol, and the flats comprise silicone molded in the tube. Other materials can be utilized in other embodiments. In some embodiments, the flats and guide tube are unitary. Further, in an exemplary embodiment, the slit and/or gap and/or openings are cut utilizing laser cutting. Any arrangement that can enable the fabrication of embodiments according to the teachings detailed herein can be utilized in at least some exemplary embodiments.

The counter-forces 702, 704 are applied such that the forces are offset from the center of the electrode assembly. In this regard, at least in embodiments where the cross-sectional shape of the electrode assembly is not perfectly circular, flats 2244, 2246 can impart a counter-force to the electrode assembly without substantially relying on friction between the assembly and flats. Such may be the case for electrode assemblies having an elliptical cross-section or the like, etc.

In an exemplary embodiment, the guide is configured such that, for at least some electrode arrays there is a method of insertion of the electrode array such that the electrode array is a perimodal array/a curly/curved array, and the array is straightened while in the tube of the guide, and thus is in a non-relaxed state. In an exemplary embodiment, an amount of twist about the longitudinal axis at a given location of the electrode array along the longitudinal axis of the electrode array at locations within the tube while in the tube is no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 degrees. In an exemplary embodiment, for a location on an imaginary plane normal to a longitudinal axis of the array and on a surface thereof, the location does not change by more than any of the aforementioned angles. In an exemplary embodiment, the aforementioned phenomenon can be measured by, for example, creating imaginary planes that are normal to the longitudinal axis, which planes are located every 0.5, 1, 1.5, 2, 2.5, 3, 3.5, 4, 4.5, 5, 5.5, 6, 6.5, 7, 7.5, 8, 8.5, 9, 9.5 or 10, 11, 12, 13, 14, 15, 16, 17, 18, 19, or 20 mm or any value or range of values therebetween in 0.1 mm increments. The locations can be scribed or otherwise identified, and then the tube can be bent according to the angles detailed herein, and then the rotation at these locations relative to the longitudinal axis can be compared to that which was the case prior to insertion into the tube. It is noted that in at least some exemplary embodiments, twisting at one location can be compared to twisting at another, similarly situated location, along the array. Again, two or three or four more different planes can be compared to one another, and the relative change from one to the other can be evaluated. In this regard, the aforementioned consistencies can be present over two or three or four or five or six or seven or eight or nine or 10 or 11 or 12 or 13 or 14 or 15 or 16 or 17 or 18 or 19 or 20 of the planes spaced as noted above, the limiting factor being the length of the array. It is noted that embodiments include methods of insertion that meet the aforementioned movement requirements for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more locations, which locations can be spaced according to the plane locations detailed above, the limiting factor being the length of the array.

It is noted that the aforementioned twisting/rotation features can be measured relative to a location along the longitudinal direction of the tube. By way of example only and not by way of limitation, any of the aforementioned rotation/twisting features can be measured at a location on the electrode array that is located, relative to, for example, a plane that lies on the most distal location and/or the most proximal location of the flats and/or the anti-rotation clip (described below) and/or a plane that lies in between these aforementioned locations, such as about 30, 35, 40, 45, 50, 55, 60, 65, 70 percent of the distance between these locations (forward and/or rearward). In an exemplary embodiment, the length of the clip can be more than, less than and/or about equal to 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 2.7, 3.8, 3.9 or 4.0 mm or any value or range of values therebetween in 0.01 mm increments.

In an exemplary embodiment, the clip increases a clamping force against the sides of the electrode array by at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 2.7, 3.8, 3.9, 4.0, 4.5, 5.0, 5.5, 6.0, 6.5, 7.0, 7.5, 8.0, 9.0, 10, 11, 12, 13, 14, 15, 16, 17, 18, 19 or 20 or more times relative to that which would be the case in the absence of the clip, all other things being equal.

It is noted that in at least some exemplary embodiments, the guide is configured so that the array can bow with respect to a plane extending from the top to the bottom of the tube. In this regard, in an exemplary embodiment, the electrode array is permitted some curvature when in the tube. In this regard, with reference to FIG. 24, it can be seen that there is space above and below the electrode array. In an exemplary embodiment, this enables the electrode array to bow a bit in that direction, while preventing the electrode array to bow to the left or right (at least when in the flats location). Accordingly, in an exemplary embodiment, while the electrode array is in the tube, with respect to portions of the array in the flats area, the array bows laterally upward and/or downward by an amount more than, less than or equal to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 degrees or any value or range of values therebetween in increments of 0.1 degrees. by way of example only and not by way of limitation, in an exemplary embodiment, utilizing the local longitudinal axis of the electrode array at the beginning of the flats as the reference, the longitudinal axis of the electrode array at the end of the flats and/or midway or at a location between, such as about 30, 35, 40, 45, 50, 55, 60, 65, 70 percent of the distance between these locations at the flats would be off by the aforementioned amounts. Note also that the differences between the two can change as the electrode array is driven through the tube. By way of example only and not by way of limitation, when the tip of the electrode array is flush with the most distal portion of the flats, the bowing could be larger than that which is the case after three or four or five or six or seven or eight or nine or ten electrodes have moved out of the tube. Accordingly, embodiments exist where any of the aforementioned values exist for an electrode array where any of the number of electrodes have moved out of the tube.

Conversely, it is noted that in an exemplary embodiment, the array bows laterally left word and right word by an amount no more than 0.25, 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 degrees, as measured according to any of the measurements detailed above.

Alternatively, and/or in addition to the above, the tube can be configured such that it has a pre-curved/pre-bent shape when in the relaxed state. In this regard, in an exemplary embodiment, such a tube can allow the array to curve/bow in the plane detailed above by the aforementioned amounts. Accordingly, in an exemplary embodiment, the tube is configured such that, in its relaxed state, the tube bends in the bottom-top plane by an amount more than, less than or equal to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 degrees or any value or range of values therebetween in increments of 0.1 degrees, as measured between two locations that are greater than or about equal to 15, 16, 17, 18, 19, 20, 21, 22, 23, 24, 25, 26, 27, 28, 29, 30, 31, 32, 33, 34, 35, 36, 37, 38, 39, or 40 mm away from each other or any value or range of values therebetween in 1 mm increments. That said, in an exemplary embodiment, the tube can be configured to curve or otherwise bow when loaded by any of the aforementioned amounts. That is, in an exemplary embodiment, in the relaxed state, the tube can be straight, but when loaded with an electrode array, the tube can bow in the top bottom plane. In an exemplary embodiment, when loaded, the tube can bow in the top bottom plane by an amount more than, less than or equal to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 degrees or any value or range of values therebetween in increments of 0.1 degrees, as measured between two locations that are greater than or about equal to 15, 16, 17, 18, 19, 20, 21, 22, 23, 24, 25, 26, 27, 28, 29, 30, 31, 32, 33, 34, 35, 36, 37, 38, 39, or 40 mm away from each other or any value or range of values therebetween in 1 mm increments.

With reference to FIG. 25, in an exemplary embodiment, the tube and array arrangement are configured such that a counter torque of any value from 0.05 Newton-meters (Nm) to 15 or more Nm on 0.05 Nm increments is applied to the electrode array. In an exemplary embodiment, the tube and array arrangement are configured such that a counter torque of at least or no more than or any value from 0.05 Newton-meters (Nm) to 15 or more Nm on 0.05 Nm increments is applied to the electrode array. Thus, the tube can be configured to provide a counter-torque from between 0.05 Nm to 15 Nm or any value or range of values therebetween in 0.05 Nm increments.

To be clear, in an exemplary embodiment, the electrode array is an array that has, in its relaxed state, a curvature of at least 45, 50, 55, 60, 65, 70, 75, 80, 85, 90, 95, 100, 110, 120, 130, 140, 150, 160, 170, 180 or more degrees, as measured based on two local longitudinal axes at two spaced away locations, such as locations according to any of those detailed herein. That said, some embodiments include the utilization of the insertion guide on a straight array.

Figure 32:
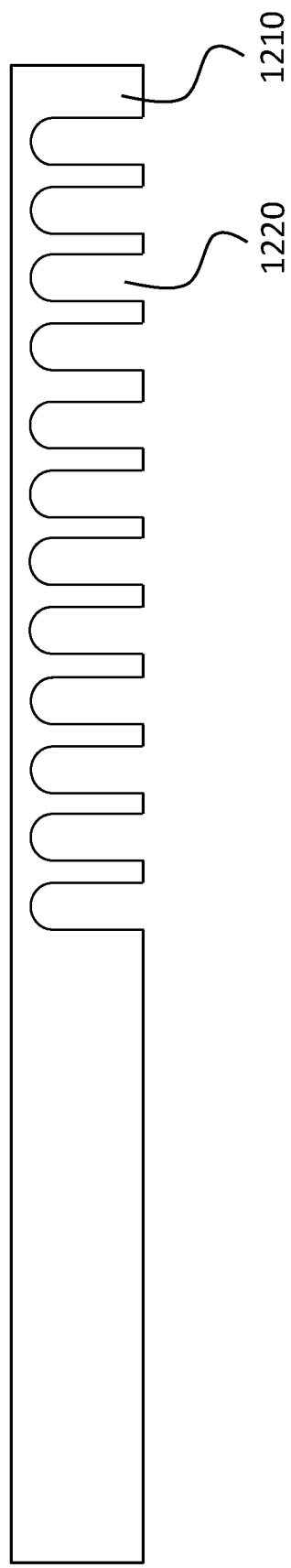
FIG. 32 presents another schematic of an exemplary feature of an insertion tube according to an exemplary embodiment.

While many of the embodiments described above presented openings bounded by surfaces at 90° angles, in some other embodiments, the openings are bounded at least in part by curved surfaces. In this regard, FIG. 32 depicts an exemplary embodiment of openings where the uppermost portions are curved instead of flat. In an exemplary embodiment, the openings have large radii. In an exemplary embodiment, the radii is at least half of the width of the opening while in other embodiments, the answer circular having radii that is larger than at least half the width of the opening.

In an exemplary embodiment, the tube is configured to enable bending more in one lateral plane than in another lateral plane normal thereto. By way of example only and not by way of limitation, with respect to bending in the lateral plane that extends from top to bottom (the plane depicted in FIG. 21A, where the slit/gap is eclipsed by the body of the tube), a force applied at the tip of the tube in a direction in the plane that extends from top to bottom will bend the tube a certain number of degrees upward and/or downward, and the same magnitude of force applied at the tip of the tube in a direction in the plane that extends from left to right (normal to the top-bottom plane/normal to the plane of FIG. 21A) will bend the tube less number of degrees, all other things being equal. In an exemplary embodiment, the tube is configured such that a respective first force must be applied at the tip in the top bottom plane to achieve 5, 6, 7, 8, 9, 10, 15, 20, 25, 30, 35 or 40 degrees of bending in top-bottom plane, and respective second force that is at least 2, 3, 4, 5, 6, 7, 8, 9, 10, 11, 12, 13, 14, 15, 16, 17, 18, 19 or 20 times or more the first force must be applied in the left-right plane to achieve the comparable degrees of bending. Thus, it can be seen that in at least some exemplary embodiments, the tube is more resistant to bending in the left-right plane than it is in the bottom-top plane.

Figure 26:
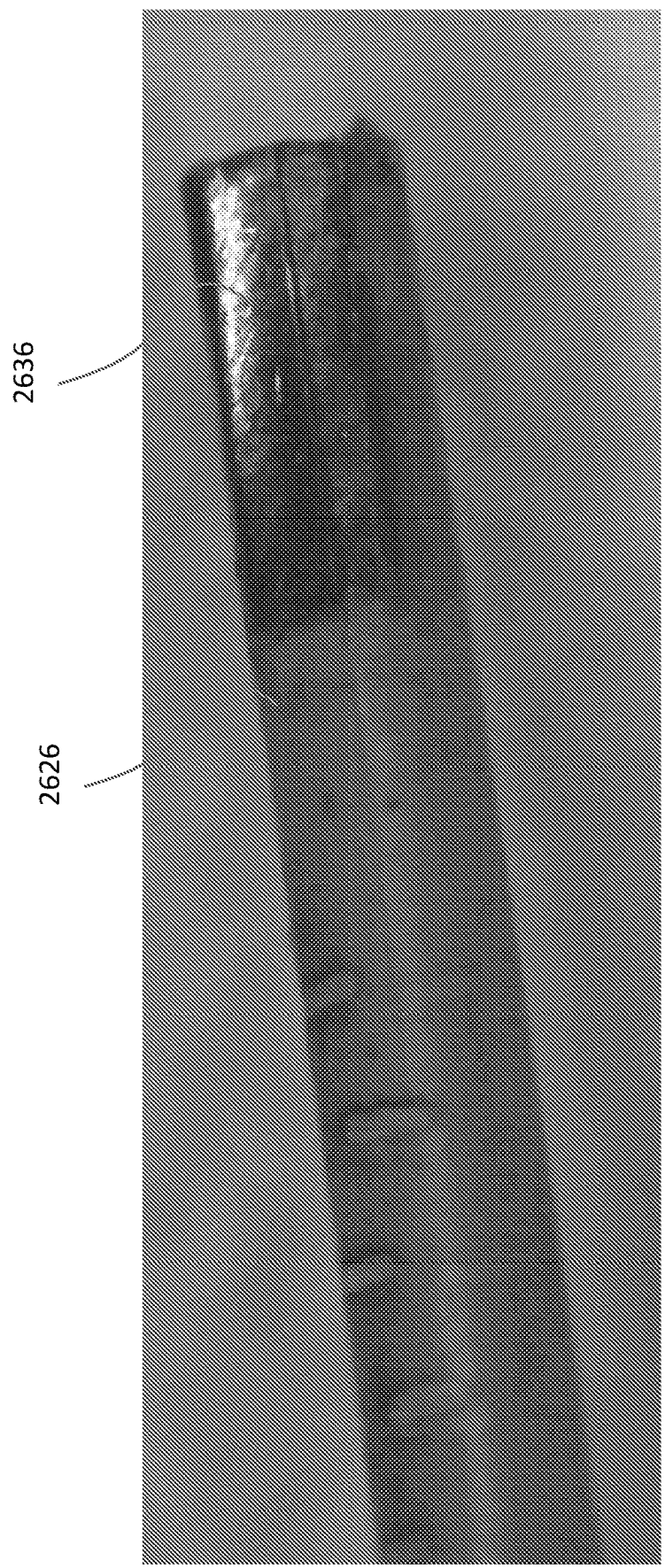
Figure 27:
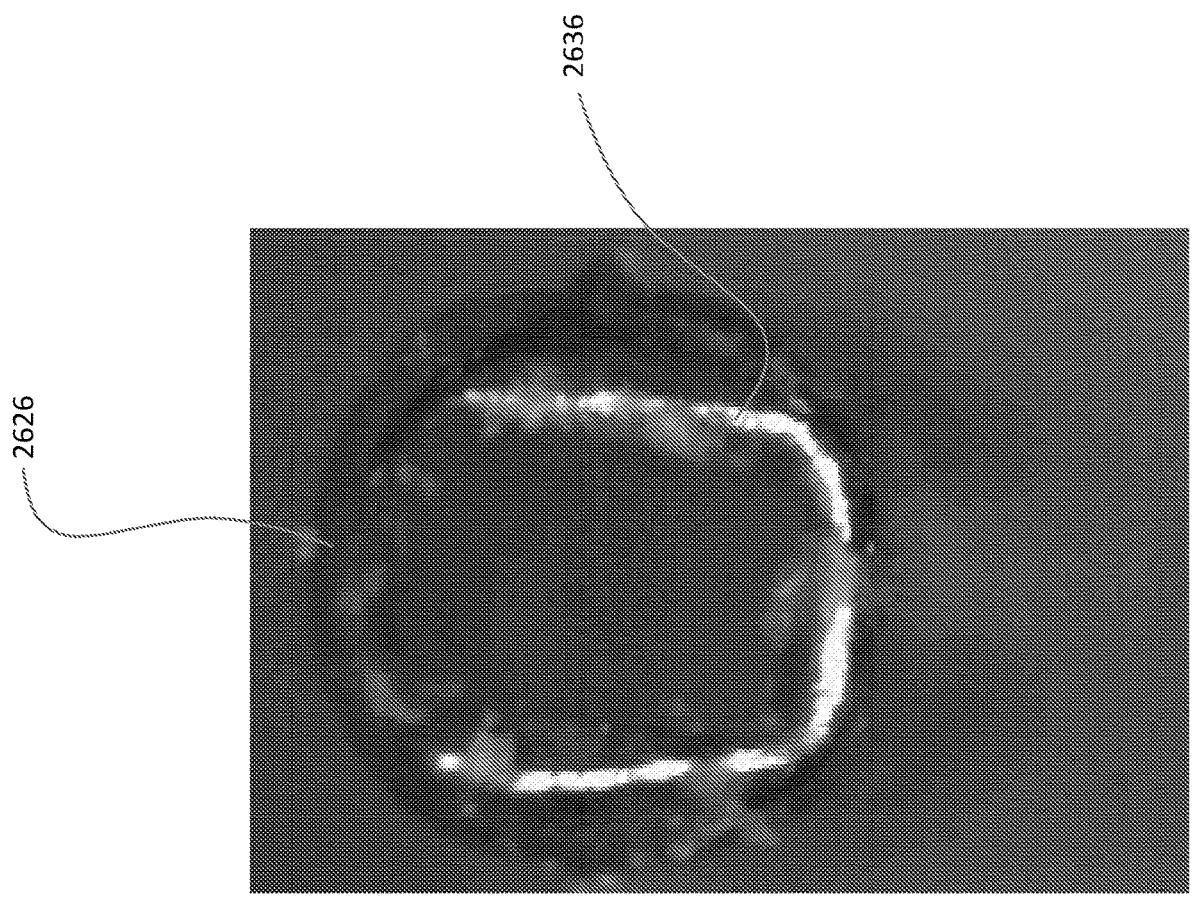
Figure 31:
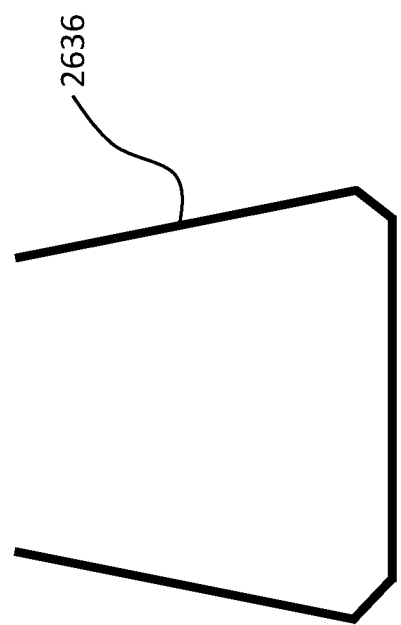

FIGS. 26 and 31 depict an alternate exemplary embodiment where the flats, or at least the functionality of the flats, is achieved by a clip 2636 that is embedded in the polymer establishing the guide 2626. It is noted that this embodiment can be utilized with the Nitinol embodiments of the guide tube as well. In an embodiment, the clip is a spring clip. In an exemplary embodiment, the clip is molded into the flats (and/or into the tube) and increases the clamping force and makes the clamping force more independent to the slits flats.

Figure 28:
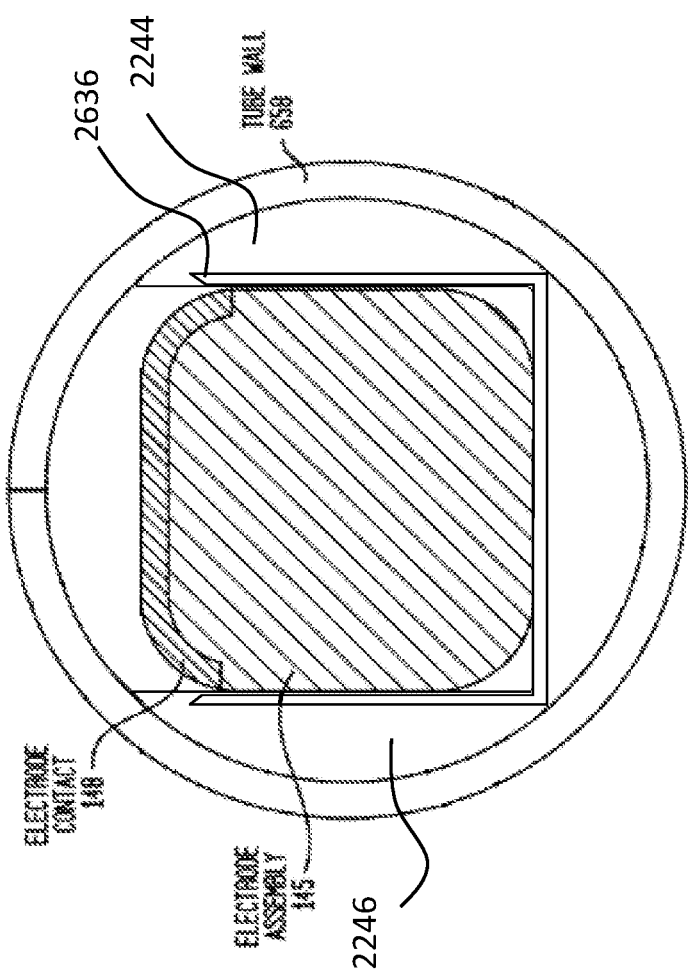
Figure 29:
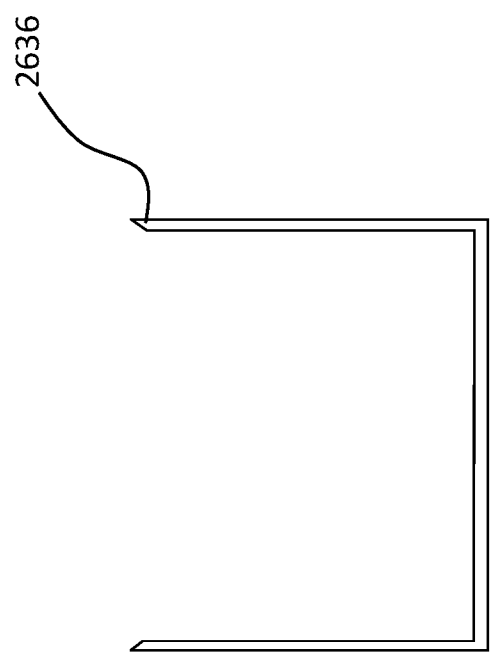

FIG. 29 depicts another exemplary embodiment of the clip 2636, and FIG. 28 depicts the embodiment of FIG. 29 partially embedded in the flats, where the inboard surfaces of the clip are exposed to the electrode assembly 145. In some embodiments, the inboard surfaces of the clip are treated with a substance that reduces friction. That said, in an alternate embodiment, the clip is entirely embedded in the flats and/or in the tube, such that material of the flats is interposed between the clip and the electrode assembly. The embodiment of FIG. 28 shows that the flats also have a contiguous component that extends along the bottom from flat 2244 to flat 2246. In an exemplary embodiment, this establishes a U shape, which supports the clip.

Figure 30:
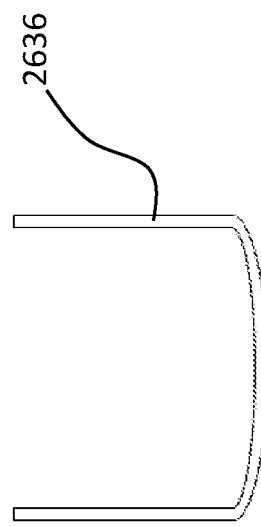

FIG. 30 depicts an alternate embodiment of the clip 2636, where the clip has a rounded bottom surface. In an exemplary embodiment, the legs of the clip are the portions that apply force to the electrode assembly. The cross member of the clip that holds the legs in place does not provide a supporting function for the array.

FIG. 31 depicts an alternate embodiment of a clip 2636. Here, the legs of the clip are canted inward in a relaxed state. In this exemplary embodiment, the clip provides for the increasing diameter of the electrode assembly without stressing too greatly the cross bottom that holds the legs in place. In this regard, as the electrode array extends through the clip, and thus the diameter of the electrode array gets larger, the legs will bend from the inward canted arrangement to a parallel arrangement and then potentially to an outboard canted arrangement. This as opposed to, in some embodiments, the clip always bending outward from the parallel state.

Note that in an exemplary embodiment, the clip does not bend or otherwise bends relatively little. In this regard, in an exemplary embodiment, a flexible material is located over the inboard portions of the legs (e.g., the flat material), and this material compresses to a degree that is greater than the deflection of the legs, if any. Thus, the clip maintains the compression force against the electrode array, and the material of the flats provide the "give" as the array widens.

In an exemplary embodiment, the portion of the tube that extends past the stop 204 is longer than some of the embodiments detailed above. In an exemplary embodiment, the distance from the front face of the stop 204 to the most distal end of the tube is less than, more than or about equal to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mm or more or any values or range of values therebetween in 0.1 mm increments (e.g., about 22.4 mm, 28.1 mm, 15.1 to 39.3 mm, about 15.1 to about 39.3 mm, etc.). In an exemplary embodiment, the tube can be configured such that the angle of total bending (from the front face of the stop to the tip) the tube can subtend an angle that is less than, more than or about equal to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 80, 90, 100, 110, 120, 130, 140, 150, 160, 170, 180, 190, 200, 225, 250, 275, 300, 325, 350, 375, 400, 425, 450 degrees or more or any values or range of values therebetween in 1 degree increments, and such can meet one or more or all of the above noted features herein.

Figure 33:
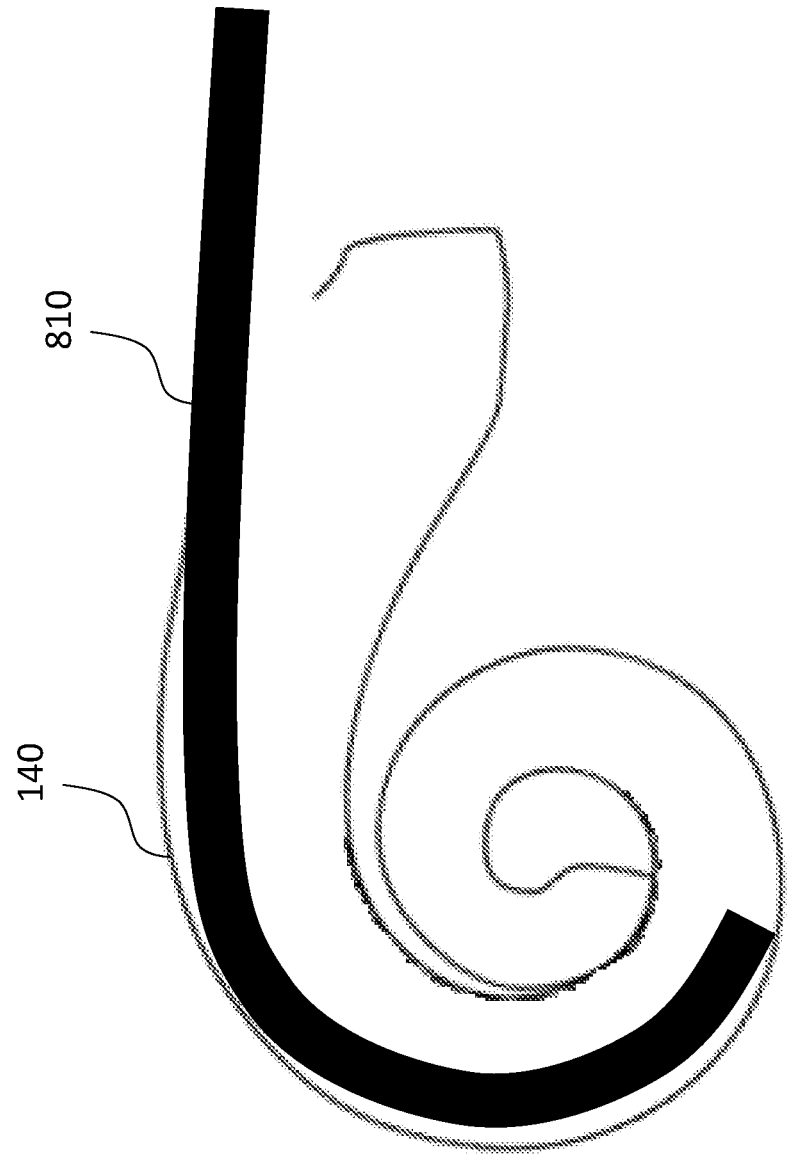
FIGS. 33-35 present some additional schematics of an insertion tube inserted in a cochlea.
Figure 34:
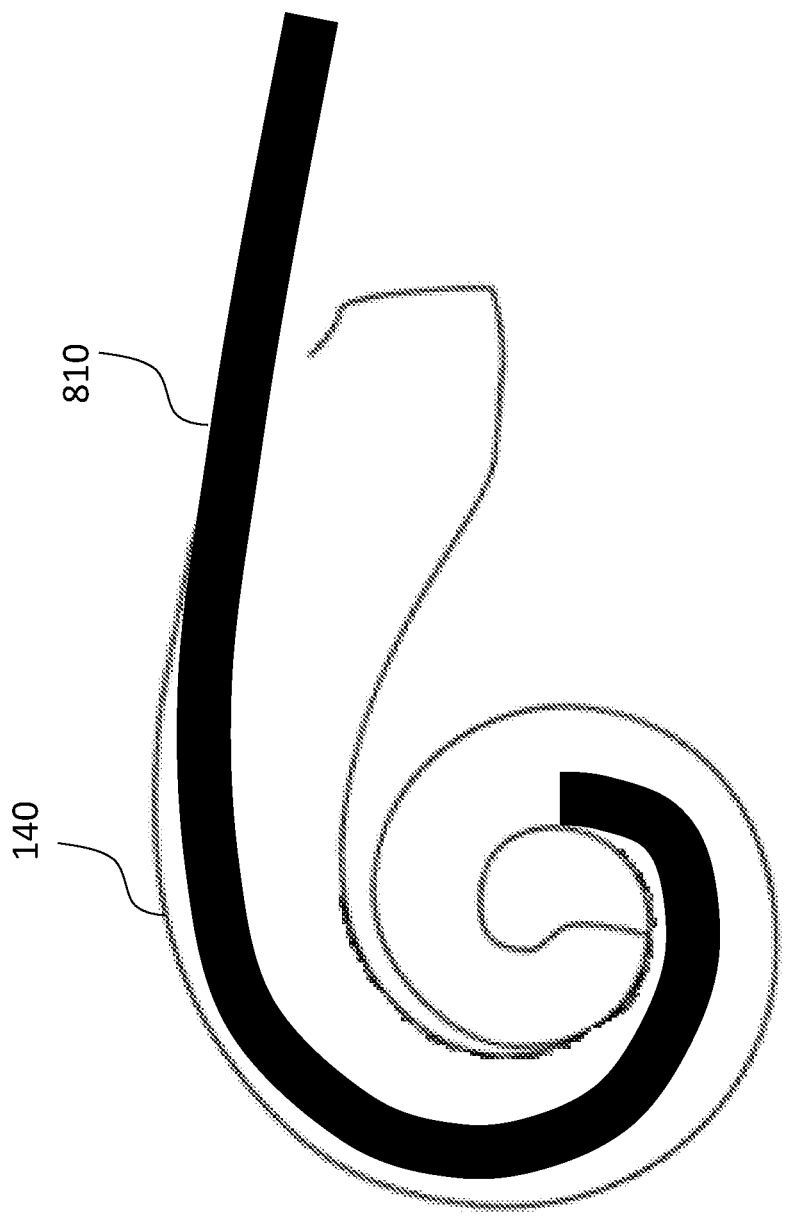
Figure 35:
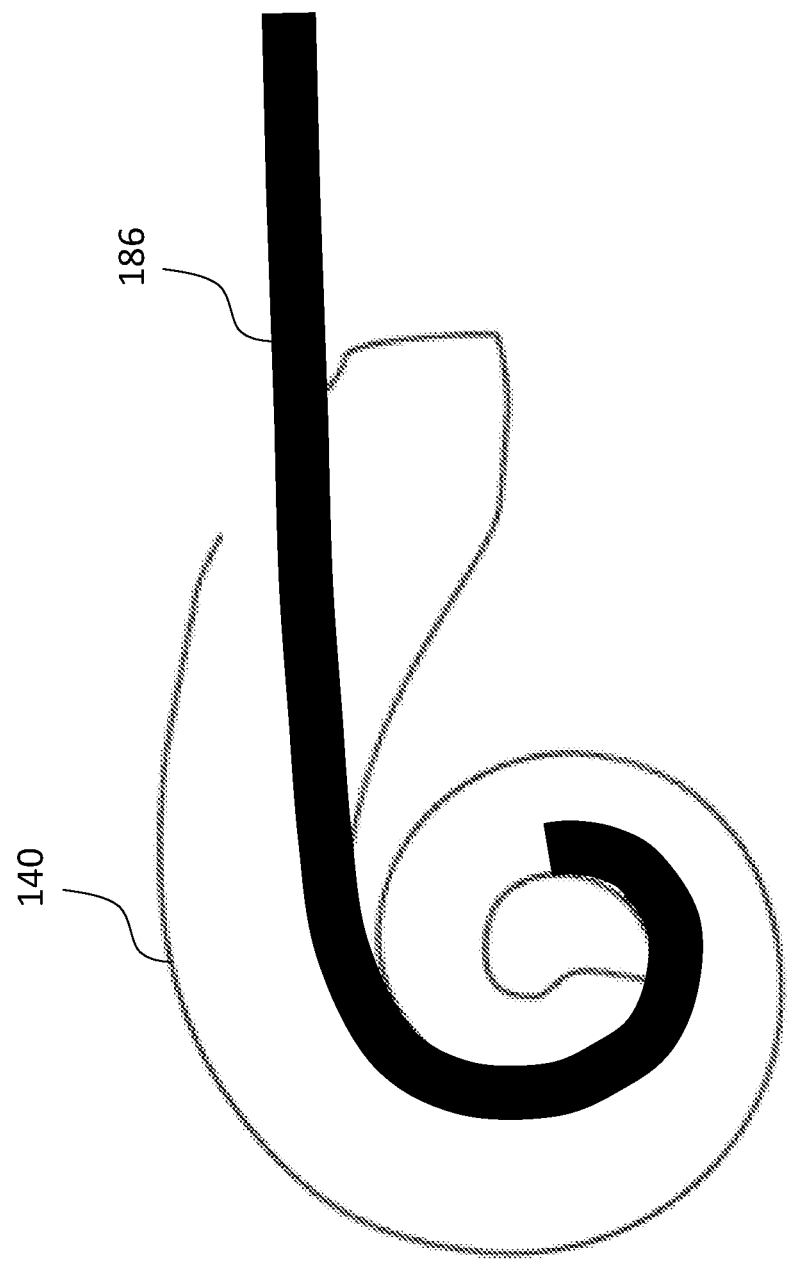

FIGS. 33, 34, and 35 present some diagrams of flexible tubes 810 inserted into a cochlea that subtend an angle of more than 150 degrees. FIG. 33 presents a lateral wall array insertion tube, FIG. 35 presents a perimodiolar array insertion tube, and FIG. 34 presents a tube that is for a perimodiolar array, but bends in a less aggressive manner.

Figure 36:
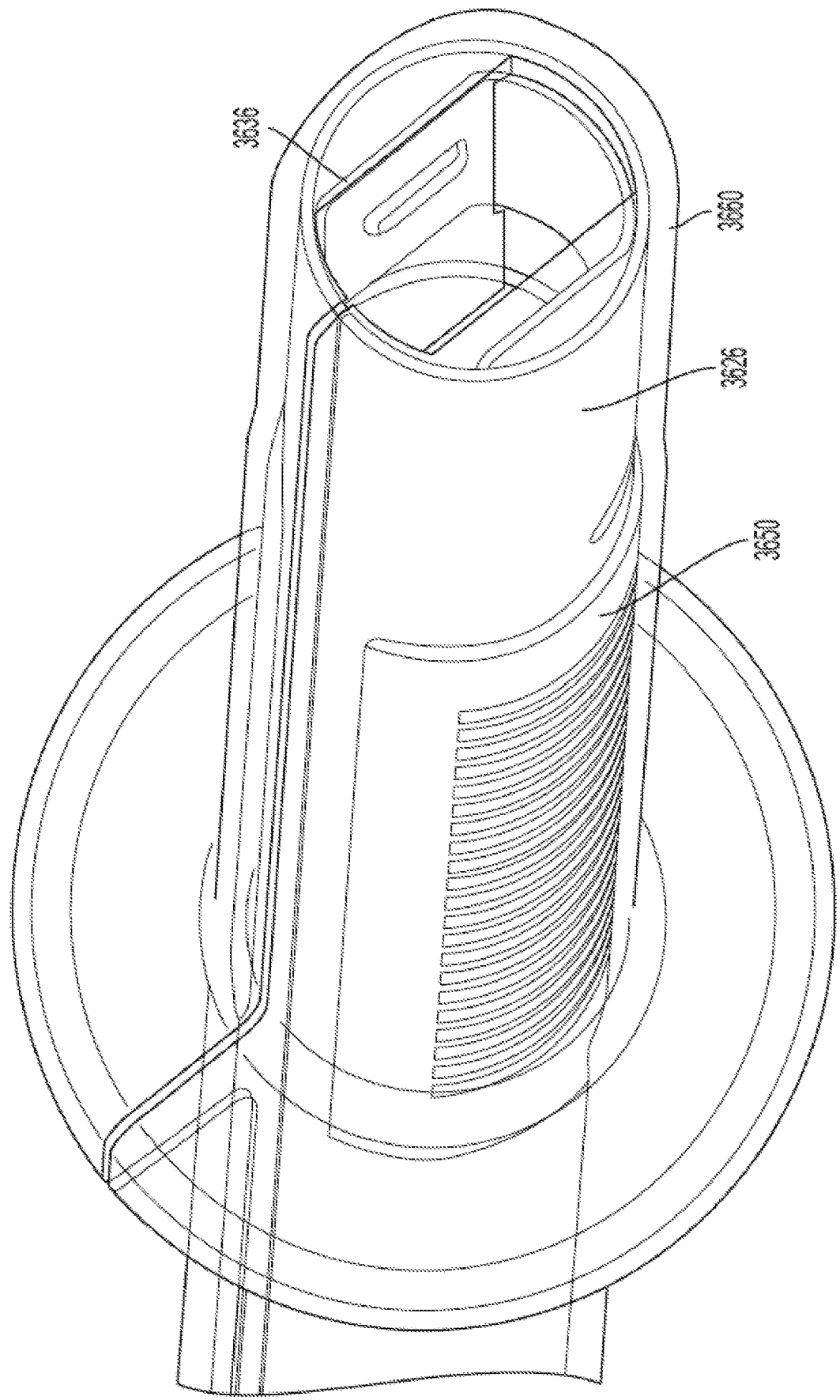
FIGS. 36 and 37 present additional schematics of exemplary features of exemplary insertion tools.
Figure 37:
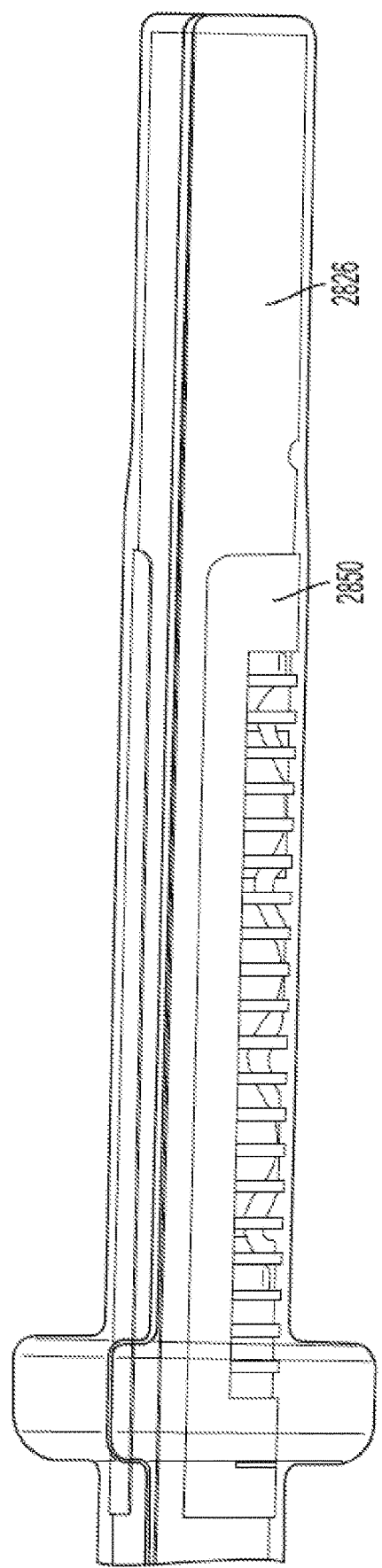

FIGS. 36 and 37 depict an alternate embodiment where the guide 3626 is made out of a polymer. As can be seen, a U-shaped spring clip 3636 is located inside the guide 3626, although it is noted that this configuration can be the case in an embodiment where the guide is made out of a metal and/or metal alloy, etc. Also, as can be seen, a strengthening member 3650 is located about the guide 3626. The strengthening member 3650 can correspond to a portion of the guides detailed above, having the openings therein as detailed above. In an exemplary embodiment, the tube 3626 can have the openings to enable increased bending at certain areas and the strengthening portion 3650 provides for localized strengthening relative to other locations. In an exemplary embodiment, member 3650 resists potential collapsing of the tube 3626 when the tube 3626 is flexed/bent by one or more of the above noted angles. Indeed, in an exemplary embodiment, member 3650 can be used to obtain the relatively straight sections in FIGS. 33, 34 and 35, and the absence of member 3650 will enable the tube to bend the above-noted angles, depending on the embodiment. In an exemplary embodiment, strengthening member 3650 limits the amount of interior diameter reduction by any one or more of the aforementioned percentages. In the embodiment of FIG. 36, the various components are at least partially encapsulated by a silicone barrier 3660, which, in some embodiments, can hold the various components relative to each other (to the extent that silicone holds components relative to each other). It is noted that the silicone encapsulation can be used with respect to the metal/metal alloy tube embodiment as well.

In view of the above, it can be seen that in an exemplary embodiment, there is a device, wherein at least a portion of the guide that is flexible is made of a polymer body reinforced with a metal-based material, or at least a stiffer body. Also, as can be seen above, in an exemplary embodiment, there is a device where the guide includes at least a first part and a second part, wherein the first part is configured to enable the array to flex beyond that which would be the case if the first part was the same as the second part, and the second part is configured to maintain the pre-curved electrode assembly in a substantially straight configuration while preventing the electrode assembly from twisting in response to stresses induced by bias forces which urge the assembly to return to its pre-curved configuration, when the insertion guide is flexibly bent in the plane. By way of example only and not by way of limitation, in an exemplary embodiment, the proximal section 624 of the insertion guide tube can enable the electrode array to flex beyond that which is the case in the anti-twist section 620. In an exemplary embodiment, the electrode array can flex/bend such that relative angles of the local longitudinal axis of the array can have a difference from each other in the proximal section (such as the maximum relative angle) that less than, more than, or about equal to 110, 115, 120, 125, 130, 135, 140, 145, 150, 155, 160, 165, 170, 175, 180, 185, 190, 195, 200, 210, 220, 230, 240, 250, 260, 270, 280, 290, 300, 325, 350, 375, 400, 450, 500, 550, 600, 650, 700, 750, 800, 850, 900, 1000, 1100, 1250, 1500 percent or more or any value or range of values therebetween in 1% increments than relative angles (such as the maximum relative angle) of the local longitudinal axis of the array in the anti-twist section.

Also, in an exemplary embodiment, there is a device, wherein the guide includes at least a first part and a second part, the first part being configured to enable the array to twist beyond that which would be the case if the first part was the same as the second part and the second part is configured to maintain the pre-curved electrode assembly in a substantially straight configuration while preventing the electrode assembly from twisting in response to stresses induced by bias forces which urge the assembly to return to its pre-curved configuration, when the insertion guide is flexibly bent in the plane. In an exemplary embodiment, the electrode array can twist such that relative angles about the local longitudinal axis of the array can have a difference from each other in the proximal section (such as the maximum relative angle) that less than, more than, or about equal to 110, 115, 120, 125, 130, 135, 140, 145, 150, 155, 160, 165, 170, 175, 180, 185, 190, 195, 200, 210, 220, 230, 240, 250, 260, 270, 280, 290, 300, 325, 350, 375, 400, 450, 500, 550, 600, 650, 700, 750, 800, 850, 900, 1000, 1100, 1250, 1500 percent or more or any value or range of values therebetween in 1% increments than relative angles (such as the maximum relative angle) about the local longitudinal axis of the array in the anti-twist section.

Figure 38:
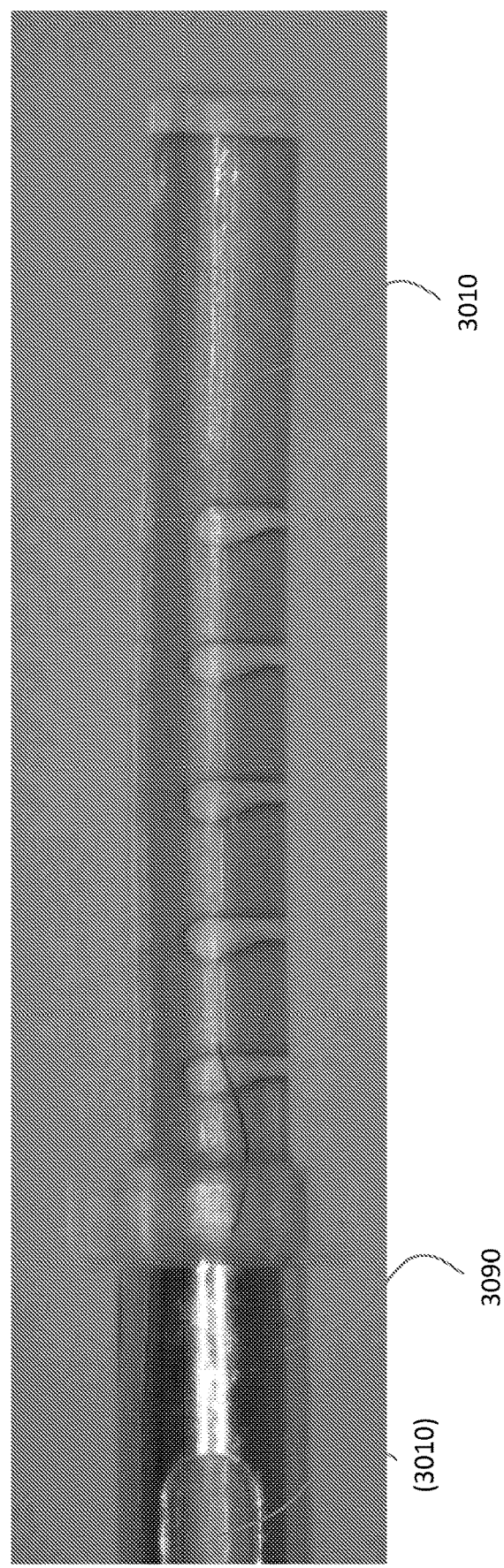
FIG. 38 presents another exemplary embodiment of an insertion tool.

FIG. 38 presents another exemplary embodiment of a guide 3010 having openings. As can be seen, here, a metal support body 3090/a support body that is at least 2, 3, 4, 5, 6, 7, 8, 9, 10, 11, 12, 13, 14, or 15 times as stiff as the tube, all other things being equal.

It is noted that at least some exemplary embodiments of the teachings detailed herein include methods of inserting an electrode array, such as a perimodiolar array and/or a lateral wall array and/or a mid-scala array, into a cochlea, using an insertion tool having at least one or more of the features disclosed herein. Further, in an exemplary embodiment, the methods results in an electrode array having a final perimodiolar position, a mid-scala position or a lateral wall position, within the cochlea. In an exemplary embodiment, the insertion methods include utilizing a tool such that any one or more of the functionalities of the tool detailed herein occurred during the method. By way of example only and not by way of limitation, the aforementioned bendings having one or more of the aforementioned angles can occur. By way of example only and not by way of limitation, the tube placement in the cochlea according to FIGS. 33-35 can occur. By way of example only and not by way of limitation, the aforementioned displacements of various components of the tube can occur during the method. Still further, in an exemplary embodiment, the insertion methods include utilizing a tool such that any one or more of the positional and/or performance features of the array occur. By way of example only and not by way of limitation, in an exemplary embodiment, the array is limited in twisting and/or flexing according to the various teachings detailed herein.

Figure 39:
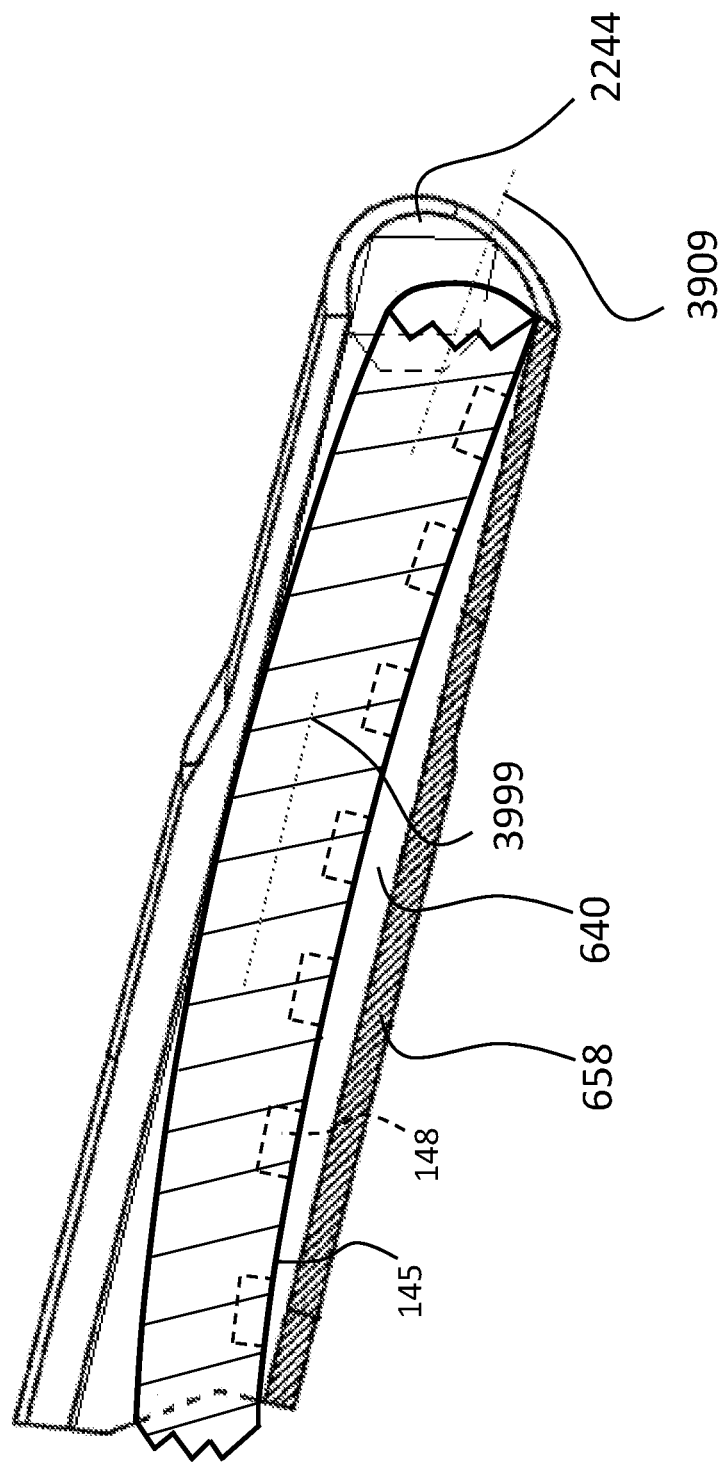
FIG. 39 presents another exemplary embodiment depicting a use of the insertion tool.

In an exemplary embodiment, it is noted that in some instances, there is space between the electrode array and the walls of the insertion to in general, and the channel of the tube in particular. This is seen by way of example only and not by way of limitation, in FIG. 39, which depicts the electrode array 145 inside the channel 640 of an insertion tube. As can be seen, the electrode array 145 is bowed and otherwise has a slight curvature. This is because, in an exemplary embodiment, the electrode array is not held exactly straight as there is clearance along the height along all of its length and in the width of the electrode array except for the area of the flats where it is reduced to control for the twisting. Thus, because of the clearance, the electrode array can bow, at least due to the pre-curved features thereof. An exemplary embodiment utilizes this slight curvature of the electrode to produce a larger moment arm with which to react the tendency to twist than that which can be achieved by using features of the cross section of the electrode. Because the electrode array is not completely straight, it is harder (requires more force) to twist. Thus, this adds in the anti-twisting goal. Also, in some embodiments, this requirement for more force is such that this results in the opening of the flats because of the slit/seam in the tube, in some embodiments. (It is also noted that the embodiment of FIG. 39 depicts the alternate insertion regime where the electrodes 148 are facing away from the slit.)

It is noted that in at least some embodiments, the electrode array is tapered, and a width and/or a height thereof and gradually or step wisely increase with location away from the distal tip. Accordingly, the aforementioned clearances away from the flats can vary for a channel that has uniform internal dimensions. It is noted that in an exemplary embodiment, the aforementioned clearance can be any value or range of values between 0.1 mm and 8 mm, collectively (on a plane normal to the longitudinal axis of the insertion tool on either side of the array) in 0.01 mm increments (e.g., 0.22 mm to 7.78 mm, etc.) for a given location relative to the electrode array. In an exemplary embodiment, the mean, median and/or mode collective clearance over a distance of 1, 1.5, 2, 2.5, 3, 3.5, 4, 4.5, 5, 5.5, 6, 6.5, 7, 7.5, 8, 9, 10, 11, 12, 13, 14, 15, 16, 17, 18, 19 or 20 mm can be any of the aforementioned values just detailed.

In an exemplary embodiment, with respect to two locations along the length of the electrode array, the insertion tool is configured to enable the electrode array to bow within the tube, as measured at a given location within the channel, such as the location of the beginning of the flats, as represented by axis 3909, relative to a longitudinal axis of the electrode array with respect to location along the array where the electrode array extends in a parallel direction of the channel, as is represented by axis 3999, by at least and/or no more than 1, 2, 3, 4, 5, 6, 7, 8, 9, 10, 11, 12, 13, 14, 15, 16, 17, 18, 19, 20, 21, 22, 23, 24, 25, 30, 35 or 40 degrees or any value or range of values therebetween in 0.1 degree increments. In an exemplary embodiment, these aforementioned angles can be measured at the location where the array is parallel with the channel and any location 1, 1.5, 2, 2.5, 3, 3.5, 4, 4.5, 5, 5.5, 6, 6.5, 7, 7.5, 8, 9, 10, 11, 12, 13, 14, 15, 16, 17, 18, 19 or 20 mm away therefrom.

In an exemplary embodiment, a torque that must be imparted on to the electrode array to twist the electrode array 10 degrees about the longitudinal axis thereof is at least 10, 15, 20, 25, 30, 35, 40, 45, 50, 60, 70, 80, 90, 100, 125, 150, 175, 200, 250, 275, 300, 325, 350, 375 or 400 percent greater due to the bowing relative to that which be the case if the electrode array was perfectly straight within the channel, all other things being equal.

In an exemplary embodiment, the bowing of the array in the channel is somewhat analogous to how a hand auger or a hand drill works, where one handle is offset from the drill bit so that one hand creates a torque to turn the drill bit as the handle is moved in a circular orbit about the drill bit longitudinal axis. Here, this works in reverse, where the wall portion that the electrode array (e.g., the top portion as seen in FIG. 39), combined with the friction thereof, provides a torque against movement (analogous to the offset handle and a person's hand being used to prevent the drill bit from turning—the offset provides greater resistance against a rotation relative to that which would be the case if the handle was in line/coaxial with the bit).

FIG. 38 presents another exemplary embodiment of a guide 3010 having openings. As can be seen, here, a metal support body 3090/a support body that is at least 2, 3, 4, 5, 6, 7, 8, 9, 10, 11, 12, 13, 14, or 15 times as stiff as the tube, all other things being equal. In an exemplary embodiment, the arrangement detailed in FIG. 39 variations thereof provide a counter torque against twisting of any of the results detailed above.

Figure 40:
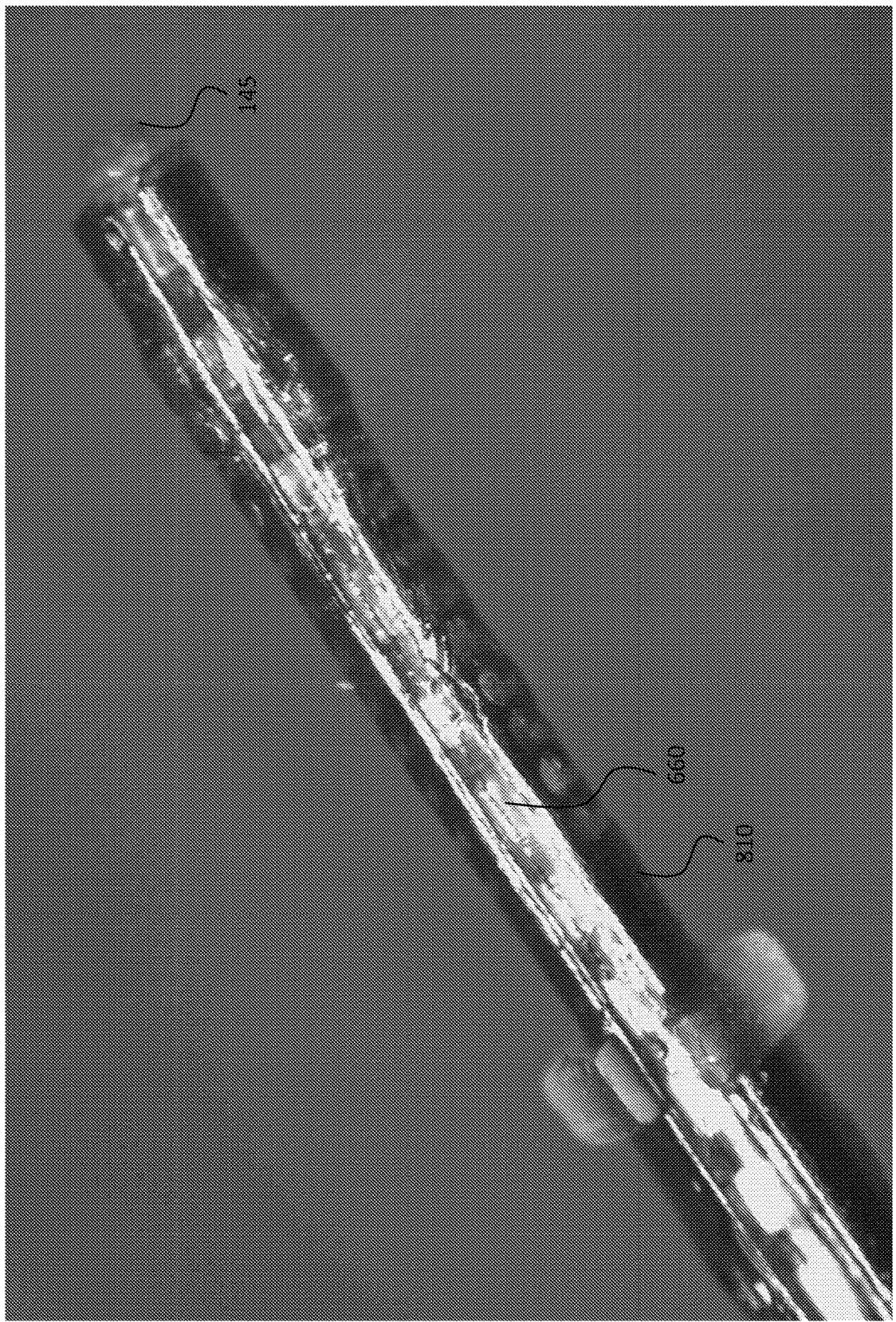
FIGS. 40 and 41 depict some additional exemplary embodiments depicting a use of the insertion tool.
Figure 41:
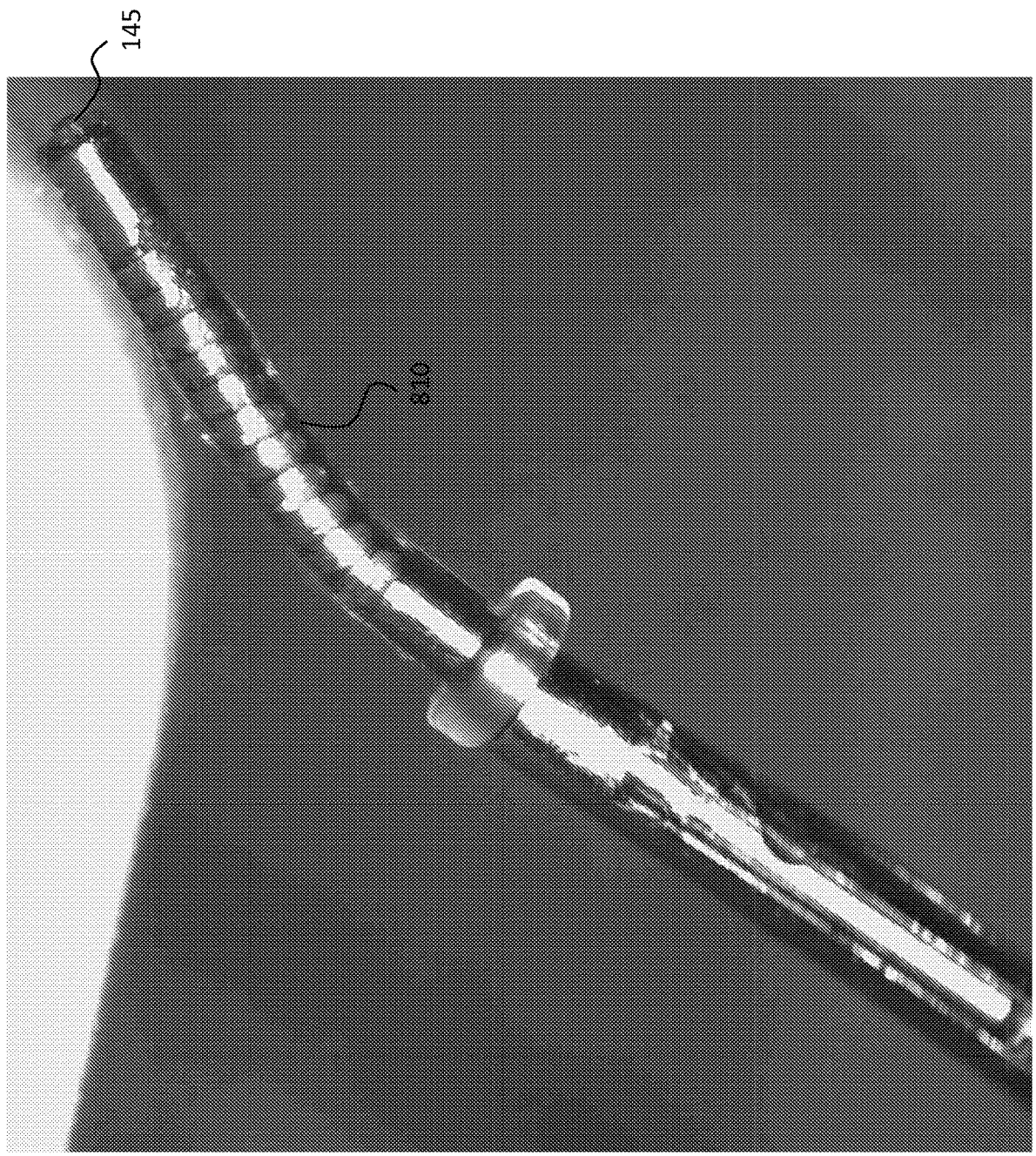

FIGS. 40 and 41 depict exemplary embodiments of insertion tools being used. FIG. 41 depicts an exemplary scenario of bending of the insertion tool.

Any disclosure of any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein can be combined with any other feature of any other embodiment detailed herein providing that the art enables such, unless such is otherwise noted. Any feature disclosed herein can be specifically excluded from an embodiment, providing that such is enabled, unless otherwise noted. That is, some embodiments have insertion tools that specifically do not have one or more of the features disclosed herein.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. A device, comprising:
an insertion tool including an elongate insertion guide that is flexible in a direction lying in at least a plane lying on a longitudinal axis thereof, wherein
the device is an insertion tool for a cochlear electrode array,
the insertion guide is configured to flex in the plane such that a neutral axis is located substantially away from the longitudinal axis,
the guide includes a slit and/or a gap extending parallel to the longitudinal axis,
the guide includes at least two anti-rotation flats, wherein the flats are located away from the slit and/or gap, and
the guide includes a channel, wherein the slit and/or gap is positioned on a top side of the channel and the flats are positioned on respective lateral sides of the channel.

2. The device of claim 1, wherein:
the guide is partially segmented at a plurality of locations that extend about the longitudinal axis and extend through the plane only on one side of the longitudinal axis.

3. The device of claim 2, wherein:
the device includes a silicone barrier; and
the device is configured so that all locations of the partially segmented guide are inside the silicone barrier when the device is used to insert the cochlear electrode array into a cochlea.

4. The device of claim 1, wherein:
the guide has a maximum outer radius lying on a plane normal to the longitudinal axis measured from the longitudinal axis, and the neutral axis is at least 75% of distance of the maximum outer radius from the longitudinal axis when measured on the plane.

5. The device of claim 1, wherein:
the guide has a maximum outer radius lying on a plane normal to the longitudinal axis measured from the longitudinal axis, and the neutral axis is at least 95% of distance of the maximum outer radius from the longitudinal axis when measured on the plane.

6. The device of claim 1, wherein:
surfaces that form the slit and/or gap that extend parallel to the longitudinal axis all lie on respective two planes.

7. The device of claim 1, wherein:
flat surfaces of the flats are substantially parallel to respective surfaces of the slit and/or gap.

8. The device of claim 1, wherein:
the cochlear electrode array moves in the channel during insertion;
the slit and/or gap extends completely from outside the guide to the channel; and
the neutral axis is located, relative to a direction normal to the longitudinal axis, within the slit and/or gap and the elongate insertion guide is configured so that the neutral axis is completely away from the cochlear electrode array when the array is in the channel.

9. The device of claim 1, wherein:
the neutral axis is located, with respect to location on the plane, above the flats.

10. The device of claim 1, wherein:
the device includes a spring clip that is located at a distal end of the elongate insertion guide that establishes the flats.

11. The device of claim 10, wherein:
the spring clip is a U-shaped clip, where arms of the U establish respective flats of the flats.

12. The device of claim 1, wherein:
the cochlear electrode array moves in the channel during insertion and in which the array is located; and
the elongate insertion guide is configured such that the longitudinal axis of the elongate insertion guide at a distal end of the elongate insertion guide can move at least 10 degrees relative to an unbent state without effectively deforming the channel.

13. The device of claim 1, wherein:
at least a portion of the elongate insertion guide is flexible and is made of a polymer body reinforced with a metal-based material.

14. The device of claim 1, wherein:
the guide includes at least a first part and a second part;
the first part is configured to enable the cochlear electrode array to flex beyond that which would be the case if the first part was the same as the second part;
the cochlear electrode array is a pre-curved electrode array; and
the second part is configured to maintain the electrode array in a substantially straight configuration while preventing the electrode array from twisting in response to stresses induced by bias forces which urge the array to return to its pre-curved configuration, when the elongate insertion guide is flexibly bent in the plane.

15. The device of claim 1, wherein:
the elongate insertion guide is located in a cochlea of a human.

16. The device of claim 1, wherein the device is a means for inserting the cochlear electrode array into a cochlea while preventing the cochlear electrode array from twisting during insertion into the cochlea.

17. The device of claim 1, wherein the device includes a stop configured to prevent over insertion of the insertion guide into a human cochlea, wherein a distance from a most distal end of the insertion guide to a front face of the stop is less than 40 mm and wherein the insertion guide is fixed relative to the stop.

18. A device, comprising:
an insertion tool including an elongate insertion guide that is flexible in a direction lying in at least a plane lying on a longitudinal axis thereof, wherein
the device is an insertion tool for a cochlear electrode array,
the insertion guide is configured to flex in the plane such that a neutral axis is located substantially away from the longitudinal axis,
the guide includes a slit and/or a gap extending parallel to the longitudinal axis,
the guide includes at least two anti-rotation flats, wherein the flats are located away from the slit and/or gap; and
the device includes a spring clip that is located at a distal end of the elongate insertion guide that establishes the flats.

19. The device of claim 18, wherein:
the guide is partially segmented at a plurality of locations that extend about the longitudinal axis;
no segments that extend about the longitudinal axis extend to the gap and/or slit; and
the guide is configured to at least limit twisting of the cochlear electrode array during insertion of the cochlear electrode array into a cochlea of a human.

20. The device of claim 18, wherein:
the flats are located entirely within a distance that is 10 mm from a distal tip of the elongate insertion guide.

21. The device of claim 18, wherein:
the cochlear electrode array is located in the insertion tool.

22. The device of claim 18, wherein:
the cochlear electrode array is located in the insertion tool; and
midportions of electrodes of the electrode array are located on a side of the electrode array that is normal to the flats.

23. The device of claim 18, wherein:
the elongate insertion guide includes openings that extend about the longitudinal axis of the guide at a plurality of locations and extend through the plane only on one side of the longitudinal axis.

24. The device of claim 18, wherein respective flats of the at least two anti-rotation flats respectively extend continuously at least 3.0 mm in a longitudinal direction of the insertion guide.

25. The device of claim 20, wherein:
the device includes a handle configured for gripping by a tweezers and/or figures; and
the insertion guide is fixed relative to the handle.

* * * * *